US011851696B2

(12) United States Patent
Lachaux et al.

(10) Patent No.: US 11,851,696 B2
(45) Date of Patent: Dec. 26, 2023

(54) MICROORGANISMS AND PROCESS FOR PRODUCING GLYCOLIC ACID FROM PENTOSES AND HEXOSES

(71) Applicants: Institut National Des Sciences Appliquées De Toulouse, Toulouse (FR); Centre National De La Recherche Scientifique, Paris (FR); Institut National De Recherche Pour L'agriculture, L'alimentation Et L'environnement, Paris (FR)

(72) Inventors: Cléa Lachaux, Toulouse (FR); Thomas Walther, Dresden (DE); Jean-Marie Francois, Plaisance du Touch (FR)

(73) Assignees: Institut National Des Sciences Appliquées De Toulouse, Toulouse (FR); Centre National De La Recherche Scientifique, Paris (FR); Institut National Recherche Pour L'Agriculture, L'Alimentation Et L'Environement, Paris (FR)

(*) Notice: Subject to any disclaimer, the term of this patent is extended or adjusted under 35 U.S.C. 154(b) by 413 days.

(21) Appl. No.: 17/259,124

(22) PCT Filed: Jul. 12, 2019

(86) PCT No.: PCT/FR2019/051760
§ 371 (c)(1),
(2) Date: Jan. 8, 2021

(87) PCT Pub. No.: WO2020/012138
PCT Pub. Date: Jan. 16, 2020

(65) Prior Publication Data
US 2021/0171989 A1 Jun. 10, 2021

(30) Foreign Application Priority Data
Jul. 13, 2018 (FR) .................................. 1856511

(51) Int. Cl.
*C12P 7/42* (2006.01)
*C12N 1/04* (2006.01)
(52) U.S. Cl.
CPC .................. *C12P 7/42* (2013.01); *C12N 1/04* (2013.01); *C12N 2500/34* (2013.01)
(58) Field of Classification Search
CPC ....................................... C12N 9/20; C12P 7/42
See application file for complete search history.

(56) References Cited

FOREIGN PATENT DOCUMENTS

| WO | WO 2007/141316 A2 | 12/2007 |
| WO | WO 2016/079440 A1 | 5/2016 |
| WO | WO 2017/009236 A2 | 1/2017 |
| WO | WO 2017/059236 A1 | 4/2017 |

OTHER PUBLICATIONS

Alexeeva et al., "Requirement of ArcA for redox regulation in *Escherichia coli* under microaerobic but not anaerobic or aerobic conditions," J Bacteriol., 185(1):204-209, (2003).
Alkim et al., "The synthetic xylulose-1 phosphate pathway increases production of glycolic acid from xylose-rich sugar mixtures," Biotechnology for Biofuels, 9:201, 11 pages, (2016).
Atkinson and Watson, "Kinetics of regulatory enzymes: *Escherichia coli* phosphofructokinase," The Journal of Biological Chemistry, 240(2):757-764, (1965).
Baba et al., "Construction of *Escherichia coli* K-12 in-frame, single-gene knockout mutants: The Keio collection," Molecular Systems Biology, 2, 2006.0008, 11 pages, (2006).
Baldomà and Aguilar, "Involvement of lactaldehyde dehydrogenase in several metabolic pathways of *Escherichia coli* K12," The Journal of Biological Chemistry, 262(29):13991-13996, (1987).
Banerjee and Fraenkel, "Glucose-6-phosphate dehydrogenase from *Escherichia coli* and from "high level" mutant," J. Bacteriol., 110(1):155-160, (1972).
Bogorad et al., "Synthetic non-oxidative glycolysis enables complete carbon conservation," Nature, 502:693-697, (2013).
Bremer et al., "λ placMu: A transposable derivative of bacteriophage lambda for creating lacZ protein fusions in a single step," Journal of Bacteriology, 158(3):1084-1093, (1984).
Cabulong et al., "Engineering *Escherichia coli* for glycolic acid production from D-xylose through the Dahms pathway and glyoxylate bypass," Applied Microbiology and Biotechnology, 102(5):2179-2189, (2018).
Cho et al., "Transcriptional regulation of the fad regulon genes of *Escherichia coli* by ArcA," Microbiology, 152:2207-2219, (2006).
Chung et al., "One-step preparation of competent *Escherichia coli*: transformation and storage of bacterial cells in the same solution," Proceedings of the National Academy of Sciences, 86:2172-2175, (1989).

(Continued)

*Primary Examiner* — Tekchand Saidha
(74) *Attorney, Agent, or Firm* — Alston & Bird

(57) ABSTRACT

The present invention relates to a recombinant microorganism which exhibits i) a conversion activity from D-ribulose-5-phosphate into D-arabinose-5-phosphate, increased in comparison with the same, non-modified microorganism; ii) a cleavage catalysis activity from D-arabinose-5-phosphate into D-glyceraldehyde-3-phosphate and glycolaldehyde, increased in comparison with the same, non-modified microorganism; iii) an oxidation activity from glycolaldehyde into glycolate, increased in comparison with the same, non-modified microorganism; and iv) an oxidation activity from glyceraldehyde-3-phosphate into 1,3-bisphosphoglycerate, decreased in comparison with the same, non-modified microorganism. The present invention also relates to a process for preparing glycolic acid from pentoses and/or hexoses, using such a recombinant microorganism. The present invention also relates to a process for producing glycolic acid involving a biomass production phase and a bioconversion phase from hexoses and/or pentoses into glycolic acid.

14 Claims, 9 Drawing Sheets

Specification includes a Sequence Listing.

(56) References Cited

OTHER PUBLICATIONS

Deng et al., "Balancing the carbon flux distributions between the TCA cycle and glyoxylate shunt to produce glycolate at high yield and titer in *Escherichia coli*," Metabolic Engineering, 46:28-34, (2018).

Dugar and Stephanopoulos, "Relative potential of biosynthetic pathways for biofuels and bio-based products," Nat Biotechnol, 29(12):1074-1078, (2011).

Dykxhoorn et al., "A set of compatible tac promoter expression vectors," Gene, 177:133-136, (1996).

Fong et al., "Directed evolution of D-2-keto-3-deoxy-6-phosphogluconate aldolase to new variants for the efficient synthesis of D- and L-sugars," Chemistry and Biology, 7(11):873-883, (2000).

Gädda et al., "The industrial potential of bio-based glycolic acid and polyglycolic acid," Appita Journal, 67:352, (2014).

Ganter and Pluckthun, "Glycine to alanine substitutions in helices of glyceraldehyde-3-phosphate dehydrogenase : effects on stability," Biochemistry, 29(40):9395-2402, (1990).

Gardner and Fridovich, "Superoxide sensitivity of the *Escherichia coli* aconitase," Journal of Biological Chemistry, 266(29):19328-19333, (1991).

Garrabou et al., "Asymmetric self- and cross-aldol reactions of glycolaldehyde catalyzed by d-fructose-6-phosphate aldolase," Angewandte Chemie—International Edition, 48:5521-5525, (2009).

Heath and Ghalambor, "The metabolism of L-Fucose," The Journal of Biological Chemistry, 237(8):2427-2433, (1962).

Hernández-Montvalvo et al., "Characterization of sugar mixtures utilization by an *Escherichia coli* mutant devoid of the phosphotransferase system," Applied Microbiology and Biotechnology, 57:186-191, (2001).

Hernández-Montvalvo et al., "Expression of galP and glk in a *Escherichia coli* PTS mutant restores glucose transport and increases glycolytic flux to fermentation products," Biotechnology and Bioengineering, 83(6):687-694, (2003).

Jørgensen et al., "Enzymatic conversion of lignocellulose into fermentable sugars: Challenges and opportunities," Biofuels, Bioproducts and Biorefining, 1:119-134, (2007).

Kunze et al., "A central role for the peroxisomal membrane in glyoxylate cycle function," Biochimica et Biophysica Acta—Molecular Cell Research, 1763:1441-1452, (2006).

Liu and De Wulf, "Probing the ArcA-P Modulon of *Escherichia coli* by Whole Genome Transcriptional Analysis and Sequence Recognition Profiling," Journal of Biological Chemistry, 279(13):12588-12597, (2004).

Lord, J.M., "Glycolate oxidoreductase in *Escherichia coli*," Biochimica et Biophysica Acta, 267:227-237, (1972).

Lu et al., "Combinatorial modulation of galP and glk gene expression for improved alternative glucose utilization," Applied Microbiology and Biotechnology, 93:2455-2462, (2012).

Meredith and Woodard, "Characterization of *Escherichia coli* D-arabinose 5-phosphate isomerase encoded by kpsF : implications for group 2 capsule biosynthesis," Biochemical Journal, 395:427-432, (2006).

Pellicer et al., "A mutational study of the ArcA-P binding sequences in the aldA promoter of *Escherichia coli*," Molecular and General Genetics, 261:170-176, (1999).

Pereira et al., "Efficient utilization of pentoses for bioproduction of the renewable two-carbon compounds ethylene glycol and glycolate," Metabolic Engineering, 34:80-87, (2016).

Saadat and Harrison, "Identification of catalytic bases in the active site of *Escherichia coli* methylglyoxal synthase: Cloning, expression, and functional characterization of conserved aspartic acid residues," Biochemistry, 37(28):10074-10086, (1998).

Schürmann and Sprenger, "Fructose-6-phosphate aldolase is a novel class I aldolase from *Escherichia coli* and is related to a novel group of bacterial transaldolases," Journal of Biological Chemistry, 276(14):11055-11061, (2001).

Snoep et al., "Reconstitution of glucose uptake and phosphorylation in a glucose-negative mutant of *Escherichia coli* by using Zymomonas mobilis genes encoding the glucose facilitator protein and glucokinase," J. Bacteriol., 176(7):2133-2135, (1994).

Szekrenyi et al., "Engineering the donor selectivity of D-fructose-6-phosphate aldolase for biocatalytic asymmetric cross-aldol additions of glycolaldehyde," Chemistry—A European Journal, 20:12572-12583, (2014).

Teleman et al., "Identification and quantitation of phosphorus metabolites in yeast neutral pH extracts by nuclear magnetic resonance spectroscopy," Analytical Biochemistry, 272:71-79, (1999).

Ward et al., "Expression of prokaryotic membrane transport proteins in *Escherichia coli*," Biochemical Society Transactions, 27(6):893-899, (1999).

Zhao and Winkler, "An *Escherichia coli* K-12 tktA tktB mutant deficient in transketolase activity requires pyridoxine (vitamin B6) as well as the aromatic amino acids and vitamins for growth," J. Bacteriol., 176(19):6134-6138, (1994).

WIPO Application No. PCT/FR2019/051760, PCT International Search Report and Written Opinion of the International Searching Authority dated Oct. 17, 2019.

French Application No. 1856511, Preliminary Search Report dated Mar. 12, 2019.

SEQUENCE LISTING

<160> NUMBER OF SEQ ID NOS: 43

<210> SEQ ID NO 1
<211> LENGTH: 321
<212> TYPE: PRT
<213> ORGANISM: E.coli strain K12 MG1655
<220> FEATURE:
<221> NAME/KEY: PEPTIDE
<222> LOCATION: (1)..(321)
<223> OTHER INFORMATION: Protein coded by the gene kdsD

<400> SEQUENCE: 1

Met Ser Glu Ala Leu Leu Asn Ala Gly Arg Gln Thr Leu Met Leu Glu
1               5                   10                  15

Leu Gln Glu Ala Ser Arg Leu Pro Glu Arg Leu Gly Asp Asp Phe Val
            20                  25                  30

Arg Ala Ala Asn Ile Ile Leu His Cys Glu Gly Lys Val Val Val Ser
        35                  40                  45

Gly Ile Gly Lys Ser Gly His Ile Gly Lys Lys Ile Ala Ala Thr Leu
    50                  55                  60

Ala Ser Thr Gly Thr Pro Ala Phe Phe Val His Pro Ala Glu Ala Leu
65                  70                  75                  80

His Gly Asp Leu Gly Met Ile Glu Ser Arg Asp Val Met Leu Phe Ile
                85                  90                  95

Ser Tyr Ser Gly Gly Ala Lys Glu Leu Asp Leu Ile Ile Pro Arg Leu
            100                 105                 110

Glu Asp Lys Ser Ile Ala Leu Leu Ala Met Thr Gly Lys Pro Thr Ser
        115                 120                 125

Pro Leu Gly Leu Ala Ala Lys Ala Val Leu Asp Ile Ser Val Glu Arg
    130                 135                 140

Glu Ala Cys Pro Met His Leu Ala Pro Thr Ser Ser Thr Val Asn Thr
145                 150                 155                 160

Leu Met Met Gly Asp Ala Leu Ala Met Ala Val Met Gln Ala Arg Gly
                165                 170                 175

Phe Asn Glu Glu Asp Phe Ala Arg Ser His Pro Ala Gly Ala Leu Gly
            180                 185                 190

Ala Arg Leu Leu Asn Lys Val His His Leu Met Arg Arg Asp Asp Ala
        195                 200                 205

Ile Pro Gln Val Ala Leu Thr Ala Ser Val Met Asp Ala Met Leu Glu
    210                 215                 220

Leu Ser Arg Thr Gly Leu Gly Leu Val Ala Val Cys Asp Ala Gln Gln
225                 230                 235                 240

Gln Val Gln Gly Val Phe Thr Asp Gly Asp Leu Arg Arg Trp Leu Val
                245                 250                 255

Gly Gly Gly Ala Leu Thr Thr Pro Val Asn Glu Ala Met Thr Val Gly
            260                 265                 270

Gly Thr Thr Leu Gln Ser Gln Ser Arg Ala Ile Asp Ala Lys Glu Ile
        275                 280                 285

Leu Met Lys Arg Lys Ile Thr Ala Ala Pro Val Val Asp Glu Asn Gly
    290                 295                 300

Lys Leu Thr Gly Ala Ile Asn Leu Gln Asp Phe Tyr Gln Ala Gly Ile
305                 310                 315                 320

Ile

<210> SEQ ID NO 2
<211> LENGTH: 220

```
<212> TYPE: PRT
<213> ORGANISM: E.coli strain K12 MG1655
<220> FEATURE:
<221> NAME/KEY: PEPTIDE
<222> LOCATION: (1)..(220)
<223> OTHER INFORMATION: Protein coded by the gene fsaA

<400> SEQUENCE: 2

Met Glu Leu Tyr Leu Asp Thr Ser Asp Val Ala Val Lys Ala Leu
1               5                   10                  15

Ser Arg Ile Phe Pro Leu Ala Gly Val Thr Thr Asn Pro Ser Ile Ile
            20                  25                  30

Ala Ala Gly Lys Lys Pro Leu Asp Val Val Leu Pro Gln Leu His Glu
        35                  40                  45

Ala Met Gly Gly Gln Gly Arg Leu Phe Ala Gln Val Met Ala Thr Thr
    50                  55                  60

Ala Glu Gly Met Val Asn Asp Ala Leu Lys Leu Arg Ser Ile Ile Ala
65                  70                  75                  80

Asp Ile Val Val Lys Val Pro Val Thr Ala Glu Gly Leu Ala Ala Ile
                85                  90                  95

Lys Met Leu Lys Ala Glu Gly Ile Pro Thr Leu Gly Thr Ala Val Tyr
            100                 105                 110

Gly Ala Ala Gln Gly Leu Leu Ser Ala Leu Ala Gly Ala Glu Tyr Val
        115                 120                 125

Ala Pro Tyr Val Asn Arg Ile Asp Ala Gln Gly Gly Ser Gly Ile Gln
    130                 135                 140

Thr Val Thr Asp Leu His Gln Leu Leu Lys Met His Ala Pro Gln Ala
145                 150                 155                 160

Lys Val Leu Ala Ala Ser Phe Lys Thr Pro Arg Gln Ala Leu Asp Cys
                165                 170                 175

Leu Leu Ala Gly Cys Glu Ser Ile Thr Leu Pro Leu Asp Val Ala Gln
            180                 185                 190

Gln Met Ile Ser Tyr Pro Ala Val Asp Ala Ala Val Ala Lys Phe Glu
        195                 200                 205

Gln Asp Trp Gln Gly Ala Phe Gly Arg Thr Ser Ile
    210                 215                 220

<210> SEQ ID NO 3
<211> LENGTH: 220
<212> TYPE: PRT
<213> ORGANISM: E. coli strain K12 MG1655
<220> FEATURE:
<221> NAME/KEY: PEPTIDE
<222> LOCATION: (1)..(220)
<223> OTHER INFORMATION: Protein coded by the gene fsaB

<400> SEQUENCE: 3

Met Glu Leu Tyr Leu Asp Thr Ala Asn Val Ala Glu Val Glu Arg Leu
1               5                   10                  15

Ala Arg Ile Phe Pro Ile Ala Gly Val Thr Thr Asn Pro Ser Ile Ile
            20                  25                  30

Ala Ala Ser Lys Glu Ser Ile Trp Glu Val Leu Pro Arg Leu Gln Lys
        35                  40                  45

Ala Ile Gly Asp Glu Gly Ile Leu Phe Ala Gln Thr Met Ser Arg Asp
    50                  55                  60

Ala Gln Gly Met Val Glu Glu Ala Lys Arg Leu Arg Asp Ala Ile Pro
65                  70                  75                  80

Gly Ile Val Val Lys Ile Pro Val Thr Ser Glu Gly Leu Ala Ala Ile
```

```
            85                  90                  95
Lys Ile Leu Lys Lys Glu Gly Ile Thr Thr Leu Gly Thr Ala Val Tyr
            100                 105                 110

Ser Ala Ala Gln Gly Leu Leu Ala Ala Leu Ala Gly Ala Lys Tyr Val
            115                 120                 125

Ala Pro Tyr Val Asn Arg Val Asp Ala Gln Gly Gly Asp Gly Ile Arg
            130                 135                 140

Thr Val Gln Glu Leu Gln Thr Leu Leu Glu Met His Ala Pro Glu Ser
145                 150                 155                 160

Met Val Leu Ala Ala Ser Phe Lys Thr Pro Arg Gln Ala Leu Asp Cys
            165                 170                 175

Leu Leu Ala Gly Cys Glu Ser Ile Thr Leu Pro Leu Asp Val Ala Gln
            180                 185                 190

Gln Met Leu Asn Thr Pro Ala Val Glu Ser Ala Ile Glu Lys Phe Glu
            195                 200                 205

His Asp Trp Asn Ala Ala Phe Gly Thr Thr His Leu
            210                 215                 220
```

<210> SEQ ID NO 4
<211> LENGTH: 479
<212> TYPE: PRT
<213> ORGANISM: E.coli strain K12 MG1655
<220> FEATURE:
<221> NAME/KEY: PEPTIDE
<222> LOCATION: (1)..(479)
<223> OTHER INFORMATION: Protein coded by the gene aldA

<400> SEQUENCE: 4

```
Met Ser Val Pro Val Gln His Pro Met Tyr Ile Asp Gly Gln Phe Val
1               5                   10                  15

Thr Trp Arg Gly Asp Ala Trp Ile Asp Val Val Asn Pro Ala Thr Glu
            20                  25                  30

Ala Val Ile Ser Arg Ile Pro Asp Gly Gln Ala Glu Asp Ala Arg Lys
            35                  40                  45

Ala Ile Asp Ala Ala Glu Arg Ala Gln Pro Glu Trp Glu Ala Leu Pro
            50                  55                  60

Ala Ile Glu Arg Ala Ser Trp Leu Arg Lys Ile Ser Ala Gly Ile Arg
65                  70                  75                  80

Glu Arg Ala Ser Glu Ile Ser Ala Leu Ile Val Glu Glu Gly Gly Lys
            85                  90                  95

Ile Gln Gln Leu Ala Glu Val Glu Val Ala Phe Thr Ala Asp Tyr Ile
            100                 105                 110

Asp Tyr Met Ala Glu Trp Ala Arg Arg Tyr Glu Gly Glu Ile Ile Gln
            115                 120                 125

Ser Asp Arg Pro Gly Glu Asn Ile Leu Leu Phe Lys Arg Ala Leu Gly
            130                 135                 140

Val Thr Thr Gly Ile Leu Pro Trp Asn Phe Pro Phe Phe Leu Ile Ala
145                 150                 155                 160

Arg Lys Met Ala Pro Ala Leu Leu Thr Gly Asn Thr Ile Val Ile Lys
            165                 170                 175

Pro Ser Glu Phe Thr Pro Asn Asn Ala Ile Ala Phe Ala Lys Ile Val
            180                 185                 190

Asp Glu Ile Gly Leu Pro Arg Gly Val Phe Asn Leu Val Leu Gly Arg
            195                 200                 205

Gly Glu Thr Val Gly Gln Glu Leu Ala Gly Asn Pro Lys Val Ala Met
            210                 215                 220
```

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
                260                 265                 270

Ile Val Asp Ser Arg Val Ile Asn Ser Gly Gln Val Cys Asn Cys Ala
                275                 280                 285

Glu Arg Val Tyr Val Gln Lys Gly Ile Tyr Asp Gln Phe Val Asn Arg
                290                 295                 300

Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Ala Leu Glu Arg
                325                 330                 335

Val Glu Gln Lys Val Ala Arg Ala Val Glu Glu Gly Ala Arg Val Ala
                340                 345                 350

Phe Gly Gly Lys Ala Val Glu Gly Lys Gly Tyr Tyr Tyr Pro Pro Thr
                355                 360                 365

Leu Leu Leu Asp Val Arg Gln Glu Met Ser Ile Met His Glu Glu Thr
370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
                405                 410                 415

Thr Gln Asn Leu Asn Val Ala Met Lys Ala Ile Lys Gly Leu Lys Phe
                420                 425                 430

Gly Glu Thr Tyr Ile Asn Arg Glu Asn Phe Glu Ala Met Gln Gly Phe
                435                 440                 445

His Ala Gly Trp Arg Lys Ser Gly Ile Gly Gly Ala Asp Gly Lys His
                450                 455                 460

Gly Leu His Glu Tyr Leu Gln Thr Gln Val Val Tyr Leu Gln Ser
465                 470                 475

<210> SEQ ID NO 5
<211> LENGTH: 331
<212> TYPE: PRT
<213> ORGANISM: E.coli strain K12 MG1655
<220> FEATURE:
<221> NAME/KEY: PEPTIDE
<222> LOCATION: (1)..(331)
<223> OTHER INFORMATION: Protein coded by the gene gapA

<400> SEQUENCE: 5

Met Thr Ile Lys Val Gly Ile Asn Gly Phe Gly Arg Ile Gly Arg Ile
1               5                   10                  15

Val Phe Arg Ala Ala Gln Lys Arg Ser Asp Ile Glu Ile Val Ala Ile
                20                  25                  30

Asn Asp Leu Leu Asp Ala Asp Tyr Met Ala Tyr Met Leu Lys Tyr Asp
                35                  40                  45

Ser Thr His Gly Arg Phe Asp Gly Thr Val Glu Val Lys Asp Gly His
                50                  55                  60

Leu Ile Val Asn Gly Lys Lys Ile Arg Val Thr Ala Glu Arg Asp Pro
65                  70                  75                  80

Ala Asn Leu Lys Trp Asp Glu Val Gly Val Asp Val Val Ala Glu Ala
                85                  90                  95

Thr Gly Leu Phe Leu Thr Asp Glu Thr Ala Arg Lys His Ile Thr Ala
                100                 105                 110

Gly Ala Lys Lys Val Val Met Thr Gly Pro Ser Lys Asp Asn Thr Pro
            115                 120                 125

Met Phe Val Lys Gly Ala Asn Phe Asp Lys Tyr Ala Gly Gln Asp Ile
        130                 135                 140

Val Ser Asn Ala Ser Cys Thr Thr Asn Cys Leu Ala Pro Leu Ala Lys
145                 150                 155                 160

Val Ile Asn Asp Asn Phe Gly Ile Ile Glu Gly Leu Met Thr Thr Val
                165                 170                 175

His Ala Thr Thr Ala Thr Gln Lys Thr Val Asp Gly Pro Ser His Lys
            180                 185                 190

Asp Trp Arg Gly Gly Arg Gly Ala Ser Gln Asn Ile Ile Pro Ser Ser
        195                 200                 205

Thr Gly Ala Ala Lys Ala Val Gly Lys Val Leu Pro Glu Leu Asn Gly
210                 215                 220

Lys Leu Thr Gly Met Ala Phe Arg Val Pro Thr Pro Asn Val Ser Val
225                 230                 235                 240

Val Asp Leu Thr Val Arg Leu Glu Lys Ala Ala Thr Tyr Glu Gln Ile
                245                 250                 255

Lys Ala Ala Val Lys Ala Ala Ala Glu Gly Glu Met Lys Gly Val Leu
            260                 265                 270

Gly Tyr Thr Glu Asp Asp Val Val Ser Thr Asp Phe Asn Gly Glu Val
        275                 280                 285

Cys Thr Ser Val Phe Asp Ala Lys Ala Gly Ile Ala Leu Asn Asp Asn
290                 295                 300

Phe Val Lys Leu Val Ser Trp Tyr Asp Asn Glu Thr Gly Tyr Ser Asn
305                 310                 315                 320

Lys Val Leu Asp Leu Ile Ala His Ile Ser Lys
                325                 330

<210> SEQ ID NO 6
<211> LENGTH: 85
<212> TYPE: PRT
<213> ORGANISM: E.coli strain K12 MG1655
<220> FEATURE:
<221> NAME/KEY: PEPTIDE
<222> LOCATION: (1)..(85)
<223> OTHER INFORMATION: Protein coded by the gene ptsH

<400> SEQUENCE: 6

Met Phe Gln Gln Glu Val Thr Ile Thr Ala Pro Asn Gly Leu His Thr
1               5                   10                  15

Arg Pro Ala Ala Gln Phe Val Lys Glu Ala Lys Gly Phe Thr Ser Glu
            20                  25                  30

Ile Thr Val Thr Ser Asn Gly Lys Ser Ala Ser Ala Lys Ser Leu Phe
        35                  40                  45

Lys Leu Gln Thr Leu Gly Leu Thr Gln Gly Thr Val Val Thr Ile Ser
    50                  55                  60

Ala Glu Gly Glu Asp Glu Gln Lys Ala Val Glu His Leu Val Lys Leu
65                  70                  75                  80

Met Ala Glu Leu Glu
                85

<210> SEQ ID NO 7
<211> LENGTH: 575
<212> TYPE: PRT

<213> ORGANISM: E.coli strain K12 MG1655
<220> FEATURE:
<221> NAME/KEY: PEPTIDE
<222> LOCATION: (1)..(575)
<223> OTHER INFORMATION: Protein coded by the gene ptsI

<400> SEQUENCE: 7

Met Ile Ser Gly Ile Leu Ala Ser Pro Gly Ile Ala Phe Gly Lys Ala
1               5                   10                  15

Leu Leu Leu Lys Glu Asp Glu Ile Val Ile Asp Arg Lys Lys Ile Ser
            20                  25                  30

Ala Asp Gln Val Asp Gln Glu Val Glu Arg Phe Leu Ser Gly Arg Ala
        35                  40                  45

Lys Ala Ser Ala Gln Leu Glu Thr Ile Lys Thr Lys Ala Gly Glu Thr
50                  55                  60

Phe Gly Glu Glu Lys Glu Ala Ile Phe Glu Gly His Ile Met Leu Leu
65                  70                  75                  80

Glu Asp Glu Glu Leu Glu Gln Glu Ile Ile Ala Leu Ile Lys Asp Lys
                85                  90                  95

His Met Thr Ala Asp Ala Ala His Glu Val Ile Glu Gly Gln Ala
            100                 105                 110

Ser Ala Leu Glu Glu Leu Asp Asp Glu Tyr Leu Lys Glu Arg Ala Ala
        115                 120                 125

Asp Val Arg Asp Ile Gly Lys Arg Leu Leu Arg Asn Ile Leu Gly Leu
130                 135                 140

Lys Ile Ile Asp Leu Ser Ala Ile Gln Asp Glu Val Ile Leu Val Ala
145                 150                 155                 160

Ala Asp Leu Thr Pro Ser Glu Thr Ala Gln Leu Asn Leu Lys Lys Val
                165                 170                 175

Leu Gly Phe Ile Thr Asp Ala Gly Gly Arg Thr Ser His Thr Ser Ile
            180                 185                 190

Met Ala Arg Ser Leu Glu Leu Pro Ala Ile Val Gly Thr Gly Ser Val
        195                 200                 205

Thr Ser Gln Val Lys Asn Asp Asp Tyr Leu Ile Leu Asp Ala Val Asn
210                 215                 220

Asn Gln Val Tyr Val Asn Pro Thr Asn Glu Val Ile Asp Lys Met Arg
225                 230                 235                 240

Ala Val Gln Glu Gln Val Ala Ser Glu Lys Ala Glu Leu Ala Lys Leu
                245                 250                 255

Lys Asp Leu Pro Ala Ile Thr Leu Asp Gly His Gln Val Glu Val Cys
            260                 265                 270

Ala Asn Ile Gly Thr Val Arg Asp Val Glu Gly Ala Glu Arg Asn Gly
        275                 280                 285

Ala Glu Gly Val Gly Leu Tyr Arg Thr Glu Phe Leu Phe Met Asp Arg
290                 295                 300

Asp Ala Leu Pro Thr Glu Glu Glu Gln Phe Ala Ala Tyr Lys Ala Val
305                 310                 315                 320

Ala Glu Ala Cys Gly Ser Gln Ala Val Ile Val Arg Thr Met Asp Ile
                325                 330                 335

Gly Gly Asp Lys Glu Leu Pro Tyr Met Asn Phe Pro Lys Glu Glu Asn
            340                 345                 350

Pro Phe Leu Gly Trp Arg Ala Ile Arg Ile Ala Met Asp Arg Arg Glu
        355                 360                 365

Ile Leu Arg Asp Gln Leu Arg Ala Ile Leu Arg Ala Ser Ala Phe Gly
370                 375                 380

```
Lys Leu Arg Ile Met Phe Pro Met Ile Ile Ser Val Glu Glu Val Arg
385                 390                 395                 400

Ala Leu Arg Lys Glu Ile Glu Ile Tyr Lys Gln Glu Leu Arg Asp Glu
            405                 410                 415

Gly Lys Ala Phe Asp Glu Ser Ile Glu Ile Gly Val Met Val Glu Thr
        420                 425                 430

Pro Ala Ala Ala Thr Ile Ala Arg His Leu Ala Lys Glu Val Asp Phe
            435                 440                 445

Phe Ser Ile Gly Thr Asn Asp Leu Thr Gln Tyr Thr Leu Ala Val Asp
        450                 455                 460

Arg Gly Asn Asp Met Ile Ser His Leu Tyr Gln Pro Met Ser Pro Ser
465                 470                 475                 480

Val Leu Asn Leu Ile Lys Gln Val Ile Asp Ala Ser His Ala Glu Gly
                485                 490                 495

Lys Trp Thr Gly Met Cys Gly Glu Leu Ala Gly Asp Glu Arg Ala Thr
            500                 505                 510

Leu Leu Leu Leu Gly Met Gly Leu Asp Glu Phe Ser Met Ser Ala Ile
            515                 520                 525

Ser Ile Pro Arg Ile Lys Lys Ile Ile Arg Asn Thr Asn Phe Glu Asp
530                 535                 540

Ala Lys Val Leu Ala Glu Gln Ala Leu Ala Gln Pro Thr Thr Asp Glu
545                 550                 555                 560

Leu Met Thr Leu Val Asn Lys Phe Ile Glu Glu Lys Thr Ile Cys
                565                 570                 575

<210> SEQ ID NO 8
<211> LENGTH: 169
<212> TYPE: PRT
<213> ORGANISM: E.coli strain K12 MG1655
<220> FEATURE:
<221> NAME/KEY: PEPTIDE
<222> LOCATION: (1)..(169)
<223> OTHER INFORMATION: Protein coded by the gene crr

<400> SEQUENCE: 8

Met Gly Leu Phe Asp Lys Leu Lys Ser Leu Val Ser Asp Asp Lys Lys
1               5                   10                  15

Asp Thr Gly Thr Ile Glu Ile Ile Ala Pro Leu Ser Gly Glu Ile Val
            20                  25                  30

Asn Ile Glu Asp Val Pro Asp Val Val Phe Ala Glu Lys Ile Val Gly
        35                  40                  45

Asp Gly Ile Ala Ile Lys Pro Thr Gly Asn Lys Met Val Ala Pro Val
50                  55                  60

Asp Gly Thr Ile Gly Lys Ile Phe Glu Thr Asn His Ala Phe Ser Ile
65                  70                  75                  80

Glu Ser Asp Ser Gly Val Glu Leu Phe Val His Phe Gly Ile Asp Thr
                85                  90                  95

Val Glu Leu Lys Gly Glu Gly Phe Lys Arg Ile Ala Glu Glu Gly Gln
            100                 105                 110

Arg Val Lys Val Gly Asp Thr Val Ile Glu Phe Asp Leu Pro Leu Leu
        115                 120                 125

Glu Glu Lys Ala Lys Ser Thr Leu Thr Pro Val Val Ile Ser Asn Met
    130                 135                 140

Asp Glu Ile Lys Glu Leu Ile Lys Leu Ser Gly Ser Val Thr Val Gly
145                 150                 155                 160
```

-continued

```
Glu Thr Pro Val Ile Arg Ile Lys Lys
            165

<210> SEQ ID NO 9
<211> LENGTH: 477
<212> TYPE: PRT
<213> ORGANISM: E.coli strain K12 MG1655
<220> FEATURE:
<221> NAME/KEY: PEPTIDE
<222> LOCATION: (1)..(477)
<223> OTHER INFORMATION: Protein coded by the gene ptsG

<400> SEQUENCE: 9

Met Phe Lys Asn Ala Phe Ala Asn Leu Gln Lys Val Gly Lys Ser Leu
1               5                   10                  15

Met Leu Pro Val Ser Val Leu Pro Ile Ala Gly Ile Leu Leu Gly Val
            20                  25                  30

Gly Ser Ala Asn Phe Ser Trp Leu Pro Ala Val Val Ser His Val Met
        35                  40                  45

Ala Glu Ala Gly Gly Ser Val Phe Ala Asn Met Pro Leu Ile Phe Ala
    50                  55                  60

Ile Gly Val Ala Leu Gly Phe Thr Asn Asn Asp Gly Val Ser Ala Leu
65                  70                  75                  80

Ala Ala Val Val Ala Tyr Gly Ile Met Val Lys Thr Met Ala Val Val
                85                  90                  95

Ala Pro Leu Val Leu His Leu Pro Ala Glu Glu Ile Ala Ser Lys His
            100                 105                 110

Leu Ala Asp Thr Gly Val Leu Gly Gly Ile Ile Ser Gly Ala Ile Ala
        115                 120                 125

Ala Tyr Met Phe Asn Arg Phe Tyr Arg Ile Lys Leu Pro Glu Tyr Leu
    130                 135                 140

Gly Phe Phe Ala Gly Lys Arg Phe Val Pro Ile Ile Ser Gly Leu Ala
145                 150                 155                 160

Ala Ile Phe Thr Gly Val Val Leu Ser Phe Ile Trp Pro Pro Ile Gly
                165                 170                 175

Ser Ala Ile Gln Thr Phe Ser Gln Trp Ala Ala Tyr Gln Asn Pro Val
            180                 185                 190

Val Ala Phe Gly Ile Tyr Gly Phe Ile Glu Arg Cys Leu Val Pro Phe
        195                 200                 205

Gly Leu His His Ile Trp Asn Val Pro Phe Gln Met Gln Ile Gly Glu
    210                 215                 220

Tyr Thr Asn Ala Ala Gly Gln Val Phe His Gly Asp Ile Pro Arg Tyr
225                 230                 235                 240

Met Ala Gly Asp Pro Thr Ala Gly Lys Leu Ser Gly Gly Phe Leu Phe
                245                 250                 255

Lys Met Tyr Gly Leu Pro Ala Ala Ala Ile Ala Ile Trp His Ser Ala
            260                 265                 270

Lys Pro Glu Asn Arg Ala Lys Val Gly Gly Ile Met Ile Ser Ala Ala
        275                 280                 285

Leu Thr Ser Phe Leu Thr Gly Ile Thr Glu Pro Ile Glu Phe Ser Phe
    290                 295                 300

Met Phe Val Ala Pro Ile Leu Tyr Ile Ile His Ala Ile Leu Ala Gly
305                 310                 315                 320

Leu Ala Phe Pro Ile Cys Ile Leu Leu Gly Met Arg Asp Gly Thr Ser
                325                 330                 335

Phe Ser His Gly Leu Ile Asp Phe Ile Val Leu Ser Gly Asn Ser Ser
```

```
                340             345             350
Lys Leu Trp Leu Phe Pro Ile Val Gly Ile Gly Tyr Ala Ile Val Tyr
            355                 360                 365

Tyr Thr Ile Phe Arg Val Leu Ile Lys Ala Leu Asp Leu Lys Thr Pro
        370                 375                 380

Gly Arg Glu Asp Ala Thr Glu Asp Ala Lys Ala Thr Gly Thr Ser Glu
385                 390                 395                 400

Met Ala Pro Ala Leu Val Ala Ala Phe Gly Gly Lys Glu Asn Ile Thr
                405                 410                 415

Asn Leu Asp Ala Cys Ile Thr Arg Leu Arg Val Ser Val Ala Asp Val
            420                 425                 430

Ser Lys Val Asp Gln Ala Gly Leu Lys Lys Leu Gly Ala Ala Gly Val
        435                 440                 445

Val Val Ala Gly Ser Gly Val Gln Ala Ile Phe Gly Thr Lys Ser Asp
    450                 455                 460

Asn Leu Lys Thr Glu Met Asp Glu Tyr Ile Arg Asn His
465                 470                 475

<210> SEQ ID NO 10
<211> LENGTH: 464
<212> TYPE: PRT
<213> ORGANISM: E.coli strain K12 MG1655
<220> FEATURE:
<221> NAME/KEY: PEPTIDE
<222> LOCATION: (1)..(464)
<223> OTHER INFORMATION: Protein coded by the gene galP

<400> SEQUENCE: 10

Met Pro Asp Ala Lys Lys Gln Gly Arg Ser Asn Lys Ala Met Thr Phe
1               5                   10                  15

Phe Val Cys Phe Leu Ala Ala Leu Ala Gly Leu Leu Phe Gly Leu Asp
            20                  25                  30

Ile Gly Val Ile Ala Gly Ala Leu Pro Phe Ile Ala Asp Glu Phe Gln
        35                  40                  45

Ile Thr Ser His Thr Gln Glu Trp Val Val Ser Ser Met Met Phe Gly
    50                  55                  60

Ala Ala Val Gly Ala Val Gly Ser Gly Trp Leu Ser Phe Lys Leu Gly
65                  70                  75                  80

Arg Lys Lys Ser Leu Met Ile Gly Ala Ile Leu Phe Val Ala Gly Ser
                85                  90                  95

Leu Phe Ser Ala Ala Ala Pro Asn Val Glu Val Leu Ile Leu Ser Arg
            100                 105                 110

Val Leu Leu Gly Leu Ala Val Gly Val Ala Ser Tyr Thr Ala Pro Leu
        115                 120                 125

Tyr Leu Ser Glu Ile Ala Pro Glu Lys Ile Arg Gly Ser Met Ile Ser
    130                 135                 140

Met Tyr Gln Leu Met Ile Thr Ile Gly Ile Leu Gly Ala Tyr Leu Ser
145                 150                 155                 160

Asp Thr Ala Phe Ser Tyr Thr Gly Ala Trp Arg Trp Met Leu Gly Val
                165                 170                 175

Ile Ile Ile Pro Ala Ile Leu Leu Ile Gly Val Phe Phe Leu Pro
            180                 185                 190

Asp Ser Pro Arg Trp Phe Ala Ala Lys Arg Arg Phe Val Asp Ala Glu
        195                 200                 205

Arg Val Leu Leu Arg Leu Arg Asp Thr Ser Ala Glu Ala Lys Arg Glu
    210                 215                 220
```

```
Leu Asp Glu Ile Arg Glu Ser Leu Gln Val Lys Gln Ser Gly Trp Ala
225                 230                 235                 240

Leu Phe Lys Glu Asn Ser Asn Phe Arg Arg Ala Val Phe Leu Gly Val
                245                 250                 255

Leu Leu Gln Val Met Gln Gln Phe Thr Gly Met Asn Val Ile Met Tyr
            260                 265                 270

Tyr Ala Pro Lys Ile Phe Glu Leu Ala Gly Tyr Thr Asn Thr Thr Glu
        275                 280                 285

Gln Met Trp Gly Thr Val Ile Val Gly Leu Thr Asn Val Leu Ala Thr
    290                 295                 300

Phe Ile Ala Ile Gly Leu Val Asp Arg Trp Gly Arg Lys Pro Thr Leu
305                 310                 315                 320

Thr Leu Gly Phe Leu Val Met Ala Ala Gly Met Gly Val Leu Gly Thr
                325                 330                 335

Met Met His Ile Gly Ile His Ser Pro Ser Ala Gln Tyr Phe Ala Ile
            340                 345                 350

Ala Met Leu Leu Met Phe Ile Val Gly Phe Ala Met Ser Ala Gly Pro
        355                 360                 365

Leu Ile Trp Val Leu Cys Ser Glu Ile Gln Pro Leu Lys Gly Arg Asp
370                 375                 380

Phe Gly Ile Thr Cys Ser Thr Ala Thr Asn Trp Ile Ala Asn Met Ile
385                 390                 395                 400

Val Gly Ala Thr Phe Leu Thr Met Leu Asn Thr Leu Gly Asn Ala Asn
                405                 410                 415

Thr Phe Trp Val Tyr Ala Ala Leu Asn Val Leu Phe Ile Leu Leu Thr
            420                 425                 430

Leu Trp Leu Val Pro Glu Thr Lys His Val Ser Leu Glu His Ile Glu
        435                 440                 445

Arg Asn Leu Met Lys Gly Arg Lys Leu Arg Glu Ile Gly Ala His Asp
    450                 455                 460
```

<210> SEQ ID NO 11
<211> LENGTH: 473
<212> TYPE: PRT
<213> ORGANISM: Z.mobilis strain ATCC 31821/ZM4/CP4
<220> FEATURE:
<221> NAME/KEY: PEPTIDE
<222> LOCATION: (1)..(473)
<223> OTHER INFORMATION: Protein coded by the gene glf

<400> SEQUENCE: 11

```
Met Ser Ser Glu Ser Ser Gln Gly Leu Val Thr Arg Leu Ala Leu Ile
1               5                   10                  15

Ala Ala Ile Gly Gly Leu Leu Phe Gly Tyr Asp Ser Ala Val Ile Ala
            20                  25                  30

Ala Ile Gly Thr Pro Val Asp Ile His Phe Ile Ala Pro Arg His Leu
        35                  40                  45

Ser Ala Thr Ala Ala Ala Ser Leu Ser Gly Met Val Val Ala Val
    50                  55                  60

Leu Val Gly Cys Val Thr Gly Ser Leu Leu Ser Gly Trp Ile Gly Ile
65                  70                  75                  80

Arg Phe Gly Arg Arg Gly Gly Leu Leu Met Ser Ser Ile Cys Phe Val
                85                  90                  95

Ala Ala Gly Phe Gly Ala Ala Leu Thr Glu Lys Leu Phe Gly Thr Gly
            100                 105                 110
```

```
Gly Ser Ala Leu Gln Ile Phe Cys Phe Phe Arg Phe Leu Ala Gly Leu
            115                 120                 125
Gly Ile Gly Val Val Ser Thr Leu Thr Pro Thr Tyr Ile Ala Glu Ile
130                 135                 140
Ala Pro Pro Asp Lys Arg Gly Gln Met Val Ser Gly Gln Gln Met Ala
145                 150                 155                 160
Ile Val Thr Gly Ala Leu Thr Gly Tyr Ile Phe Thr Trp Leu Leu Ala
                165                 170                 175
His Phe Gly Ser Ile Asp Trp Val Asn Ala Ser Gly Trp Cys Trp Ser
            180                 185                 190
Pro Ala Ser Glu Gly Leu Ile Gly Ile Ala Phe Leu Leu Leu Leu
            195                 200                 205
Thr Ala Pro Asp Thr Pro His Trp Leu Val Met Lys Gly Arg His Ser
210                 215                 220
Glu Ala Ser Lys Ile Leu Ala Arg Leu Glu Pro Gln Ala Asp Pro Asn
225                 230                 235                 240
Leu Thr Ile Gln Lys Ile Lys Ala Gly Phe Asp Lys Ala Met Asp Lys
                245                 250                 255
Ser Ser Ala Gly Leu Phe Ala Phe Gly Ile Thr Val Val Phe Ala Gly
            260                 265                 270
Val Ser Val Ala Ala Phe Gln Gln Leu Val Gly Ile Asn Ala Val Leu
275                 280                 285
Tyr Tyr Ala Pro Gln Met Phe Gln Asn Leu Gly Phe Gly Ala Asp Thr
290                 295                 300
Ala Leu Leu Gln Thr Ile Ser Ile Gly Val Val Asn Phe Ile Phe Thr
305                 310                 315                 320
Met Ile Ala Ser Arg Val Val Asp Arg Phe Gly Arg Lys Pro Leu Leu
                325                 330                 335
Ile Trp Gly Ala Leu Gly Met Ala Ala Met Met Ala Val Leu Gly Cys
            340                 345                 350
Cys Phe Trp Phe Lys Val Gly Gly Val Leu Pro Leu Ala Ser Val Leu
            355                 360                 365
Leu Tyr Ile Ala Val Phe Gly Met Ser Trp Gly Pro Val Cys Trp Val
370                 375                 380
Val Leu Ser Glu Met Phe Pro Ser Ser Ile Lys Gly Ala Ala Met Pro
385                 390                 395                 400
Ile Ala Val Thr Gly Gln Trp Leu Ala Asn Ile Leu Val Asn Phe Leu
                405                 410                 415
Phe Lys Val Ala Asp Gly Ser Pro Ala Leu Asn Gln Thr Phe Asn His
            420                 425                 430
Gly Phe Ser Tyr Leu Val Phe Ala Ala Leu Ser Ile Leu Gly Gly Leu
            435                 440                 445
Ile Val Ala Arg Phe Val Pro Glu Thr Lys Gly Arg Ser Leu Asp Glu
450                 455                 460
Ile Glu Glu Met Trp Arg Ser Gln Lys
465                 470

<210> SEQ ID NO 12
<211> LENGTH: 321
<212> TYPE: PRT
<213> ORGANISM: E.coli strain K12 MG1655
<220> FEATURE:
<221> NAME/KEY: PEPTIDE
<222> LOCATION: (1)..(321)
<223> OTHER INFORMATION: Protein coded by the gene glK
```

<400> SEQUENCE: 12

Met Thr Lys Tyr Ala Leu Val Gly Asp Val Gly Gly Thr Asn Ala Arg
1               5                   10                  15

Leu Ala Leu Cys Asp Ile Ala Ser Gly Glu Ile Ser Gln Ala Lys Thr
            20                  25                  30

Tyr Ser Gly Leu Asp Tyr Pro Ser Leu Glu Ala Val Ile Arg Val Tyr
        35                  40                  45

Leu Glu Glu His Lys Val Glu Val Lys Asp Gly Cys Ile Ala Ile Ala
50                  55                  60

Cys Pro Ile Thr Gly Asp Trp Val Ala Met Thr Asn His Thr Trp Ala
65                  70                  75                  80

Phe Ser Ile Ala Glu Met Lys Lys Asn Leu Gly Phe Ser His Leu Glu
                85                  90                  95

Ile Ile Asn Asp Phe Thr Ala Val Ser Met Ala Ile Pro Met Leu Lys
            100                 105                 110

Lys Glu His Leu Ile Gln Phe Gly Gly Ala Glu Pro Val Glu Gly Lys
        115                 120                 125

Pro Ile Ala Val Tyr Gly Ala Gly Thr Gly Leu Gly Val Ala His Leu
130                 135                 140

Val His Val Asp Lys Arg Trp Val Ser Leu Pro Gly Glu Gly Gly His
145                 150                 155                 160

Val Asp Phe Ala Pro Asn Ser Glu Glu Glu Ala Ile Ile Leu Glu Ile
                165                 170                 175

Leu Arg Ala Glu Ile Gly His Val Ser Ala Glu Arg Val Leu Ser Gly
            180                 185                 190

Pro Gly Leu Val Asn Leu Tyr Arg Ala Ile Val Lys Ala Asp Asn Arg
        195                 200                 205

Leu Pro Glu Asn Leu Lys Pro Lys Asp Ile Thr Glu Arg Ala Leu Ala
210                 215                 220

Asp Ser Cys Thr Asp Cys Arg Arg Ala Leu Ser Leu Phe Cys Val Ile
225                 230                 235                 240

Met Gly Arg Phe Gly Gly Asn Leu Ala Leu Asn Leu Gly Thr Phe Gly
                245                 250                 255

Gly Val Phe Ile Ala Gly Gly Ile Val Pro Arg Phe Leu Glu Phe Phe
            260                 265                 270

Lys Ala Ser Gly Phe Arg Ala Ala Phe Glu Asp Lys Gly Arg Phe Lys
        275                 280                 285

Glu Tyr Val His Asp Ile Pro Val Tyr Leu Ile Val His Asp Asn Pro
290                 295                 300

Gly Leu Leu Gly Ser Gly Ala His Leu Arg Gln Thr Leu Gly His Ile
305                 310                 315                 320

Leu

<210> SEQ ID NO 13
<211> LENGTH: 499
<212> TYPE: PRT
<213> ORGANISM: E.coli strain K12 MG1655
<220> FEATURE:
<221> NAME/KEY: PEPTIDE
<222> LOCATION: (1)..(499)
<223> OTHER INFORMATION: Protein coded by the gene glcD

<400> SEQUENCE: 13

Met Ser Ile Leu Tyr Glu Glu Arg Leu Asp Gly Ala Leu Pro Asp Val
1               5                   10                  15

-continued

```
Asp Arg Thr Ser Val Leu Met Ala Leu Arg Glu His Val Pro Gly Leu
             20                  25                  30
Glu Ile Leu His Thr Asp Glu Glu Ile Ile Pro Tyr Glu Cys Asp Gly
         35                  40                  45
Leu Ser Ala Tyr Arg Thr Arg Pro Leu Leu Val Val Leu Pro Lys Gln
     50                  55                  60
Met Glu Gln Val Thr Ala Ile Leu Ala Val Cys His Arg Leu Arg Val
65                  70                  75                  80
Pro Val Val Thr Arg Gly Ala Gly Thr Gly Leu Ser Gly Gly Ala Leu
                 85                  90                  95
Pro Leu Glu Lys Gly Val Leu Leu Val Met Ala Arg Phe Lys Glu Ile
             100                 105                 110
Leu Asp Ile Asn Pro Val Gly Arg Arg Ala Arg Val Gln Pro Gly Val
         115                 120                 125
Arg Asn Leu Ala Ile Ser Gln Ala Val Ala Pro His Asn Leu Tyr Tyr
     130                 135                 140
Ala Pro Asp Pro Ser Ser Gln Ile Ala Cys Ser Ile Gly Gly Asn Val
145                 150                 155                 160
Ala Glu Asn Ala Gly Gly Val His Cys Leu Lys Tyr Gly Leu Thr Val
                 165                 170                 175
His Asn Leu Leu Lys Ile Glu Val Gln Thr Leu Asp Gly Glu Ala Leu
             180                 185                 190
Thr Leu Gly Ser Asp Ala Leu Asp Ser Pro Gly Phe Asp Leu Leu Ala
         195                 200                 205
Leu Phe Thr Gly Ser Glu Gly Met Leu Gly Val Thr Thr Glu Val Thr
     210                 215                 220
Val Lys Leu Leu Pro Lys Pro Pro Val Ala Arg Val Leu Leu Ala Ser
225                 230                 235                 240
Phe Asp Ser Val Glu Lys Ala Gly Leu Ala Val Gly Asp Ile Ile Ala
                 245                 250                 255
Asn Gly Ile Ile Pro Gly Gly Leu Glu Met Met Asp Asn Leu Ser Ile
             260                 265                 270
Arg Ala Ala Glu Asp Phe Ile His Ala Gly Tyr Pro Val Asp Ala Glu
         275                 280                 285
Ala Ile Leu Leu Cys Glu Leu Asp Gly Val Glu Ser Asp Val Gln Glu
     290                 295                 300
Asp Cys Glu Arg Val Asn Asp Ile Leu Leu Lys Ala Gly Ala Thr Asp
305                 310                 315                 320
Val Arg Leu Ala Gln Asp Glu Ala Glu Arg Val Arg Phe Trp Ala Gly
                 325                 330                 335
Arg Lys Asn Ala Phe Pro Ala Val Gly Arg Ile Ser Pro Asp Tyr Tyr
             340                 345                 350
Cys Met Asp Gly Thr Ile Pro Arg Arg Ala Leu Pro Gly Val Leu Glu
         355                 360                 365
Gly Ile Ala Arg Leu Ser Gln Gln Tyr Asp Leu Arg Val Ala Asn Val
     370                 375                 380
Phe His Ala Gly Asp Gly Asn Met His Pro Leu Ile Leu Phe Asp Ala
385                 390                 395                 400
Asn Glu Pro Gly Glu Phe Ala Arg Ala Glu Glu Leu Gly Lys Ile
                 405                 410                 415
Leu Glu Leu Cys Val Glu Val Gly Gly Ser Ile Ser Gly Glu His Gly
             420                 425                 430
Ile Gly Arg Glu Lys Ile Asn Gln Met Cys Ala Gln Phe Asn Ser Asp
```

```
                    435                 440                 445
Glu Ile Thr Thr Phe His Ala Val Lys Ala Ala Phe Asp Pro Asp Gly
    450                 455                 460

Leu Leu Asn Pro Gly Lys Asn Ile Pro Thr Leu His Arg Cys Ala Glu
465                 470                 475                 480

Phe Gly Ala Met His Val His His Gly His Leu Pro Phe Pro Glu Leu
                    485                 490                 495

Glu Arg Phe

<210> SEQ ID NO 14
<211> LENGTH: 350
<212> TYPE: PRT
<213> ORGANISM: E.coli strain K12 MG1655
<220> FEATURE:
<221> NAME/KEY: PEPTIDE
<222> LOCATION: (1)..(350)
<223> OTHER INFORMATION: Protein coded by the gene glcE

<400> SEQUENCE: 14

Met Leu Arg Glu Cys Asp Tyr Ser Gln Ala Leu Leu Glu Gln Val Asn
1               5                   10                  15

Gln Ala Ile Ser Asp Lys Thr Pro Leu Val Ile Gln Gly Ser Asn Ser
            20                  25                  30

Lys Ala Phe Leu Gly Arg Pro Val Thr Gly Gln Thr Leu Asp Val Arg
        35                  40                  45

Cys His Arg Gly Ile Val Asn Tyr Asp Pro Thr Glu Leu Val Ile Thr
    50                  55                  60

Ala Arg Val Gly Thr Pro Leu Val Thr Ile Glu Ala Ala Leu Glu Ser
65                  70                  75                  80

Ala Gly Gln Met Leu Pro Cys Glu Pro Pro His Tyr Gly Glu Glu Ala
                85                  90                  95

Thr Trp Gly Gly Met Val Ala Cys Gly Leu Ala Gly Pro Arg Arg Pro
            100                 105                 110

Trp Ser Gly Ser Val Arg Asp Phe Val Leu Gly Thr Arg Ile Ile Thr
        115                 120                 125

Gly Ala Gly Lys His Leu Arg Phe Gly Gly Glu Val Met Lys Asn Val
    130                 135                 140

Ala Gly Tyr Asp Leu Ser Arg Leu Met Val Gly Ser Tyr Gly Cys Leu
145                 150                 155                 160

Gly Val Leu Thr Glu Ile Ser Met Lys Val Leu Pro Arg Pro Arg Ala
                165                 170                 175

Ser Leu Ser Leu Arg Arg Glu Ile Ser Leu Gln Glu Ala Met Ser Glu
            180                 185                 190

Ile Ala Glu Trp Gln Leu Gln Pro Leu Pro Ile Ser Gly Leu Cys Tyr
        195                 200                 205

Phe Asp Asn Ala Leu Trp Ile Arg Leu Glu Gly Gly Glu Gly Ser Val
    210                 215                 220

Lys Ala Ala Arg Glu Leu Leu Gly Gly Glu Val Ala Gly Gln Phe
225                 230                 235                 240

Trp Gln Gln Leu Arg Glu Gln Gln Leu Pro Phe Phe Ser Leu Pro Gly
                245                 250                 255

Thr Leu Trp Arg Ile Ser Leu Pro Ser Asp Ala Pro Met Met Asp Leu
            260                 265                 270

Pro Gly Glu Gln Leu Ile Asp Trp Gly Gly Ala Leu Arg Trp Leu Lys
        275                 280                 285
```

```
Ser Thr Ala Glu Asp Asn Gln Ile His Arg Ile Ala Arg Asn Ala Gly
    290                 295                 300

Gly His Ala Thr Arg Phe Ser Ala Gly Asp Gly Phe Ala Pro Leu
305                 310                 315                 320

Ser Ala Pro Leu Phe Arg Tyr His Gln Gln Leu Lys Gln Gln Leu Asp
                325                 330                 335

Pro Cys Gly Val Phe Asn Pro Gly Arg Met Tyr Ala Glu Leu
                340                 345                 350

<210> SEQ ID NO 15
<211> LENGTH: 407
<212> TYPE: PRT
<213> ORGANISM: E.coli strain K12 MG1655
<220> FEATURE:
<221> NAME/KEY: PEPTIDE
<222> LOCATION: (1)..(407)
<223> OTHER INFORMATION: Protein coded by the gene glcF

<400> SEQUENCE: 15

Met Gln Thr Gln Leu Thr Glu Glu Met Arg Gln Asn Ala Arg Ala Leu
1               5                   10                  15

Glu Ala Asp Ser Ile Leu Arg Ala Cys Val His Cys Gly Phe Cys Thr
                20                  25                  30

Ala Thr Cys Pro Thr Tyr Gln Leu Leu Gly Asp Glu Leu Asp Gly Pro
            35                  40                  45

Arg Gly Arg Ile Tyr Leu Ile Lys Gln Val Leu Glu Gly Asn Glu Val
50                  55                  60

Thr Leu Lys Thr Gln Glu His Leu Asp Arg Cys Leu Thr Cys Arg Asn
65                  70                  75                  80

Cys Glu Thr Thr Cys Pro Ser Gly Val Arg Tyr His Asn Leu Leu Asp
                85                  90                  95

Ile Gly Arg Asp Ile Val Glu Gln Lys Val Lys Arg Pro Leu Pro Glu
            100                 105                 110

Arg Ile Leu Arg Glu Gly Leu Arg Gln Val Val Pro Arg Pro Ala Val
            115                 120                 125

Phe Arg Ala Leu Thr Gln Val Gly Leu Val Leu Arg Pro Phe Leu Pro
130                 135                 140

Glu Gln Val Arg Ala Lys Leu Pro Ala Glu Thr Val Lys Ala Lys Pro
145                 150                 155                 160

Arg Pro Pro Leu Arg His Lys Arg Arg Val Leu Met Leu Glu Gly Cys
                165                 170                 175

Ala Gln Pro Thr Leu Ser Pro Asn Thr Asn Ala Ala Thr Ala Arg Val
            180                 185                 190

Leu Asp Arg Leu Gly Ile Ser Val Met Pro Ala Asn Glu Ala Gly Cys
            195                 200                 205

Cys Gly Ala Val Asp Tyr His Leu Asn Ala Gln Glu Lys Gly Leu Ala
210                 215                 220

Arg Ala Arg Asn Asn Ile Asp Ala Trp Trp Pro Ala Ile Glu Ala Gly
225                 230                 235                 240

Ala Glu Ala Ile Leu Gln Thr Ala Ser Gly Cys Gly Ala Phe Val Lys
                245                 250                 255

Glu Tyr Gly Gln Met Leu Lys Asn Asp Ala Leu Tyr Ala Asp Lys Ala
            260                 265                 270

Arg Gln Val Ser Glu Leu Ala Val Asp Leu Val Glu Leu Leu Arg Glu
            275                 280                 285

Glu Pro Leu Glu Lys Leu Ala Ile Arg Gly Asp Lys Lys Leu Ala Phe
```

```
                290                 295                 300

His Cys Pro Cys Thr Leu Gln His Ala Gln Lys Leu Asn Gly Glu Val
305                 310                 315                 320

Glu Lys Val Leu Leu Arg Leu Gly Phe Thr Leu Thr Asp Val Pro Asp
                325                 330                 335

Ser His Leu Cys Cys Gly Ser Ala Gly Thr Tyr Ala Leu Thr His Pro
                340                 345                 350

Asp Leu Ala Arg Gln Leu Arg Asp Asn Lys Met Asn Ala Leu Glu Ser
                355                 360                 365

Gly Lys Pro Glu Met Ile Val Thr Ala Asn Ile Gly Cys Gln Thr His
                370                 375                 380

Leu Ala Ser Ala Gly Arg Thr Ser Val Arg His Trp Ile Glu Ile Val
385                 390                 395                 400

Glu Gln Ala Leu Glu Lys Glu
                405

<210> SEQ ID NO 16
<211> LENGTH: 238
<212> TYPE: PRT
<213> ORGANISM: E.coli strain K12 MG1655
<220> FEATURE:
<221> NAME/KEY: PEPTIDE
<222> LOCATION: (1)..(238)
<223> OTHER INFORMATION: Protein coded by the gene arcA

<400> SEQUENCE: 16

Met Gln Thr Pro His Ile Leu Ile Val Glu Asp Glu Leu Val Thr Arg
1               5                   10                  15

Asn Thr Leu Lys Ser Ile Phe Glu Ala Glu Gly Tyr Asp Val Phe Glu
                20                  25                  30

Ala Thr Asp Gly Ala Glu Met His Gln Ile Leu Ser Glu Tyr Asp Ile
            35                  40                  45

Asn Leu Val Ile Met Asp Ile Asn Leu Pro Gly Lys Asn Gly Leu Leu
        50                  55                  60

Leu Ala Arg Glu Leu Arg Glu Gln Ala Asn Val Ala Leu Met Phe Leu
65                  70                  75                  80

Thr Gly Arg Asp Asn Glu Val Asp Lys Ile Leu Gly Leu Glu Ile Gly
                85                  90                  95

Ala Asp Asp Tyr Ile Thr Lys Pro Phe Asn Pro Arg Glu Leu Thr Ile
            100                 105                 110

Arg Ala Arg Asn Leu Leu Ser Arg Thr Met Asn Leu Gly Thr Val Ser
        115                 120                 125

Glu Glu Arg Arg Ser Val Glu Ser Tyr Lys Phe Asn Gly Trp Glu Leu
    130                 135                 140

Asp Ile Asn Ser Arg Ser Leu Ile Gly Pro Asp Gly Glu Gln Tyr Lys
145                 150                 155                 160

Leu Pro Arg Ser Glu Phe Arg Ala Met Leu His Phe Cys Glu Asn Pro
                165                 170                 175

Gly Lys Ile Gln Ser Arg Ala Glu Leu Leu Lys Lys Met Thr Gly Arg
            180                 185                 190

Glu Leu Lys Pro His Asp Arg Thr Val Asp Val Thr Ile Arg Arg Ile
        195                 200                 205

Arg Lys His Phe Glu Ser Thr Pro Asp Thr Pro Glu Ile Ile Ala Thr
    210                 215                 220

Ile His Gly Glu Gly Tyr Arg Phe Cys Gly Asp Leu Glu Asp
225                 230                 235
```

<210> SEQ ID NO 17
<211> LENGTH: 477
<212> TYPE: PRT
<213> ORGANISM: E.coli strain K12 MG1655
<220> FEATURE:
<221> NAME/KEY: PEPTIDE
<222> LOCATION: (1)..(477)
<223> OTHER INFORMATION: Protein coded by the gene glcA

<400> SEQUENCE: 17

```
Met Phe Lys Asn Ala Phe Ala Asn Leu Gln Lys Val Gly Lys Ser Leu
1               5                   10                  15

Met Leu Pro Val Ser Val Leu Pro Ile Ala Gly Ile Leu Leu Gly Val
            20                  25                  30

Gly Ser Ala Asn Phe Ser Trp Leu Pro Ala Val Val Ser His Val Met
        35                  40                  45

Ala Glu Ala Gly Gly Ser Val Phe Ala Asn Met Pro Leu Ile Phe Ala
    50                  55                  60

Ile Gly Val Ala Leu Gly Phe Thr Asn Asn Asp Gly Val Ser Ala Leu
65                  70                  75                  80

Ala Ala Val Val Ala Tyr Gly Ile Met Val Lys Thr Met Ala Val Val
                85                  90                  95

Ala Pro Leu Val Leu His Leu Pro Ala Glu Glu Ile Ala Ser Lys His
            100                 105                 110

Leu Ala Asp Thr Gly Val Leu Gly Gly Ile Ile Ser Gly Ala Ile Ala
        115                 120                 125

Ala Tyr Met Phe Asn Arg Phe Tyr Arg Ile Lys Leu Pro Glu Tyr Leu
    130                 135                 140

Gly Phe Phe Ala Gly Lys Arg Phe Val Pro Ile Ile Ser Gly Leu Ala
145                 150                 155                 160

Ala Ile Phe Thr Gly Val Val Leu Ser Phe Ile Trp Pro Pro Ile Gly
                165                 170                 175

Ser Ala Ile Gln Thr Phe Ser Gln Trp Ala Ala Tyr Gln Asn Pro Val
            180                 185                 190

Val Ala Phe Gly Ile Tyr Gly Phe Ile Glu Arg Cys Leu Val Pro Phe
        195                 200                 205

Gly Leu His His Ile Trp Asn Val Pro Phe Gln Met Gln Ile Gly Glu
    210                 215                 220

Tyr Thr Asn Ala Ala Gly Gln Val Phe His Gly Asp Ile Pro Arg Tyr
225                 230                 235                 240

Met Ala Gly Asp Pro Thr Ala Gly Lys Leu Ser Gly Gly Phe Leu Phe
                245                 250                 255

Lys Met Tyr Gly Leu Pro Ala Ala Ala Ile Ala Ile Trp His Ser Ala
            260                 265                 270

Lys Pro Glu Asn Arg Ala Lys Val Gly Gly Ile Met Ile Ser Ala Ala
        275                 280                 285

Leu Thr Ser Phe Leu Thr Gly Ile Thr Glu Pro Ile Glu Phe Ser Phe
    290                 295                 300

Met Phe Val Ala Pro Ile Leu Tyr Ile Ile His Ala Ile Leu Ala Gly
305                 310                 315                 320

Leu Ala Phe Pro Ile Cys Ile Leu Leu Gly Met Arg Asp Gly Thr Ser
                325                 330                 335

Phe Ser His Gly Leu Ile Asp Phe Ile Val Leu Ser Gly Asn Ser Ser
            340                 345                 350
```

```
Lys Leu Trp Leu Phe Pro Ile Val Gly Ile Gly Tyr Ala Ile Val Tyr
            355                 360                 365

Tyr Thr Ile Phe Arg Val Leu Ile Lys Ala Leu Asp Leu Lys Thr Pro
        370                 375                 380

Gly Arg Glu Asp Ala Thr Glu Asp Ala Lys Ala Thr Gly Thr Ser Glu
385                 390                 395                 400

Met Ala Pro Ala Leu Val Ala Ala Phe Gly Gly Lys Glu Asn Ile Thr
                405                 410                 415

Asn Leu Asp Ala Cys Ile Thr Arg Leu Arg Val Ser Val Ala Asp Val
                420                 425                 430

Ser Lys Val Asp Gln Ala Gly Leu Lys Lys Leu Gly Ala Ala Gly Val
            435                 440                 445

Val Val Ala Gly Ser Gly Val Gln Ala Ile Phe Gly Thr Lys Ser Asp
    450                 455                 460

Asn Leu Lys Thr Glu Met Asp Glu Tyr Ile Arg Asn His
465                 470                 475

<210> SEQ ID NO 18
<211> LENGTH: 551
<212> TYPE: PRT
<213> ORGANISM: E.coli strain K12 MG1655
<220> FEATURE:
<221> NAME/KEY: PEPTIDE
<222> LOCATION: (1)..(551)
<223> OTHER INFORMATION: Protein coded by the gene lldP

<400> SEQUENCE: 18

Met Asn Leu Trp Gln Gln Asn Tyr Asp Pro Ala Gly Asn Ile Trp Leu
1               5                   10                  15

Ser Ser Leu Ile Ala Ser Leu Pro Ile Leu Phe Phe Phe Ala Leu
            20                  25                  30

Ile Lys Leu Lys Leu Lys Gly Tyr Val Ala Ala Ser Trp Thr Val Ala
            35                  40                  45

Ile Ala Leu Ala Val Ala Leu Leu Phe Tyr Lys Met Pro Val Ala Asn
    50                  55                  60

Ala Leu Ala Ser Val Val Tyr Gly Phe Phe Tyr Gly Leu Trp Pro Ile
65                  70                  75                  80

Ala Trp Ile Ile Ile Ala Ala Val Phe Val Tyr Lys Ile Ser Val Lys
                85                  90                  95

Thr Gly Gln Phe Asp Ile Ile Arg Ser Ser Ile Leu Ser Ile Thr Pro
            100                 105                 110

Asp Gln Arg Leu Gln Met Leu Ile Val Gly Phe Cys Phe Gly Ala Phe
        115                 120                 125

Leu Glu Gly Ala Ala Gly Phe Gly Ala Pro Val Ala Ile Thr Ala Ala
    130                 135                 140

Leu Leu Val Gly Leu Gly Phe Lys Pro Leu Tyr Ala Ala Gly Leu Cys
145                 150                 155                 160

Leu Ile Val Asn Thr Ala Pro Val Ala Phe Gly Ala Met Gly Ile Pro
                165                 170                 175

Ile Leu Val Ala Gly Gln Val Thr Gly Ile Asp Ser Phe Glu Ile Gly
            180                 185                 190

Gln Met Val Gly Arg Gln Leu Pro Phe Met Thr Ile Ile Val Leu Phe
        195                 200                 205

Trp Ile Met Ala Ile Met Asp Gly Trp Arg Gly Ile Lys Glu Thr Trp
    210                 215                 220

Pro Ala Val Val Val Ala Gly Gly Ser Phe Ala Ile Ala Gln Tyr Leu
```

```
            225                 230                 235                 240
    Ser Ser Asn Phe Ile Gly Pro Glu Leu Pro Asp Ile Ile Ser Ser Leu
                    245                 250                 255

Val Ser Leu Leu Cys Leu Thr Leu Phe Leu Lys Arg Trp Gln Pro Val
                    260                 265                 270

Arg Val Phe Arg Phe Gly Asp Leu Gly Ala Ser Gln Val Asp Met Thr
                    275                 280                 285

Leu Ala His Thr Gly Tyr Thr Ala Gly Gln Val Leu Arg Ala Trp Thr
                    290                 295                 300

Pro Phe Leu Phe Leu Thr Ala Thr Val Thr Leu Trp Ser Ile Pro Pro
    305                 310                 315                 320

Phe Lys Ala Leu Phe Ala Ser Gly Gly Ala Leu Tyr Glu Trp Val Ile
                    325                 330                 335

Asn Ile Pro Val Pro Tyr Leu Asp Lys Leu Val Ala Arg Met Pro Pro
                    340                 345                 350

Val Val Ser Glu Ala Thr Ala Tyr Ala Ala Val Phe Lys Phe Asp Trp
                    355                 360                 365

Phe Ser Ala Thr Gly Thr Ala Ile Leu Phe Ala Ala Leu Leu Ser Ile
                    370                 375                 380

Val Trp Leu Lys Met Lys Pro Ser Asp Ala Ile Ser Thr Phe Gly Ser
    385                 390                 395                 400

Thr Leu Lys Glu Leu Ala Leu Pro Ile Tyr Ser Ile Gly Met Val Leu
                    405                 410                 415

Ala Phe Ala Phe Ile Ser Asn Tyr Ser Gly Leu Ser Ser Thr Leu Ala
                    420                 425                 430

Leu Ala Leu Ala His Thr Gly His Ala Phe Thr Phe Phe Ser Pro Phe
                    435                 440                 445

Leu Gly Trp Leu Gly Val Phe Leu Thr Gly Ser Asp Thr Ser Ser Asn
                    450                 455                 460

Ala Leu Phe Ala Ala Leu Gln Ala Thr Ala Ala Gln Gln Ile Gly Val
    465                 470                 475                 480

Ser Asp Leu Leu Leu Val Ala Ala Asn Thr Thr Gly Gly Val Thr Gly
                    485                 490                 495

Lys Met Ile Ser Pro Gln Ser Ile Ala Ile Ala Cys Ala Ala Val Gly
                    500                 505                 510

Leu Val Gly Lys Glu Ser Asp Leu Phe Arg Phe Thr Val Lys His Ser
                    515                 520                 525

Leu Ile Phe Thr Cys Ile Val Gly Val Ile Thr Thr Leu Gln Ala Tyr
                    530                 535                 540

Val Leu Thr Trp Met Ile Pro
    545                 550

<210> SEQ ID NO 19
<211> LENGTH: 549
<212> TYPE: PRT
<213> ORGANISM: E.coli strain K12 MG1655
<220> FEATURE:
<221> NAME/KEY: PEPTIDE
<222> LOCATION: (1)..(549)
<223> OTHER INFORMATION: Protein coded by the gene yjcG

<400> SEQUENCE: 19

Met Lys Arg Val Leu Thr Ala Leu Ala Ala Thr Leu Pro Phe Ala Ala
1               5                   10                  15

Asn Ala Ala Asp Ala Ile Ser Gly Ala Val Glu Arg Gln Pro Thr Asn
                20                  25                  30
```

-continued

```
Trp Gln Ala Ile Ile Met Phe Leu Ile Phe Val Phe Thr Leu Gly
        35                  40                  45
Ile Thr Tyr Trp Ala Ser Lys Arg Val Arg Ser Arg Ser Asp Tyr Tyr
 50                  55                  60
Thr Ala Gly Gly Asn Ile Thr Gly Phe Gln Asn Gly Leu Ala Ile Ala
 65                  70                  75                  80
Gly Asp Tyr Met Ser Ala Ala Ser Phe Leu Gly Ile Ser Ala Leu Val
                 85                  90                  95
Phe Thr Ser Gly Tyr Asp Gly Leu Ile Tyr Ser Leu Gly Phe Leu Val
                100                 105                 110
Gly Trp Pro Ile Ile Leu Phe Leu Ile Ala Glu Arg Leu Arg Asn Leu
            115                 120                 125
Gly Arg Tyr Thr Phe Ala Asp Val Ala Ser Tyr Arg Leu Lys Gln Gly
        130                 135                 140
Pro Ile Arg Ile Leu Ser Ala Cys Gly Ser Leu Val Val Ala Leu
145                 150                 155                 160
Tyr Leu Ile Ala Gln Met Val Gly Ala Gly Lys Leu Ile Glu Leu Leu
                165                 170                 175
Phe Gly Leu Asn Tyr His Ile Ala Val Val Leu Val Gly Val Leu Met
            180                 185                 190
Met Met Tyr Val Leu Phe Gly Gly Met Leu Ala Thr Thr Trp Val Gln
        195                 200                 205
Ile Ile Lys Ala Val Leu Leu Leu Phe Gly Ala Ser Phe Met Ala Phe
210                 215                 220
Met Val Met Lys His Val Gly Phe Ser Phe Asn Asn Leu Phe Ser Glu
225                 230                 235                 240
Ala Met Ala Val His Pro Lys Gly Val Asp Ile Met Lys Pro Gly Gly
                245                 250                 255
Leu Val Lys Asp Pro Ile Ser Ala Leu Ser Leu Gly Leu Gly Leu Met
            260                 265                 270
Phe Gly Thr Ala Gly Leu Pro His Ile Leu Met Arg Phe Phe Thr Val
        275                 280                 285
Ser Asp Ala Arg Glu Ala Arg Lys Ser Val Phe Tyr Ala Thr Gly Phe
290                 295                 300
Met Gly Tyr Phe Tyr Ile Leu Thr Phe Ile Ile Gly Phe Gly Ala Ile
305                 310                 315                 320
Met Leu Val Gly Ala Asn Pro Glu Tyr Lys Asp Ala Ala Gly His Leu
                325                 330                 335
Ile Gly Gly Asn Asn Met Ala Ala Val His Leu Ala Asn Ala Val Gly
            340                 345                 350
Gly Asn Leu Phe Leu Gly Phe Ile Ser Ala Val Ala Phe Ala Thr Ile
        355                 360                 365
Leu Ala Val Val Ala Gly Leu Thr Leu Ala Gly Ala Ser Ala Val Ser
370                 375                 380
His Asp Leu Tyr Ala Asn Val Phe Lys Lys Gly Ala Thr Glu Arg Glu
385                 390                 395                 400
Glu Leu Arg Val Ser Lys Ile Thr Val Leu Ile Leu Gly Val Ile Ala
                405                 410                 415
Ile Ile Leu Gly Val Leu Phe Glu Asn Gln Asn Ile Ala Phe Met Val
            420                 425                 430
Gly Leu Ala Phe Ala Ile Ala Ala Ser Cys Asn Phe Pro Ile Ile Leu
        435                 440                 445
```

-continued

```
Leu Ser Met Tyr Trp Ser Lys Leu Thr Thr Arg Gly Ala Met Met Gly
    450                 455                 460

Gly Trp Leu Gly Leu Ile Thr Ala Val Val Leu Met Ile Leu Gly Pro
465                 470                 475                 480

Thr Ile Trp Val Gln Ile Leu Gly His Glu Lys Ala Ile Phe Pro Tyr
                485                 490                 495

Glu Tyr Pro Ala Leu Phe Ser Ile Thr Val Ala Phe Leu Gly Ile Trp
            500                 505                 510

Phe Phe Ser Ala Thr Asp Asn Ser Ala Glu Gly Ala Arg Glu Arg Glu
        515                 520                 525

Leu Phe Arg Ala Gln Phe Ile Arg Ser Gln Thr Gly Phe Gly Val Glu
530                 535                 540

Gln Gly Arg Ala His
545

<210> SEQ ID NO 20
<211> LENGTH: 152
<212> TYPE: PRT
<213> ORGANISM: E.coli strain K12 MG1655
<220> FEATURE:
<221> NAME/KEY: PEPTIDE
<222> LOCATION: (1)..(152)
<223> OTHER INFORMATION: Protein coded by the gene mgsA

<400> SEQUENCE: 20

Met Glu Leu Thr Thr Arg Thr Leu Pro Ala Arg Lys His Ile Ala Leu
1               5                   10                  15

Val Ala His Asp His Cys Lys Gln Met Leu Met Ser Trp Val Glu Arg
            20                  25                  30

His Gln Pro Leu Leu Glu Gln His Val Leu Tyr Ala Thr Gly Thr Thr
        35                  40                  45

Gly Asn Leu Ile Ser Arg Ala Thr Gly Met Asn Val Asn Ala Met Leu
    50                  55                  60

Ser Gly Pro Met Gly Gly Asp Gln Gln Val Gly Ala Leu Ile Ser Glu
65                  70                  75                  80

Gly Lys Ile Asp Val Leu Ile Phe Phe Trp Asp Pro Leu Asn Ala Val
                85                  90                  95

Pro His Asp Pro Asp Val Lys Ala Leu Leu Arg Leu Ala Thr Val Trp
            100                 105                 110

Asn Ile Pro Val Ala Thr Asn Val Ala Thr Ala Asp Phe Ile Ile Gln
        115                 120                 125

Ser Pro His Phe Asn Asp Ala Val Asp Ile Leu Ile Pro Asp Tyr Gln
    130                 135                 140

Arg Tyr Leu Ala Asp Arg Leu Lys
145                 150

<210> SEQ ID NO 21
<211> LENGTH: 320
<212> TYPE: PRT
<213> ORGANISM: E.coli strain K12 MG1655
<220> FEATURE:
<221> NAME/KEY: PEPTIDE
<222> LOCATION: (1)..(320)
<223> OTHER INFORMATION: Protein coded by the gene pfKA

<400> SEQUENCE: 21

Met Ile Lys Lys Ile Gly Val Leu Thr Ser Gly Gly Asp Ala Pro Gly
1               5                   10                  15

Met Asn Ala Ala Ile Arg Gly Val Val Arg Ser Ala Leu Thr Glu Gly
```

```
                    20                  25                  30

Leu Glu Val Met Gly Ile Tyr Asp Gly Tyr Leu Gly Leu Tyr Glu Asp
                35                  40                  45

Arg Met Val Gln Leu Asp Arg Tyr Ser Val Ser Asp Met Ile Asn Arg
 50                  55                  60

Gly Gly Thr Phe Leu Gly Ser Ala Arg Phe Pro Glu Phe Arg Asp Glu
 65                  70                  75                  80

Asn Ile Arg Ala Val Ala Ile Glu Asn Leu Lys Lys Arg Gly Ile Asp
                85                  90                  95

Ala Leu Val Val Ile Gly Gly Asp Gly Ser Tyr Met Gly Ala Met Arg
                100                 105                 110

Leu Thr Glu Met Gly Phe Pro Cys Ile Gly Leu Pro Gly Thr Ile Asp
                115                 120                 125

Asn Asp Ile Lys Gly Thr Asp Tyr Thr Ile Gly Phe Phe Thr Ala Leu
                130                 135                 140

Ser Thr Val Val Glu Ala Ile Asp Arg Leu Arg Asp Thr Ser Ser Ser
145                 150                 155                 160

His Gln Arg Ile Ser Val Val Glu Val Met Gly Arg Tyr Cys Gly Asp
                165                 170                 175

Leu Thr Leu Ala Ala Ala Ile Ala Gly Gly Cys Glu Phe Val Val Val
                180                 185                 190

Pro Glu Val Glu Phe Ser Arg Glu Asp Leu Val Asn Glu Ile Lys Ala
                195                 200                 205

Gly Ile Ala Lys Gly Lys Lys His Ala Ile Val Ala Ile Thr Glu His
                210                 215                 220

Met Cys Asp Val Asp Glu Leu Ala His Phe Ile Glu Lys Glu Thr Gly
225                 230                 235                 240

Arg Glu Thr Arg Ala Thr Val Leu Gly His Ile Gln Arg Gly Gly Ser
                245                 250                 255

Pro Val Pro Tyr Asp Arg Ile Leu Ala Ser Arg Met Gly Ala Tyr Ala
                260                 265                 270

Ile Asp Leu Leu Leu Ala Gly Tyr Gly Gly Arg Cys Val Gly Ile Gln
                275                 280                 285

Asn Glu Gln Leu Val His His Asp Ile Ile Asp Ala Ile Glu Asn Met
                290                 295                 300

Lys Arg Pro Phe Lys Gly Asp Trp Leu Asp Cys Ala Lys Lys Leu Tyr
305                 310                 315                 320

<210> SEQ ID NO 22
<211> LENGTH: 215
<212> TYPE: PRT
<213> ORGANISM: E.coli strain K12 MG1655
<220> FEATURE:
<221> NAME/KEY: PEPTIDE
<222> LOCATION: (1)..(215)
<223> OTHER INFORMATION: Protein coded by the gene fucA

<400> SEQUENCE: 22

Met Glu Arg Asn Lys Leu Ala Arg Gln Ile Ile Asp Thr Cys Leu Glu
1               5                   10                  15

Met Thr Arg Leu Gly Leu Asn Gln Gly Thr Ala Gly Asn Val Ser Val
                20                  25                  30

Arg Tyr Gln Asp Gly Met Leu Ile Thr Pro Thr Gly Ile Pro Tyr Glu
                35                  40                  45

Lys Leu Thr Glu Ser His Ile Val Phe Ile Asp Gly Asn Gly Lys His
 50                  55                  60
```

-continued

```
Glu Gly Lys Leu Pro Ser Ser Glu Trp Arg Phe His Met Ala Ala
 65                  70                  75                  80

Tyr Gln Ser Arg Pro Asp Ala Asn Ala Val His Asn His Ala Val
                 85                  90                  95

His Cys Thr Ala Val Ser Ile Leu Asn Arg Ser Ile Pro Ala Ile His
            100                 105                 110

Tyr Met Ile Ala Ala Gly Gly Asn Ser Ile Pro Cys Ala Pro Tyr
        115                 120                 125

Ala Thr Phe Gly Thr Arg Glu Leu Ser Glu His Val Ala Leu Ala Leu
130                 135                 140

Lys Asn Arg Lys Ala Thr Leu Leu Gln His His Gly Leu Ile Ala Cys
145                 150                 155                 160

Glu Val Asn Leu Glu Lys Ala Leu Trp Leu Ala His Glu Val Glu Val
                165                 170                 175

Leu Ala Gln Leu Tyr Leu Thr Thr Leu Ala Ile Thr Asp Pro Val Pro
            180                 185                 190

Val Leu Ser Asp Glu Glu Ile Ala Val Val Leu Glu Lys Phe Lys Thr
        195                 200                 205

Tyr Gly Leu Arg Ile Glu Glu
    210                 215

<210> SEQ ID NO 23
<211> LENGTH: 491
<212> TYPE: PRT
<213> ORGANISM: E.coli strain K12 MG1655
<220> FEATURE:
<221> NAME/KEY: PEPTIDE
<222> LOCATION: (1)..(491)
<223> OTHER INFORMATION: Protein coded by the gene zwf

<400> SEQUENCE: 23

Met Ala Val Thr Gln Thr Ala Gln Ala Cys Asp Leu Val Ile Phe Gly
  1               5                  10                  15

Ala Lys Gly Asp Leu Ala Arg Arg Lys Leu Leu Pro Ser Leu Tyr Gln
             20                  25                  30

Leu Glu Lys Ala Gly Gln Leu Asn Pro Asp Thr Arg Ile Ile Gly Val
         35                  40                  45

Gly Arg Ala Asp Trp Asp Lys Ala Ala Tyr Thr Lys Val Val Arg Glu
 50                  55                  60

Ala Leu Glu Thr Phe Met Lys Glu Thr Ile Asp Glu Gly Leu Trp Asp
 65                  70                  75                  80

Thr Leu Ser Ala Arg Leu Asp Phe Cys Asn Leu Asp Val Asn Asp Thr
                 85                  90                  95

Ala Ala Phe Ser Arg Leu Gly Ala Met Leu Asp Gln Lys Asn Arg Ile
            100                 105                 110

Thr Ile Asn Tyr Phe Ala Met Pro Pro Ser Thr Phe Gly Ala Ile Cys
        115                 120                 125

Lys Gly Leu Gly Glu Ala Lys Leu Asn Ala Lys Pro Ala Arg Val Val
130                 135                 140

Met Glu Lys Pro Leu Gly Thr Ser Leu Ala Thr Ser Gln Glu Ile Asn
145                 150                 155                 160

Asp Gln Val Gly Glu Tyr Phe Glu Glu Cys Gln Val Tyr Arg Ile Asp
                165                 170                 175

His Tyr Leu Gly Lys Glu Thr Val Leu Asn Leu Leu Ala Leu Arg Phe
            180                 185                 190
```

Ala Asn Ser Leu Phe Val Asn Trp Asp Asn Arg Thr Ile Asp His
        195                 200                 205

Val Glu Ile Thr Val Ala Glu Glu Val Gly Ile Glu Gly Arg Trp Gly
    210                 215                 220

Tyr Phe Asp Lys Ala Gly Gln Met Arg Asp Met Ile Gln Asn His Leu
225                 230                 235                 240

Leu Gln Ile Leu Cys Met Ile Ala Met Ser Pro Pro Ser Asp Leu Ser
                245                 250                 255

Ala Asp Ser Ile Arg Asp Glu Lys Val Lys Val Leu Lys Ser Leu Arg
                260                 265                 270

Arg Ile Asp Arg Ser Asn Val Arg Glu Lys Thr Val Arg Gly Gln Tyr
            275                 280                 285

Thr Ala Gly Phe Ala Gln Gly Lys Lys Val Pro Gly Tyr Leu Glu Glu
        290                 295                 300

Glu Gly Ala Asn Lys Ser Ser Asn Thr Glu Thr Phe Val Ala Ile Arg
305                 310                 315                 320

Val Asp Ile Asp Asn Trp Arg Trp Ala Gly Val Pro Phe Tyr Leu Arg
                325                 330                 335

Thr Gly Lys Arg Leu Pro Thr Lys Cys Ser Glu Val Val Val Tyr Phe
            340                 345                 350

Lys Thr Pro Glu Leu Asn Leu Phe Lys Glu Ser Trp Gln Asp Leu Pro
        355                 360                 365

Gln Asn Lys Leu Thr Ile Arg Leu Gln Pro Asp Glu Gly Val Asp Ile
    370                 375                 380

Gln Val Leu Asn Lys Val Pro Gly Leu Asp His Lys His Asn Leu Gln
385                 390                 395                 400

Ile Thr Lys Leu Asp Leu Ser Tyr Ser Glu Thr Phe Asn Gln Thr His
                405                 410                 415

Leu Ala Asp Ala Tyr Glu Arg Leu Leu Leu Glu Thr Met Arg Gly Ile
            420                 425                 430

Gln Ala Leu Phe Val Arg Arg Asp Glu Val Glu Ala Trp Lys Trp
        435                 440                 445

Val Asp Ser Ile Thr Glu Ala Trp Ala Met Asp Asn Asp Ala Pro Lys
450                 455                 460

Pro Tyr Gln Ala Gly Thr Trp Gly Pro Val Ala Ser Val Ala Met Ile
465                 470                 475                 480

Thr Arg Asp Gly Arg Ser Trp Asn Glu Phe Glu
                485                 490

<210> SEQ ID NO 24
<211> LENGTH: 603
<212> TYPE: PRT
<213> ORGANISM: E.coli strain K12 MG1655
<220> FEATURE:
<221> NAME/KEY: PEPTIDE
<222> LOCATION: (1)..(603)
<223> OTHER INFORMATION: Protein coded by the gene edd

<400> SEQUENCE: 24

Met Asn Pro Gln Leu Leu Arg Val Thr Asn Arg Ile Ile Glu Arg Ser
1               5                   10                  15

Arg Glu Thr Arg Ser Ala Tyr Leu Ala Arg Ile Glu Gln Ala Lys Thr
            20                  25                  30

Ser Thr Val His Arg Ser Gln Leu Ala Cys Gly Asn Leu Ala His Gly
        35                  40                  45

Phe Ala Ala Cys Gln Pro Glu Asp Lys Ala Ser Leu Lys Ser Met Leu

```
                50              55              60
Arg Asn Asn Ile Ala Ile Ile Thr Ser Tyr Asn Asp Met Leu Ser Ala
 65              70              75              80

His Gln Pro Tyr Glu His Tyr Pro Glu Ile Ile Arg Lys Ala Leu His
                 85              90              95

Glu Ala Asn Ala Val Gly Gln Val Ala Gly Gly Val Pro Ala Met Cys
                100             105             110

Asp Gly Val Thr Gln Gly Gln Asp Gly Met Glu Leu Ser Leu Leu Ser
                115             120             125

Arg Glu Val Ile Ala Met Ser Ala Ala Val Gly Leu Ser His Asn Met
130             135             140

Phe Asp Gly Ala Leu Phe Leu Gly Val Cys Asp Lys Ile Val Pro Gly
145             150             155             160

Leu Thr Met Ala Ala Leu Ser Phe Gly His Leu Pro Ala Val Phe Val
                165             170             175

Pro Ser Gly Pro Met Ala Ser Gly Leu Pro Asn Lys Glu Lys Val Arg
                180             185             190

Ile Arg Gln Leu Tyr Ala Glu Gly Lys Val Asp Arg Met Ala Leu Leu
                195             200             205

Glu Ser Glu Ala Ala Ser Tyr His Ala Pro Gly Thr Cys Thr Phe Tyr
210             215             220

Gly Thr Ala Asn Thr Asn Gln Met Val Val Glu Phe Met Gly Met Gln
225             230             235             240

Leu Pro Gly Ser Ser Phe Val His Pro Asp Ser Pro Leu Arg Asp Ala
                245             250             255

Leu Thr Ala Ala Ala Arg Gln Val Thr Arg Met Thr Gly Asn Gly
                260             265             270

Asn Glu Trp Met Pro Ile Gly Lys Met Ile Asp Glu Lys Val Val Val
                275             280             285

Asn Gly Ile Val Ala Leu Leu Ala Thr Gly Gly Ser Thr Asn His Thr
290             295             300

Met His Leu Val Ala Met Ala Arg Ala Ala Gly Ile Gln Ile Asn Trp
305             310             315             320

Asp Asp Phe Ser Asp Leu Ser Asp Val Val Pro Leu Met Ala Arg Leu
                325             330             335

Tyr Pro Asn Gly Pro Ala Asp Ile Asn His Phe Gln Ala Ala Gly Gly
                340             345             350

Val Pro Val Leu Val Arg Glu Leu Leu Lys Ala Gly Leu Leu His Glu
                355             360             365

Asp Val Asn Thr Val Ala Gly Phe Gly Leu Ser Arg Tyr Thr Leu Glu
370             375             380

Pro Trp Leu Asn Asn Gly Glu Leu Asp Trp Arg Glu Gly Ala Glu Lys
385             390             395             400

Ser Leu Asp Ser Asn Val Ile Ala Ser Phe Glu Gln Pro Phe Ser His
                405             410             415

His Gly Gly Thr Lys Val Leu Ser Gly Asn Leu Gly Arg Ala Val Met
                420             425             430

Lys Thr Ser Ala Val Pro Val Glu Asn Gln Val Ile Glu Ala Pro Ala
                435             440             445

Val Val Phe Glu Ser Gln His Asp Val Met Pro Ala Phe Glu Ala Gly
                450             455             460

Leu Leu Asp Arg Asp Cys Val Val Val Arg His Gln Gly Pro Lys
465             470             475             480
```

-continued

Ala Asn Gly Met Pro Glu Leu His Lys Leu Met Pro Pro Leu Gly Val
            485                 490                 495

Leu Leu Asp Arg Cys Phe Lys Ile Ala Leu Val Thr Asp Gly Arg Leu
        500                 505                 510

Ser Gly Ala Ser Gly Lys Val Pro Ser Ala Ile His Val Thr Pro Glu
    515                 520                 525

Ala Tyr Asp Gly Gly Leu Leu Ala Lys Val Arg Asp Gly Asp Ile Ile
530                 535                 540

Arg Val Asn Gly Gln Thr Gly Glu Leu Thr Leu Leu Val Asp Glu Ala
545                 550                 555                 560

Glu Leu Ala Ala Arg Glu Pro His Ile Pro Asp Leu Ser Ala Ser Arg
                565                 570                 575

Val Gly Thr Gly Arg Glu Leu Phe Ser Ala Leu Arg Glu Lys Leu Ser
            580                 585                 590

Gly Ala Glu Gln Gly Ala Thr Cys Ile Thr Phe
            595                 600

<210> SEQ ID NO 25
<211> LENGTH: 213
<212> TYPE: PRT
<213> ORGANISM: E.coli strain K12 MG1655
<220> FEATURE:
<221> NAME/KEY: PEPTIDE
<222> LOCATION: (1)..(213)
<223> OTHER INFORMATION: Protein coded by the gene eda

<400> SEQUENCE: 25

Met Lys Asn Trp Lys Thr Ser Ala Glu Ser Ile Leu Thr Thr Gly Pro
1               5                   10                  15

Val Val Pro Val Ile Val Lys Lys Leu Glu His Ala Val Pro Met
            20                  25                  30

Ala Lys Ala Leu Val Ala Gly Gly Val Arg Val Leu Glu Val Thr Leu
        35                  40                  45

Arg Thr Glu Cys Ala Val Asp Ala Ile Arg Ala Ile Ala Lys Glu Val
    50                  55                  60

Pro Glu Ala Ile Val Gly Ala Gly Thr Val Leu Asn Pro Gln Gln Leu
65                  70                  75                  80

Ala Glu Val Thr Glu Ala Gly Ala Gln Phe Ala Ile Ser Pro Gly Leu
                85                  90                  95

Thr Glu Pro Leu Leu Lys Ala Ala Thr Glu Gly Thr Ile Pro Leu Ile
            100                 105                 110

Pro Gly Ile Ser Thr Val Ser Glu Leu Met Leu Gly Met Asp Tyr Gly
        115                 120                 125

Leu Lys Glu Phe Lys Phe Pro Ala Glu Ala Asn Gly Gly Val Lys
    130                 135                 140

Ala Leu Gln Ala Ile Ala Gly Pro Phe Ser Gln Val Arg Phe Cys Pro
145                 150                 155                 160

Thr Gly Gly Ile Ser Pro Ala Asn Tyr Arg Asp Tyr Leu Ala Leu Lys
                165                 170                 175

Ser Val Leu Cys Ile Gly Gly Ser Trp Leu Val Pro Ala Asp Ala Leu
            180                 185                 190

Glu Ala Gly Asp Tyr Asp Arg Ile Thr Lys Leu Ala Arg Glu Ala Val
        195                 200                 205

Glu Gly Ala Lys Leu
    210

<210> SEQ ID NO 26
<211> LENGTH: 39
<212> TYPE: DNA
<213> ORGANISM: Artificial Sequence
<220> FEATURE:
<223> OTHER INFORMATION: Sense primer for gene xylA

<400> SEQUENCE: 26
ctggtgccgc gcggcagcca tatgcaagcc tattttgac                                39

<210> SEQ ID NO 27
<211> LENGTH: 42
<212> TYPE: DNA
<213> ORGANISM: Artificial Sequence
<220> FEATURE:
<223> OTHER INFORMATION: Antisense primer for gene xylA

<400> SEQUENCE: 27
gtcgacggag ctcgaattcg ttatttgtcg aacagataat gg                            42

<210> SEQ ID NO 28
<211> LENGTH: 43
<212> TYPE: DNA
<213> ORGANISM: Artificial Sequence
<220> FEATURE:
<223> OTHER INFORMATION: Sense primer for gene xylB

<400> SEQUENCE: 28
ctggtgccgc gcggcagcca tatgtatatc gggatagatc ttg                           43

<210> SEQ ID NO 29
<211> LENGTH: 38
<212> TYPE: DNA
<213> ORGANISM: Artificial Sequence
<220> FEATURE:
<223> OTHER INFORMATION: Antisense primer for gene xylB

<400> SEQUENCE: 29
gtcgacggag ctcgaattcg ttacgccatt aatggcag                                 38

<210> SEQ ID NO 30
<211> LENGTH: 46
<212> TYPE: DNA
<213> ORGANISM: Artificial Sequence
<220> FEATURE:
<223> OTHER INFORMATION: Sense primer for gene araA

<400> SEQUENCE: 30
ctggtgccgc gcggcagcca tatgacgatt tttgataatt atgaag                        46

<210> SEQ ID NO 31
<211> LENGTH: 42
<212> TYPE: DNA
<213> ORGANISM: Artificial Sequence
<220> FEATURE:
<223> OTHER INFORMATION: Antisense primer for gene araA

<400> SEQUENCE: 31
gtcgacggag ctcgaattcg ttagcgacga aacccgtaat ac                            42

<210> SEQ ID NO 32
<211> LENGTH: 38
<212> TYPE: DNA
<213> ORGANISM: Artificial Sequence
<220> FEATURE:
<223> OTHER INFORMATION: Sense primer for gene araB

<400> SEQUENCE: 32
ctggtgccgc gcggcagcca tatggcgatt gcaattgg         38

<210> SEQ ID NO 33
<211> LENGTH: 39
<212> TYPE: DNA
<213> ORGANISM: Artificial Sequence
<220> FEATURE:
<223> OTHER INFORMATION: Antisense primer for gene araB

<400> SEQUENCE: 33
gtcgacggag ctcgaattcg ttatagagtc gcaacggcc         39

<210> SEQ ID NO 34
<211> LENGTH: 41
<212> TYPE: DNA
<213> ORGANISM: Artificial Sequence
<220> FEATURE:
<223> OTHER INFORMATION: Sense primer for gene araD

<400> SEQUENCE: 34
ctggtgccgc gcggcagcca tatgttagaa gatctcaaac g         41

<210> SEQ ID NO 35
<211> LENGTH: 38
<212> TYPE: DNA
<213> ORGANISM: Artificial Sequence
<220> FEATURE:
<223> OTHER INFORMATION: Antisense primer for gene araD

<400> SEQUENCE: 35
gtcgacggag ctcgaattcg ttactgcccg taatatgc         38

<210> SEQ ID NO 36
<211> LENGTH: 41
<212> TYPE: DNA
<213> ORGANISM: Artificial Sequence
<220> FEATURE:
<223> OTHER INFORMATION: Sense primer for gene rpe

<400> SEQUENCE: 36
ctggtgccgc gcggcagcca tatgaaacag tatttgattg c         41

<210> SEQ ID NO 37
<211> LENGTH: 41
<212> TYPE: DNA
<213> ORGANISM: Artificial Sequence
<220> FEATURE:
<223> OTHER INFORMATION: Antisense primer for gene rpe

<400> SEQUENCE: 37
gtcgacggag ctcgaattcg ttattcatga cttacctttg c         41

<210> SEQ ID NO 38
<211> LENGTH: 37
<212> TYPE: DNA
<213> ORGANISM: Artificial Sequence
<220> FEATURE:
<223> OTHER INFORMATION: Sense primer for gene kdsD

<400> SEQUENCE: 38
gccgcgcggc agccatatat gtcgcacgta gagttac         37

<210> SEQ ID NO 39

```
<211> LENGTH: 38
<212> TYPE: DNA
<213> ORGANISM: Artificial Sequence
<220> FEATURE:
<223> OTHER INFORMATION: Antisense primer for gene kdsD

<400> SEQUENCE: 39
gtcgacggag ctcgaattcg ttacactacg cctgcacg                              38

<210> SEQ ID NO 40
<211> LENGTH: 41
<212> TYPE: DNA
<213> ORGANISM: Artificial Sequence
<220> FEATURE:
<223> OTHER INFORMATION: Sense primer for gene fsa

<400> SEQUENCE: 40
gccgcgcggc agccatatat ggaactgtat ctggatactt c                          41

<210> SEQ ID NO 41
<211> LENGTH: 38
<212> TYPE: DNA
<213> ORGANISM: Artificial Sequence
<220> FEATURE:
<223> OTHER INFORMATION: Antisense primer for gene fsa

<400> SEQUENCE: 41
gtcgacggag ctcgaattcg ttaaatcgac gttctgcc                              38

<210> SEQ ID NO 42
<211> LENGTH: 40
<212> TYPE: DNA
<213> ORGANISM: Artificial Sequence
<220> FEATURE:
<223> OTHER INFORMATION: Sense primer for gene aldA

<400> SEQUENCE: 42
ctggtgccgc gcggcagcca tatgtcagta cccgttcaac                            40

<210> SEQ ID NO 43
<211> LENGTH: 42
<212> TYPE: DNA
<213> ORGANISM: Artificial Sequence
<220> FEATURE:
<223> OTHER INFORMATION: Antisense primer for gene aldA

<400> SEQUENCE: 43
gtcgacggag ctcgaattcg ttaagactgt aaataaacca cc                         42
```

MICROORGANISMS AND PROCESS FOR PRODUCING GLYCOLIC ACID FROM PENTOSES AND HEXOSES

CROSS-REFERENCE TO RELATED APPLICATIONS

This application is a national stage entry of PCT/FR2019/051760 filed Jul. 12, 2019, which claims the benefit of FR 1856511 filed Jul. 13, 2018.

REFERENCE TO SEQUENCE LISTING

This application includes an electronic sequence listing in a file named 553826SEQLST.TXT, created on Jan. 8, 2021 and containing 86,557 bytes, which is hereby incorporated by reference in its entirety for all purposes.

TECHNICAL FIELD

The present invention relates to the technical field of bioconversion of a carbon source into at least one metabolite of interest and in particular into glycolic acid.

More particularly, the present invention relates to a microorganism the central carbon metabolism of which has been rearranged so as to convert hexoses and pentoses, from a carbon source and, in particular, plant biomass into glycolic acid. The present invention is also concerned with a process for producing glycolic acid from hexoses and pentoses contained in plant biomass implementing such a microorganism.

STATE OF PRIOR ART

Glycolic acid or hydroxyacetic acid having the formula $HO-CH_2-C(=O)-OH$ finds many applications in different fields. Indeed, by way of illustrating purposes, it can be used as a pH regulating agent or keratolytic agent in cosmetics and pharmaceutics, as a dyeing and tanning agent in the textile industry or even as a disinfectant in the agro-food industry. Glycolic acid also enables polymers such as thermoplastic resins comprising poly(glycolic acid) to be produced. Such polymers exhibit outstanding gas barrier properties and have the capability of being hydrolysed in aqueous environments gradually and controllably, making these polymers good candidates for packaging materials or resorbable materials useful in the biomedical field.

Even if glycolic acid can be obtained from sugar cane, beet or grape extracts, its industrial scale production comes from chemical synthesis. Several of these syntheses use, as a starting reagent, formaldehyde which is an irritant and carcinogenic compound, which precludes any trace of this substance in preparations having a Marketing Authorisation.

Consequently, bio-sourced glycolic acid has an interest in pharmaceutical, cosmetic but also textile fields. Under a polymerised form, poly(glycolic acid) and polymers containing poly(glycolic acid) could represent a new generation of packaging bio-plastics and bio-resorbable polymers [1]. That is why for a few years, several research teams have been interested in its production by the microbial pathway.

Glycolic acid can be naturally produced in small amounts via the reduction of glyoxylate in bacteria and moulds, including yeast [2]. The former engineering projects have been inspired by the natural metabolism. The maximum theoretical yield which can be reached by this natural pathway is 2 moles glycolic acid (GA) per mole of hexose and 1.66 mole per mole of pentoses (or 0.84 g GA/g sugar).

Thus, a process for the bioproduction of glycolic acid based on the improvement of the natural metabolism in *Escherichia coli* has been the object of the international application WO 2007/141316 [3]. This pathway is called, in the following, "glyoxylate shunt (GS) pathway". In the process described, the reactions consuming glyoxylate and the enzymes metabolising glycolate have been deleted, whereas NADPH glyoxylate reductase which converts glyoxylate into glycolate has been overexpressed in order to increase the glycolic acid yield. The regulation system of the glyoxylate cycle has also been modified to remove inhibitions and increase the carbon flow to glyoxylate. From the work described in [3], other modifications have been provided to improve glycolic acid production from (D)-glucose, which enabled 92.9% of the maximum theoretical yield to be reached [4].

However, from the stoichiometric point of view, this synthetic pathway is not optimal, the theoretical yield is limited by the carbon loss due to decarboxylation of pyruvate into acetyl-CoA. In this context, the substitution and/or complementation of the natural metabolism by a synthetic pathway for sugar assimilation and glycolic acid production is a contemplatable strategy to remove this limitation.

For that purpose, a semi-synthetic pathway for pentose assimilation has been described in the international application WO 2017/059236 [5]. This pathway involves phosphorylation in position 1 of the (D)-ribulose or (L)-xylulose ring and is called, in the following, "ribulose-1-P pathway". This synthetic pathway allows pentose assimilation, more particularly (D)-xylose assimilation which is the majority pentose of hemicellulose. The (D)-xylose yield is 0.44 g/g [6]. It is however to be noted that the pathway described in international application WO 2017/059236 [5] requires, to be functional, reducing or inactivating the xylulokinase activity and overexpressing the following four enzymes: an epimerase which interconverts xylulose and ribulose, a (D)-ribulose-phosphate aldolase, a D-ribulokinase and a glycolaldehyde dehydrogenase.

Another synthetic pathway for glycolic acid production has been developed and been the object of the international application WO 2016/079440 [7]. This synthetic pathway phosphorylates pentose sugars on the first carbon (C1) instead of the carbon 5 (C5) as is the case in the pentose phosphate pathway. This phosphorylation reaction catalysed by a heterologous ketohexokinase, from mammals, is followed by a cleavage reaction by an aldolase leading to a C3 molecule (dihydroxyacetone-P) and a C2 molecule (glycolaldehyde). The latter through an oxidation reaction catalysed by a glycoladehyde dehydrogenase leads to glycolic acid synthesis or through a reduction reaction catalysed by an endogenous reductase to ethylene glycol. This synthetic pathway, called in the following "xylulose-1-P pathway" involves three different enzymes and not five as in [5] and enables a molar theoretical production in glycolic acid and ethylene glycol (1 mole per mole of pentose sugars) to be achieved.

It should be noticed that the synthetic pathways independent of the glyoxylate pathway described in [5] and [7] do not have a decarboxylation step and thus $CO_2$ loss but both of them generate a C3 compound, that is dihydroxyacetone phosphate (DHAP), which limits the maximum theoretical yield in glycolic acid.

Thus, in order to be able to use DHAP for glycolic acid production, the synthetic pathways described in [5] and [7] have been coupled with the optimised natural pathway described in [3]. The combination of the pathways described in [7] and [3] resulted in a yield of 0.63 g glycolic acid per g of sugars but the maximum theoretical yield is still limited because of the $CO_2$ loss, a consequence of the use of the optimised natural pathway [8].

In a correspondence addressed to Nature Biotechnology [9], Dugar and Stephanopolous have introduced the notion of "maximum energy yield ($Y^E$)". This yield is purely calculated based on the energy balance between the substrate and the product, which is practically reflected by taking the redox state of the substrate and of the product into account. Thus, $Y^E$ is determined by the ratio $\gamma_s/\gamma_p$ where $\gamma_s$ and $\gamma_p$ are the reduction degrees of the substrate and of the product. For example, the reduction degree of glucose $\gamma_s$ is equal to 24 whereas that of the product ethanol $\gamma_p$ is equal to 12. Thus, $Y^E$ is 2. On the other hand, the yield of the metabolic pathway ($Y^P$) depends on the pathway or the metabolic network and it is calculated from the stoichiometry of the pathway considered. Thus, for the case of fermentation of glucose into ethanol, $Y^P$ is 2 and it is found that $Y^E$ is $Y^P$. This equality is not found for all the cases. For example, the conversion of glucose into acetate results in a yield $Y^P$ of 2 but the maximum energy yield $Y^E$ is 3. Thus, there is a potential material loss of 33% which is explained by the natural metabolic pathway. However, the Liao et al team has shown that it is possible to construct viable metabolic pathways leading to the production of 3 moles of acetate per mole of glucose [10]. According to the same principle, it can be calculated that the maximum energy yield of glycolic acid ($\gamma_p=6$) produced from glucose ($\gamma_s=24$) would be 4 and from pentose ($\gamma_p=20$) would be 3.3. However, this yield can only be reached if the biological system is capable of uptaking a carbon mole as $CO_2$.

Given this postulate and in view of the growing interest in products from renewable carbon resources, the inventors have set the goal to provide a microorganism and a process making it possible to produce in a simple and industrialisable way from plant biomass and in particular from hexoses and pentoses contained in the same, glycolic acid with improved yields with respect to processes of prior art.

To that end, Table 1 hereinafter gives theoretical yields of pathways of prior art for producing glycolic acid (mol/mol) depending on the carbon source used.

TABLE 1

|  | Xylose | Glucose | Reference |
|---|---|---|---|
| Glyoxylate shunt (GS) pathway | 1.66 | 2 | [3] |
| Ribulose-1P pathway | 1 | 0 | [5] |
| Xylulose-1P pathway | 1 | 0 | [7] |
| Ribulose-1P + GS pathways | 2 | 2 | [6] |
| Xylulose-1P + GS pathways | 2 | 2 | [8] |

DISCLOSURE OF THE INVENTION

The present invention enables the technical problems of processes of prior art such as those previously defined to be solved and the goal set by the inventors to be reached.

To that end, the works of the inventors have identified three enzymes enabling the non-natural way for synthesising glycolic acid presented in FIG. 1 to be constructed, said enzymes being:

i) D-arabinose-5-phosphate isomerase (KdsD), enzyme of the lipopolysaccharide synthetic pathway which converts D-ribulose-5-phosphate into D-arabinose-5-phosphate [11];

ii) fructose-6-phosphate aldolase (FSA) which catalyses the cleavage of D-arabinose-5-phosphate into D-glyceraldehyde-3-phosphate and glycolaldehyde; it is to be noted that this enzyme had been initially identified as catalysing the aldolytic cleavage of fructose-6-phosphate into dihydroxyacetone and glyceraldehyde-3-phosphate, but has shown an aldolytic activity on D-arabinose-5-phosphate with an affinity 10 times higher than for fructose-6-phosphate [12] and iii) aldehyde dehydrogenase (AldA) which oxidises glycolaldehyde into glycolate [13].

It is to be noted that the first substrate of this new pathway, namely D-ribulose-5-phosphate, is naturally obtained from pentoses by the pentose phosphate (PP) pathway.

Even if these three enzymes are naturally expressed in microorganisms as *E. coli*, they do not allow glycolic acid synthesis since the overexpression of kdsD, fsa and aldA genes and thus the overexpression of these enzymes are necessary to produce glycolic acid. In other words, the synthetic pathway according to the invention does not exist in the natural state in microorganisms as *E. coli*. That can therefore be called a "non-natural pathway" or "synthetic metabolic pathway".

Additionally, the FSA activity on D-arabinose-5-phosphate generates glyceraldehyde 3P (C3) which is supported by the oxidative glycolysis. As described in [8], this C3 molecule can give glycolaldehyde but with a $CO_2$ loss at the reaction catalysed by pyruvate dehydrogenase. To bypass this metabolic limit, the inventors have rearranged the central carbon metabolism in order to optimise carbon preservation by recovering this C3 in the PP pathway by attenuating or even inactivating the gapA gene coding glyceraldehyde-3-phosphate dehydrogenase. As a result of this attenuation/inactivation, glyceraldehyde-3-phosphate enters the PP pathway and participates in the synthesis of D-xylulose-5-phosphate, precursor of D-ribulose-5-phosphate. The maximum theoretical yield is thereby 2.5 moles of glycolic acid per mole of pentose.

Moreover, for a process to be economically viable, it should convert majority lignocellulosic sugars, namely pentoses as D-xylose and hexoses as D-glucose. The latter is naturally assimilated by the glycolysis pathway. Thus, by inactivating/deleting the gapA gene, the carbon flow is redirected to the PP pathway which makes the conversion of D-glucose into glycolic acid possible with a theoretical maximum yield of 3 moles of glycolic acid per mole of D-glucose.

Table 2 below resumes the theoretical yields of the pathways of prior art and gives the theoretical yield of the pathway according to the invention for producing glycolic acid (mol/mol) depending on the carbon source used.

TABLE 2

|  | Xylose | Glucose | Reference |
|---|---|---|---|
| Glyoxylate shunt (GS) pathway | 1.66 | 2 | [3] |
| Ribulose-1P pathway | 1 | 0 | [5] |
| Xylulose-1P pathway | 1 | 0 | [7] |
| Ribulose-1P + GS pathways | 2 | 2 | [6] |
| Xylulose-1P + GS pathways | 2 | 2 | [8] |
| Pathway according to the present invention | 2.5 | 3 |  |

Thus, the present invention enables glycolic acid synthesis to be made from hexoses and pentoses by a single non-natural pathway, which enables the renewable carbon to be valued at best. Finally, this approach removes the stoichiometric requirement made necessary by the *E. coli* metabolism. Further, calculations on the theoretical yields of the non-natural pathway of pentose and hexose assimilation described in the present invention, for producing glycolic acid, enable a significant improvement in the yields to be foreseen with respect to the biosynthesis processes based on the optimisation of natural and/or semi-synthetic pathways of prior art.

More particularly, the present invention relates to a recombinant microorganism which exhibits
i) a conversion activity from D-ribulose-5-phosphate into D-arabinose-5-phosphate, increased in comparison with the same, non-modified microorganism;
ii) an aldolic cleavage activity from D-arabinose-5-phosphate into D-glyceraldehyde-3-phosphate and glycolaldehyde, increased in comparison with the same, non-modified microorganism;
iii) an oxidation activity from glycolaldehyde into glycolate, increased in comparison with the same, non-modified microorganism; and
iv) an oxidation activity from glyceraldehyde-3-phosphate into 1,3-bisphosphoglycerate, decreased in comparison with the same, non-modified microorganism,
said recombinant microorganism producing glycolic acid from pentoses and hexoses.

By "microorganism", it is meant any organism which exists in the form of a microscopic cell belonging both to the procaryote and the eukaryote fields. Consequently, the term "microorganism" encompasses procaryotic micro-algae, bacteria, archaea and eubacteria of all the species as well as eukaryotic microorganisms such as plant cells, eukaryotic micro-algae, yeasts and fungi. The term also comprises cell cultures of any species which can be cultured for glycolic acid production.

By way of examples of bacteria usable within the scope of the present invention, bacteria from the families Burkholderiaceae, Enterobacteriaceae, Brevibacteriaceae, Clostridiaceae, Bacillaceae, Moraxellaceae, Sphingomonadaceae, Lactobacillaceae, Streptomycetaceae, Streptococcaceae, Methylobacteriacae and Corynebacteriaceae can be mentioned. By way of more particular examples of bacteria usable within the scope of the present invention, *Brevibacterium flavum, Brevibacterium lactofermentum, Escherichia coli, Bacillus subtilis, Corynebacterium glutamicum, Corynebacterium efficiens, Zymomonas mobilis, Ralstonia eutropha, Clostridium acetobutylicum, Methylobacterium extorquens* and *Lactococcus lactis* can be mentioned.

By way of examples of yeasts usable within the scope of the present invention, yeasts from the families Saccharomycetaceae, Pichiaceae, Schizosaccharomycetaceae and *Yarrowia* can be mentioned. By way of more particular examples of yeasts usable within the scope of the present invention, *Saccharomyces cerevisiae, Schizosaccharomyces pombe, Candida albicans, Candida blankii, Candida rugosa, Kluyveromyces lactis, Kluyveromyces marxianus, Pichia jadinii, Scheffersomyces stipitis, Pichia pastoris* and *Yarrowia lipolytica* can be mentioned.

By way of examples of fungi usable within the scope of the present invention, fungi of the genera *Penicillium, Aspergillus, Chrysosporium* and *Trichoderma* can be mentioned. By way of more particular examples of fungi usable within the scope of the present invention, *Penicillium notatum, Penicillium chrysogenum, Aspergillus niger, Chrysosporium pannorum* and *Trichoderma reesei* can be mentioned.

More particularly, the microorganism implemented within the scope of the present invention is an *E. coli* type bacterium or a *Saccharomyces cerevisiae* type yeast.

By "recombinant microorganism", it is intended a microorganism such as previously defined which is not found in nature and which is genetically different from its equivalent in nature. The terms "equivalent in the nature", "non-modified microorganism", "natural microorganism" and "wild type microorganism" are equivalent and usable interchangeably. The recombinant microorganism is modified by introduction, deletion and/or modification of genetic elements.

The recombinant microorganism usable in the present invention can be modified to modulate the expression level of an endogenous gene. By "endogenous gene", it is intended a gene which was present in the microorganism before any genetic modification of the wild type microorganism.

Endogenous genes can be overexpressed by introducing additional heterologous sequences or by replacing endogenous regulatory elements, or by introducing one or more further copies of the gene in a chromosome or on one or more plasmid(s). Endogenous genes can also be modified to modulate their expression and/or their activity. For example, mutations can be introduced in the coding sequence to modify the gene product or heterologous sequences can be introduced in addition or to replace the endogenous regulatory elements. The modulation of an endogenous gene can cause a positive regulation and/or an increase in the activity of the endogenous gene product or, alternatively, downregulate and/or decrease the activity of the endogenous gene product.

Another way to modulate the expression of an endogenous gene is to exchange the endogenous promoter of the same as the wild type promoter, with a stronger or weaker promoter to upregulate or downregulate the expression of the endogenous gene. These promoters can be homologous or heterologous.

Alternatively, the recombinant microorganism usable in the present invention can also be modified to express an exogenous gene. The recombinant microorganism usable in the present invention can be modified to express exogenous genes if these genes are introduced with all the elements enabling them to be expressed in this microorganism. Those skilled in the art know different modification, transformation or transfection methods of a microorganism with an exogenous gene. By way of example and not exhaustively, this method can be a conjugation; an electroporation; a lipofection; a micro-injection; a particle bombardment (or biolistic); a biological transformation of a plant using *Agrobacterium tumefasciens*; a transformation by a chemical permeabilisation; a transformation by the DEAE-dextran method or an introduction via a virus, a virion or a viral particle.

By "exogenous gene", it is intended a gene which has been introduced in a microorganism, by means well known to those skilled in the art whereas this gene is not naturally found in the microorganism. Exogenous genes can be integrated in one or the chromosome of the microorganism or be expressed extra-chromosonally by means of plasmids, vectors, cosmids, bacteriophages or viruses such as a baculovirus. An exogenous gene can be a homologous gene.

By "homologous gene", it is intended a gene homologous to a gene coding a reference protein and which codes a protein homologous to this reference protein. By "protein homologous to a reference protein", it is intended a protein having a similar function and/or a similar structure as the reference protein. Thus, when the reference protein is an enzyme, a protein homologous to this reference protein catalyses the same enzymatic reaction.

By using references given in databases of amino acid or nucleotide sequences such as Genbank or NCBI BioProject for known genes or proteins, those skilled in the art are capable of determining genes or proteins which are homologous i.e. equivalent in other organisms as bacterial strains, yeasts, fungi, mammals or even plants. This routine work is advantageously made by using consensus sequences identified by sequence alignments with genes or proteins, derived from other organisms.

A homologous of a gene A can also be a gene coding for a variant of the protein coded by the gene A. This homologous can be obtained by synthetic pathway.

Typically, a protein (or a gene) homologous to a reference protein (or a reference gene) has at least 40%, at least 45%, at least 50%, at least 55%, at least 60%, at least 65%, at least 70%, at least 75%, at least 80%, at least 85%, at least 90%, at least 95% and/or at least 99% identity respectively with the amino acid sequence of the reference protein (or the nucleotide sequence of the reference gene). By "identity percentage" between two amino acid sequences (or between two nucleotide sequences), it is intended, within the scope of the present invention, a percentage of amino acid residues (or nucleotides) that are identical between both compared sequences, this percentage being obtained after implementing the best alignment (optimum alignment) between both sequences. Those skilled in the art know different techniques enabling such an identity percentage to be obtained and involving homology algorithms or computer programs such as the BLAST program.

The recombinant microorganism according to the invention has one or more increased enzymatic activity(ies) in comparison with the same, non-modified microorganism and at least one enzymatic activity decreased in comparison with the same, non-modified microorganism. In other words, the intracellular activity of some enzymes is increased in comparison with the same, non-modified microorganism and the intracellular activity of at least one other enzyme is decreased in comparison with the same, non-modified microorganism.

In the present invention, the term "activity" of an enzyme is used interchangeably with the term "function" and designates the reaction which is catalysed by the enzyme. Those skilled in the art know different techniques to measure the enzymatic activity of a given enzyme. The experimental part hereinafter gives different enzymatic tests usable to measure the activity of enzymes involved in the present invention.

Within the scope of the present invention, the terms "increased activity" applied to an enzyme designate a catalytic activity specific to the enzyme which is increased and/or an amount or availability of the enzyme which is increased in the cell.

Within the scope of the present invention, an increased enzymatic activity in the recombinant microorganism should be understood as an enzymatic activity which is increased by a factor of at least 2, in particular at least 5, in particular at least 10 and, more particularly, at least 20 with respect to the enzymatic activity of the same, non-modified microorganism.

Those skilled in the art know different microbiology and molecular biology techniques usable to obtain, in a given microorganism, the increase in an enzymatic activity.

Indeed, an increase in the enzymatic activity can be achieved ($i_a$) by increasing the number of copies of the gene coding for the enzyme in the microorganism, ($ii_a$) by increasing the expression of the gene coding for the enzyme in the microorganism, for example, by modifying the promoter, the regulatory regions and/or the ribosome binding site, ($iii_a$) by modifying the sequence of the gene coding the enzyme so as to obtain a form which is more active or more resistant to inhibition and, optionally, ($iv_a$) by combining at least two of the alternatives ($i_a$), ($ii_a$) and ($iii_a$).

As regards the alternative ($i_a$) above, the gene can be coded chromosomally or extra-chromosomally. When the gene is located on the chromosome, several copies of the gene can be introduced on the chromosome by recombination methods, known to those skilled in the art (including via gene replacement). When the gene is located extra-chromosomally, it can be carried by a recombinant expression vector.

By "recombinant expression vector", it is intended a nucleic acid adapted to express, in a microorganism, at least one enzyme coded by a nucleotide sequence contained in this vector. The expression vector according to the present invention comprises, in addition to the nucleotide sequence coding for an enzyme of interest, one (or more) element(s) which enable(s) this nucleotide sequence to be expressed i.e. transcribed and translated.

The expression vector implemented in the present invention is advantageously chosen from a plasmid, a cosmid, a bacteriophage and a virus such as a baculovirus. In particular, the vector of the invention is an autonomously replicating vector including elements enabling it to be maintained and replicated in the microorganism such as a replication origin. Further, the vector can include elements enabling it to be selected in the microorganism. These elements are also known as "selection markers". Such expression vectors are well known to those skilled in the art and widely described in literature.

An expression vector can further have one or more element(s) chosen from a promoter, an enhancer, a 3' UTR ("UnTranslated Region") signal, an IRES ("Internal Ribosome Entry Site") signal, a ribosome binding site (RBS), a transcription termination signal comprising a cleavage site and a polyA signal ("polyadenylation signal"). The expression vector according to the invention can comprise 2, 3 or 4 elements listed above. Those skilled in the art are capable of choosing, in this list, the additional element(s) that the expression vector can comprise depending on the microorganism in which the expression should be made.

By "selection marker", it is intended a marker chosen from a selection marker usable in prokaryotes or in eukaryotes such as an antibiotic resistance bacterial gene and a metabolism gene to be used with an auxotrophic microorganism, i.e. a selection gene which ensures the complementation with the respective gene deleted at the genome of the host microorganism. Thus, the expression vector according to the present invention can contain a bacterial gene for resisting to an antibiotic such as amoxicillin, ampicillin, phleomycin, kanamycin, chloramphenicol, neomycin, hygromycin, geneticin (or G418), carboxin, nourseothricin or triclosan. By way of illustrating examples of metabolism genes, the gene trp1 to be used with a microorganism lacking the phosphoribosylanthranilate isomerase enzyme such as a yeast trp1$^-$ or the gene URA3 to be used with the eukaryotic organism lacking the orotidine 5-phosphate decarboxylase enzyme such as a yeast ura3$^-$ can be mentioned.

By "promoter", it is intended, within the scope of the present invention, both a constitutive or inducible promoter, adapted to any microorganism such as previously defined and a constitutive or inducible promoter, specific to a group of particular microorganisms. The usable promoter can be homologous or heterologous. A constitutive promoter usable within the scope of the present invention is in particular chosen from promoter proD, promoter proC, promoter 35S, promoter 19S and promoter TEV ("Tobacco Etch Virus"). An inducible promoter usable within the scope of the present invention can be promoter GAL1 inducible by galactose, promoter AOX1 inducible by methanol, promoter PA1lacO-1 inducible by isopropyl β-D-1-thiogalactopyranoside (IPTG), the pTac hybrid promoter inducible by IPTG; promoter MET15 inducible by methionine depletion or promoter CUP1 inducible by cupper ions. In the vector implemented in the present invention, the promoter can be associated with one or more transcriptional regulatory sequences that are the enhancers.

Advantageously, the expression vector implemented in the present invention comprises, being operationally linked together, a promoter, a nucleotide sequence coding for an enzyme of interest and a transcription termination signal comprising a cleavage site and/or a polyA signal. By "operationally linked together" according to the invention, it is intended elements linked together such that the functioning of one of the elements is altered by that of another. By way of example, a promoter is operationally linked to a coding sequence when it is capable of altering the expression of the same. The elements with regulate transcription, translation and maturation of peptides that the vector can comprise are known to those skilled in the art and the latter is capable of choosing them depending on the host microorganism in which the expression or cloning should be made.

Furthermore, those skilled in the art know, as an expression vector, different plasmid types which differ by their replication origin and thus by their copy number in the cell. Typically, these plasmids are present in the microorganism as 10 to 15 copies, or about 30 to 50 copies, or even up to 100 copies, depending on the plasmid nature: plasmids with a low copy number with a narrow replication, plasmids with a medium copy number or plasmids with a high copy number. By way of examples of plasmids usable within the scope of the present invention, plasmids pSC101, RK2, pACYC, pRSF1010, pZ and pSK bluescript II can be mentioned.

Typically, the alternative (ii$_a$) above consists in using a promoter inducing a high expression level of the endogenous gene. Depending on the nature and properties of the endogenous promoter, those skilled in the art will be able to determine which promoter, being homologous or heterologous, inducible or constitutive, to use in order to replace said endogenous promoter. Alternatively, the alternative (ii$_a$) can consist in attenuating the activity or expression of a transcription repressor, which is specific or not to the endogenous gene.

Within the scope of the present invention, the terms "decreased activity" or "reduced activity" applied to an enzyme designates a reduced catalytic activity specific to the enzyme and/or a decreased amount or availability of the enzyme in the cell.

Within the scope of the present invention, a decreased enzymatic activity in the recombinant microorganism should be intended as an enzymatic activity which is reduced by a factor of at most 0.5, in particular at most 0.1, in particular, at most 0.01 and more particularly, at most 0.001 with respect to the enzymatic activity of the same, non-modified microorganism.

Those skilled in the art know different microbiology and molecular biology techniques usable to obtain, in a given microorganism, the decrease in an enzymatic activity.

Indeed, a decrease in the enzymatic activity can be achieved (i$_d$) by decreasing the expression of the gene coding the enzyme in the microorganism, for example, by modifying the promoter, the regulatory regions and/or the ribosome binding site, (ii$_d$) by modifying the sequence of the gene coding for the enzyme so as to achieve a reduced expression of the gene and/or the expression of an enzyme the activity of which is reduced, (iii$_d$) by using elements which destabilise the mRNA obtained after the gene transcription and, optionally, (iv$_d$) by inactivating the gene in particular by total or partial deletion of said gene, by total or partial deletion of the promoter preventing any expression of the gene and/or by inserting an external gene element in the coding region of the gene or in the promoter region. It is to be noted that, in some forms of the alternative (iv$_d$) and in particular in the case of a total deletion of the gene, it is possible to have no residual enzymatic activity. In other words, in the alternative (iv$_d$), the enzymatic activity is silenced.

The recombinant microorganism according to the invention has a conversion activity from D-ribulose-5-phosphate into D-arabinose-5-phosphate, increased in comparison with the same, non-modified microorganism. In other words, the intracellular activity of the enzyme which converts D-ribulose-5-phosphate into D-arabinose-5-phosphate in the recombinant microorganism is increased in comparison with the same, non-modified microorganism.

The enzyme (E$_i$) which converts D-ribulose-5-phosphate into D-arabinose-5-phosphate is in the form of a D-arabinose-5-phosphate isomerase (EC 5.3.1.13). Such an enzyme is also known as "D-arabinose-5-phosphate aldose-ketose-isomerase", "arabinose phosphate isomerase", "D-arabinose-5-phosphate ketol-isomerase" and "phosphoarabinoisomerase". All these designations make reference to the same enzyme and are interchangeably usable.

Thus the recombinant microorganism according to the invention presents a conversion activity from D-ribulose-5-phosphate into D-arabinose-5-phosphate catalysed by an enzyme consisting in a D-arabinose-5-phosphate isomerase that converts D-ribulose-5-phosphate into D-arabinose-5-phosphate, increased in comparison with the same, non-modified microorganism Advantageously, the enzyme (E$_i$) is coded by the E. coli kdsD gene or by a homologue of such a gene. Based on the previously provided "homologue" definition, a homologue of the E. coli kdsD gene encodes a protein capable of converting D-ribulose-5-phosphate into D-arabinose-5-phosphate. By way of particular example of E. coli kdsD gene, the gene from the strain K12 MG1655 the coding sequence of which is included between nucleotides 2829813 and 2830778 in the sequence NC_000913.3 accessible from the NCBI ("National Center for Biotechnology Information") site and corresponding to the full genome of the strain K12 MG1655 can be mentioned. The protein sequence of 321 amino acids, which is coded by this gene is referenced, on the NCBI site, sequence NP_417188.4 and corresponds to the sequence SEQ ID NO: 1 in the appended sequence listing.

All the previously contemplated alternatives to increase an enzymatic activity are usable to increase the activity of the enzyme (E$_i$) which converts D-ribulose-5-phosphate into D-arabinose-5-phosphate.

Typically, in the recombinant microorganism according to the invention, the increase in the conversion activity from D-ribulose-5-phosphate into D-arabinose-5-phosphate catalysed by an enzyme consisting in a D-arabilose-5-phosphate isomerase is obtained by increasing the number of copies of the gene coding for this enzyme in the microorganism and/or by increasing the expression of the gene coding for this enzyme in the microorganism. In particular, the recombinant microorganism subject matter of the present invention exhibits an overexpression of the gene coding for a D-arabilose-5-phosphate isomerase which converts D-ribulose-5-phosphate into D-arabinose-5-phosphate.

More particularly, the recombinant microorganism subject matter of the present invention exhibits an overexpression of the E. coli kdsD gene or a homologue thereof.

The recombinant microorganism according to the invention exhibits an aldolic cleavage activity from D-arabinose-5-phosphate into D-glyceraldehyde-3-phosphate and glycolaldehyde, increased in comparison with the same, non-modified microorganism. In other words, the intracellular activity of the enzyme which catalyses the cleavage of D-arabinose-5-phosphate into D-glyceraldehyde-3-phosphate and glycolaldehyde in the recombinant microorganism is increased in comparison with the same, non-modified microorganism.

The enzyme ($E_{ii}$) which catalyses the cleavage of D-arabinose-5-phosphate into D-glyceraldehyde-3-phosphate and glycolaldehyde is in the form of a fructose-6-phosphate aldolase (EC 4.1.2.-) [14].

Thus, the recombinant micro-organism according to the invention exhibits an aldolic cleavage activity from D-arabinose-5-phosphate into D-glyceraldehyde-3-phosphate and glycolaldehyde, catalysed by an enzyme consisting in a fructose-6-phosphate aldolase which catalyses the cleavage of D-arabinose-5-phosphate into D-glyceraldehyde-3-phosphate and glycolaldehyde, increased in comparison with the same, non-modified microorganism.

Advantageously, the enzyme ($E_{ii}$) is coded by the E. coli fsa gene or a homologue of such a gene. Based on the previously provided "homologue" definition, a homologue of the E. coli fsa gene encodes a protein capable of catalysing the cleavage of D-arabinose-5-phosphate into D-glyceraldehyde-3-phosphate and glycolaldehyde. By way of particular examples of the E. coli fsa gene, one can mention:

the gene fsaA from the strain K12 MG1655 the coding sequence of which is included between the nucleotides 863642 and 864304 in the sequence NC_000913.3 accessible from the NCBI site. The protein sequence of 220 amino acids (FSAA), coded by this gene is referenced, on the NCBI site, sequence NP_415346.4 and corresponds to the sequence SEQ ID NO: 2 in the appended sequence listing, and the gene fsaB from the strain K12 MG1655 the coding sequence of which is included, in the complementary strand, between the nucleotides 4139046 and 4139708 in the sequence NC_000913.3 accessible from the NCBI site. The protein sequence of 220 amino acids (FSAB), coded by this gene is referenced, on the NCBI site, sequence NP_418381.1 and corresponds to the sequence SEQ ID NO: 3 in the appended sequence listing.

As particular examples of homologous of the E. coli fsa gene, on can mention the genes coding for the fructose-6-phosphate aldolase variants FSAA L107Y/A129G and FSAA A129T/A165G disclosed by Szekrenyi et al, 2014 [15].

All the previously contemplated alternatives to increase an enzymatic activity are usable to increase the activity of the enzyme ($E_{ii}$) which catalyses the cleavage of D-arabinose-5-phosphate into D-glyceraldehyde-3-phosphate and glycolaldehyde.

Typically, in the recombinant microorganism according to the invention, the increase in the aldolic cleavage activity from D-arabinose-5-phosphate into D-glyceraldehyde-3-phosphate and glycolaldehyde, catalysed by an enzyme consisting in a fructose-6-phosphate aldolase is obtained by increasing the number of copies of the gene coding for this enzyme in the microorganism and/or by increasing the expression of the gene coding for this enzyme in the microorganism. In particular, the recombinant microorganism subject matter of the present invention exhibits an overexpression of the gene coding for a fructose-6-phosphate aldolase which catalyses the cleavage of D-arabinose-5-phosphate into D-glyceraldehyde-3-phosphate and glycolaldehyde.

More particularly, the recombinant microorganism subject matter of the present invention exhibits an overexpression of the E. coli fsa gene or a homologue thereof.

The recombinant microorganism according to the invention exhibits an oxidation activity from glycolaldehyde into glycolate, increased in comparison with the same, non-modified microorganism. In other words, the intracellular activity of the enzyme which oxidises glycolaldehyde into glycolate in the recombinant microorganism is increased in comparison with the same, non-modified microorganism.

The enzyme ($E_{iii}$) which oxidises glycolaldehyde into glycolate is in the form of a glycolaldehyde dehydrogenase and in particular a glycolaldehyde dehydrogenase the activity of which requires the presence of the cofactor $NAD^+$ (EC 1.2.1.21).

Thus, the recombinant microorganism according to the invention exhibits an oxidation activity from glycolaldehyde into glycolate catalysed by an enzyme consisting in a glycolaldehyde dehydrogenase which oxidises glycolaldehyde into glycolate, increased in comparison with the same, non-modified microorganism.

Advantageously, the enzyme ($E_{iii}$) is coded by the E. coli aldA gene or a homologue of such a gene. Based on the previously provided "homologue" definition, a homologue of the E. coli aldA gene encodes a protein capable of oxidising glycolaldehyde into glycolate in the presence of a cofactor as, for example, $NAD^+$. By way of particular example of the E. coli aldA gene, the gene from the strain K12 MG1655 the coding sequence of which is included between nucleotides 1488232 and 1489671 in the sequence NC_000913.3 accessible from the NCBI site can be mentioned. The protein sequence of 479 amino acids, coded by this gene is referenced, on the NCBI site, sequence NP_415933.1 and corresponds to the sequence SEQ ID NO: 4 in the appended sequence listing.

All the previously contemplated alternatives to increase an enzymatic activity are usable to increase the activity of the enzyme ($E_{iii}$) which oxidises glycolaldehyde into glycolate.

Typically, in the recombinant microorganism according to the invention, the increase in the oxidation activity from glycolaldehyde into glycolate, catalysed by an enzyme consisting in a glycolaldehyde dehydrogenase is obtained by increasing the number of copies of the gene coding for this enzyme in the microorganism and/or by increasing the expression of the gene coding for this enzyme in the microorganism. In particular, the recombinant microorganism subject matter of the present invention exhibits an overexpression of the gene coding for a glycolaldehyde dehydrogenase which oxidises glycolaldehyde into glycolate.

More particularly, the recombinant microorganism subject matter of the present invention exhibits an overexpression of the E. coli aldA gene or a homologue thereof.

In particular, the recombinant microorganism according to the present invention comprises:

either at least one plasmid having the sequence of the E. coli KdsD gene or a homologue thereof, the sequence of the E. coli fsa gene or a homologue thereof and the sequence of the *E. coli* aldA gene or a homologue thereof, said sequences being optionally cloned as an operon, or at least two plasmids, with an identical nature but having replication origins compatible or of a different nature, one having two sequences, optionally cloned as an operon, chosen from the sequence of the *E. coli* kdsD gene or a homologue thereof, the sequence of the *E. coli* fsa gene or a homologue thereof and the sequence of the *E. coli* aldA gene or a homologue thereof and the other plasmid the third of these sequences. In this alternative, one can have (fsa+aldA) on a plasmid and kdsD on the other; (fsa+kdsD) on a plasmid and aldA on the other or even (kdsD+aldA) on a plasmid and fsa on the other;

or at least three plasmids, being identical or different, each having a different sequence chosen from the sequence of the *E. coli* kdsD gene or a homologue thereof, the sequence of the *E. coli* fsa gene or a homologue thereof and the sequence of the *E. coli* aldA gene or a homologue thereof.

All that has been previously described on plasmids is applicable to the plasmid(s) contained in the recombinant microorganism subject matter of the invention.

More particularly, the recombinant microorganism subject matter of the invention comprises:

α) a first plasmid in which the sequence of the *E. coli* kdsD gene or a homologue thereof and the sequence of the *E. coli* fsa gene or a homologue thereof lie, said sequences being cloned as an operon and under the control of a first inducible or constitutive promoter and β) a second plasmid in which the sequence of the *E. coli* aldA gene or a homologue thereof under the control of a second inducible or constitutive promoter lies, said first and second promoters being identical or different.

The recombinant microorganism according to the invention exhibits an oxidation activity from glyceraldehyde-3-phosphate into 1,3-bisphosphoglycerate, decreased in comparison with the same, non-modified microorganism. In other words, the intracellular activity of the enzyme which oxidises glyceraldehyde-3-phosphate into 1,3-bisphosphoglycerate in the recombinant microorganism is decreased in comparison with the same, non-modified microorganism.

The enzyme ($E_{iv}$) which oxidises glyceraldehyde-3-phosphate into 1,3-bisphosphoglycerate is in the form of a glyceraldehyde-3-phosphate dehydrogenase and in particular of a glyceraldehyde-3-phosphate dehydrogenase the cofactor of which is $NAD^+$ (EC 1.2.1.12). Such an enzyme is also known as "D-glyceraldehyde-3-phosphate:$NAD^+$ oxydoreductase". Both designations make reference to the same enzyme and are interchangeably usable.

Advantageously, the enzyme ($E_{iv}$) is coded by the *E. coli* gapA gene or by a homologue of such a gene. Based on the previously provided "homologue" definition, a homologue of the *E. coli* gapA gene encodes a protein capable of oxidising glyceraldehyde-3-phosphate into 1,3-bisphosphoglycerate in the presence of a cofactor as, for example, $NAD^+$. By way of particular example of the *E. coli* gapA gene, the gene from the strain K12 MG1655 the coding sequence of which is included between nucleotides 1862771 and 1863766 in the sequence NC_000913.3 accessible from the NCBI site can be mentioned. The protein sequence of 331 amino acids, coded by this gene is referenced, on the NCBI site, sequence NP_416293.1 and corresponds to the sequence SEQ ID NO:4 in the appended sequence listing.

All the previously contemplated alternatives to decrease an enzymatic activity are usable to decrease the activity of the enzyme ($E_{iv}$) which oxidises glycolaldehyde into glycolate.

Typically, in the recombinant micro-organism according to the invention, the decrease in the oxidation activity from glyceraldehyde-3-phosphate into 1,3-bisphosphoglycerate catalysed by an enzyme consisting in a glyceraldehyde-3-phosphate dehydrogenase is obtained by decreasing the expression of the gene coding for this enzyme and/or by inactivating the gene coding for this enzyme.

In a particular implementation, in the recombinant microorganism subject matter of the present invention, the expression of the *E. coli* gapA gene or a homologue thereof is decreased but not inactivated with respect to the non-modified microorganism. In this case, the mitigation of the gapA activity enables the growth and, at the same time, the production of glycolic acid. However, maintaining a residual glycolysis does not enable the maximum yield to be reached.

In an alternative implementation, in the recombinant microorganism subject matter of the present invention, the expression of the *E. coli* gapA gene or a homologue thereof is inactivated with respect to the non-modified microorganism. In this case, the growth and the production of glycolic acid are decoupled. The gapA inactivation requires that the recombinant microorganism according to the invention has a growth substrate, containing, in addition to pentoses and/or hexoses, C2, C3 or C4 compounds such as acetate, pyruvate, malate or succinate or which enter the metabolism after the glyceraldehyde-3-phosphate (GAP).

Advantageously, the recombinant microorganism according to the present invention is modified in terms of glucose transport in that the phosphotransferase system (PTS), which depends on phosphoenolpyruvate (PEP) is inactivated, whereas a glucose transport activity coded by *E. coli* galP or *Zymomonas mobilis* glf or a homologue thereof and a transformation activity from glucose into glucose-6-phosphase are increased in comparison with the same, non-modified microorganism. This modification enables D-glucose and D-xylose to be assimilated [8, 16, 17].

As a reminder, in *E. coli*, the phosphotransferase system (PTS), which depends on phosphoenolpyruvate (PEP) is the most efficient system for glucose transport. The activity of the PTS system has an effect on carbon flow distribution and plays a key role in the carbon catabolism repression. The cytoplasmic PTS system is coded by the operon ptsHIcrr. The deletion of the ptsHIcrr operon in particular in *E. coli* is the most commonly employed strategy to inactivate the PTS system.

The PTS⁻ phenotype is characterised by a very limited glucose transport and phosphorylation capability. In a PTS⁻ strain, PEP is not necessary to glucose phosphorylation. Glucokinase catalyses ATP-dependent phosphorylation of glucose in the cytoplasm. The overexpression of galactose permease (GalP) for glucose and glucokinase (Glk) transport for phosphorylation restores the phenotype PTS⁺ [18]. Another strategy is to overexpress $glf_{zm}$ and $glk_{zm}$ genes respectively coding for a facilitated glucose transporter (Glf) and the glucokinase of *Zymomonas mobilis* in *E. coli* [19].

Thus, in the recombinant microorganism according to the present invention, a glucose transport and phosphorylation activity from phosphoenolpyruvate by the phosphoenolpyruvate-dependent phosphotransferase system (PTS) is silenced in comparison with the same, non-modified microorganism.

By way of particular example, the inactivation of the cytoplasmic PTS system coded by the operon ptsHIcrr in *E. coli* results in deleting the genes:

ptsH of the operon ptsHIcrr encoding the phosphate-bearing phosphohistidine protein Hpr, of the PTS system. By way of more particular example of the *E. coli* ptsH gene, the gene from the strain K12 MG1655 the coding sequence of which is included, on the complementary strand, between nucleotides 2533764 and 2534021 in the sequence NC_000913.3 accessible from the NCBI site can be mentioned. The protein sequence of 85 amino acids coded by this gene is referenced, on the NCBI site, sequence NP_416910.1 and corresponds to the sequence SEQ ID NO: 6 in the appended sequence listing.

ptsI of the operon ptsHIcrr encoding the enzyme I of the PTS system (EC 2.7.3.9). By way of more particular example of *E. coli* ptsI gene, the gene from the strain K12 MG1655 the coding sequence of which is included, on the complementary strand, between nucleotides 2534066 and 2535793 in the sequence NC_000913.3 accessible from the NCBI site can be mentioned. The protein sequence of 575 amino acids coded by this gene is referenced, on the NCBI site, sequence NP_416911.1 and corresponds to the sequence SEQ ID NO: 7 in the appended sequence listing.

crr of the operon ptsHIcrr encoding the enzyme IIA of the complex II of the PTS system (EC 2.7.1.69). By way of more particular example of the *E. coli* crr gene, the gene from the strain K12 MG1655 the coding sequence of which is included, on the complementary strand, between nucleotides 2535834 and 2536343 in the sequence NC_000913.3 accessible from the NCBI site can be mentioned. The protein sequence of 169 amino acids coded by this gene is referenced, on the NCBI site, sequence NP_416912.1 and corresponds to the sequence SEQ ID NO: 8 in the appended sequence listing.

Advantageously, the deletion of the ptsG gene of the PTS system, which does not belong to the operon ptsHIcrr, is also required, because PtsG is strongly involved in the catabolic repression in *E. coli*. The PtsG⁻ mutants are capable of simultaneously consuming glucose, arabinose and xylose whereas a wild strain consumes glucose and then arabinose and finally xylose sequentially [20]. The ptsG gene encodes a wide IIB/C hydrophobic domain of the complex II of the PTS system. By way of more particular example of the *E. coli* ptsG gene, the gene from the strain K12 MG1655 strain the coding sequence of which is included, on the complementary strand, between nucleotides 1157869 and 1159302 in the sequence NC_000913.3 accessible from the NCBI site can be mentioned. The protein sequence of 477 amino acids coded by this gene is referenced, on the NCBI site, sequence NP_415619.1 and corresponds to the sequence SEQ ID NO: 9 in the appended sequence listing.

The *E. coli* galP gene encodes a galactose permease. Based on the previously provided "homologue" definition, a homologue of the *E. coli* galP gene encodes a galactose permease type protein. By way of particular example of the *E. coli* galP gene, the gene from the strain K12 MG1655 the coding sequence of which is included between nucleotides 3088284 and 3089678 in the sequence NC_000913.3 accessible from the NCBI site can be mentioned. The protein sequence of 464 amino acids, coded by this gene is referenced, on the NCBI site, sequence NP_417418.1 and corresponds to the sequence SEQ ID NO: 10 in the appended sequence listing.

The *Z. mobilis* glf gene codes for a glucose transporter. Based on the previously provided "homologue" definition, a homologue of the *Z. mobilis* glf gene codes for a glucose transporter. By way of particular example of the *Z. mobilis* glf gene, the gene from the ATCC 31821/ZM4/CP4 strain which encodes the protein of 473 amino acids referenced, in the UniProtKB site, sequence P21906 and corresponding to the sequence SEQ ID NO: 11 in the appended sequence listing can be mentioned.

Advantageously, the recombinant microorganism according to the invention exhibits a transformation activity from glucose into glucose-6-phosphase, increased in comparison with the same, non-modified microorganism. In other words, the intracellular activity of the enzyme which transforms glucose into glucose-6-phosphase in the recombinant microorganism is increased in comparison with the same, non-modified microorganism.

The enzyme which transforms glucose into glucose-6-phosphase is in the form of a glucokinase (EC 2.7.1.2).

Thus the recombinant micro-organism according to the invention exhibits a transformation activity from glucose into glucose-6-phosphase catalysed by an enzyme consisting in a glucokinase which transforms glucose into glucose-6-phosphase, increased in comparison with the same, non-modified microorganism.

Advantageously, this enzyme is coded by the *E. coli* glK gene or by a homologue of such a gene. Based on the previously provided "homologue" definition, a homologue of the *E. coli* glK gene encodes a protein capable of transforming glucose into glucose-6-phosphase. By way of particular example of the *E. coli* glK gene, the gene from the strain K12 MG1655 the coding sequence of which is included between nucleotides 2508461 and 2509426 in the sequence NC_000913.3 accessible from the NCBI site can be mentioned. The protein sequence of 321 amino acids, coded by this gene is referenced, on the NCBI site, sequence NP_416889.1 and corresponds to the sequence SEQ ID NO: 12 in the appended sequence listing.

All the previously contemplated alternatives to increase an enzymatic activity are usable to increase the glucose transporter activity and the transformation activity from the glucose into glucose-6-phosphase.

Typically, in the recombinant microorganism according to the invention, the increase in the glucose transport catalysed by an enzyme consisting in a glucose transporter or a galactose permease is obtained by increasing the number of copies of a gene coding for this enzyme in the microorganism and/or by increasing the expression of a gene coding for this enzyme in the microorganism. In particular, the recombinant microorganism subject matter of the present invention exhibits an overexpression of a gene coding for a glucose transporter and/or an overexpression of a gene coding for a galactose permease which catalyses the glucose transport. Moreover, in the recombinant microorganism according to the invention, the increase in the transformation activity from the glucose into glucose-6-phosphase catalysed by an enzyme consisting in a glucokinase which transforms the glucose into glucose-6-phosphase is obtained by increasing the number of copies of a gene coding for this enzyme in the microorganism and/or by increasing the expression of a gene coding for this enzyme in the microorganism. In particular, the recombinant microorganism subject matter of the present invention exhibits an overexpression of a gene coding for a glucokinase which transforms the glucose into glucose-6-phosphase.

More particularly, the recombinant microorganism subject matter of the present invention exhibits an overexpression of the E. coli aldA gene or the Z. mobilis g/f gene or one of their homologues and an overexpression of the E. coli g/K gene or a homologue thereof. To that end, in the recombinant microorganism according to the invention, the genes listed above are under the dependence of a strong constitutive promoter like the promoter proD.

Advantageously, in order to further optimise glycolic acid production via the non-natural synthetic pathway according to the invention, the recombinant microorganism subject matter of the present invention can exhibit at least one of the following characteristics:

v) an oxidation activity from glycolate into glyoxylate, decreased in comparison with the same, non-modified microorganism;
vi) a repression of the genes involved in regulating the aerobic respiratory metabolism, decreased in comparison with the same, non-modified microorganism;
vii) a glycolate internalisation, decreased in comparison with the same, non-modified microorganism;
viii) an irreversible formation activity of methylglyoxal from dihydroxyacetone, decreased in comparison with the same, non-modified microorganism;
ix) a conversion activity from fructose-6-phosphate into fructose-1,6-biphosphate, decreased in comparison with the same, non-modified microorganism;
x) a production activity of D-ribose-1-phosphate from dihydroxyacetone phosphate and glycolaldehyde, decreased in comparison with the same, non-modified microorganism; and
xi) an oxidation activity from D-glucose-6-phosphate into 6-phospho D-glucono-1,5-lactone, modified in comparison with the same, non-modified microorganism.

The recombinant microorganism according to the invention exhibits an oxidation activity from glycolate to glyoxylate, decreased in comparison with the same, non-modified microorganism. In other words, the intracellular activity of the enzyme which oxidises glycolate into glyoxylate in the recombinant microorganism is decreased in comparison with the same, non-modified microorganism.

The enzyme ($E_v$) which oxidises glycolate into glyoxylate is in the form of glycolate dehydrogenase and in particular a glycolate dehydrogenase the cofactor of which is $NAD^+$ (EC 1.1.99.14). Such an enzyme is also known as "glycolate oxidoreductase" and "glycolate oxidase". All these designations make reference to the same enzyme and are interchangeably usable.

Thus, the recombinant microorganism according to the invention exhibits an oxidation activity from glycolate to glyoxylate catalysed by an enzyme consisting in a glycolate dehydrogenase which oxidises glycolate into glyoxylate, decreased in comparison with the same, non-modified microorganism.

Advantageously, the E. coli glycolate dehydrogenase activity is coded by the glcDEF genes or a homologue of such genes. Based on the previously provided "homologue" definition, a homologue of the E. coli glcD, glcE and glcF genes encodes a protein capable of oxidising glycolate into glyoxylate in the presence of a cofactor as, for example, $NAD^+$.

By way of particular example of E. coli glcD gene, the gene from the strain K12 MG1655 the coding sequence of which is included, on the complementary strand, between nucleotides 3126522 and 3128021 in the sequence NC_000913.3 accessible from the NCBI site can be mentioned. The protein sequence of 499 amino acids, coded by this gene is referenced, on the NCBI site, sequence NP_417453.1 and corresponds to the sequence SEQ ID NO: 13 in the appended sequence listing.

By way of particular example of E. coli glcE gene, the gene from the strain K12 MG1655 the coding sequence of which is included, on the complementary strand, between nucleotides 3125470 and 3126522 in the sequence NC_000913.3 accessible from the NCBI site can be mentioned. The protein sequence of 350 amino acids, coded by this gene is referenced, on the NCBI site, sequence $Y^P$_026191.1 and corresponds to the sequence SEQ ID NO: 14 in the appended sequence listing.

By way of particular example of E. coli glcF gene, the gene from the strain K12 MG1655 the coding sequence of which is included, on the complementary strand, between nucleotides 3124236 and 3125459 in the sequence NC_000913.3 accessible from the NCBI site can be mentioned. The protein sequence of 407 amino acids, coded by this gene is referenced, on the NCBI site, sequence $Y^P$_026190.1 and corresponds to the sequence SEQ ID NO: 15 in the appended sequence listing.

All the previously contemplated alternatives to decrease an enzymatic activity are usable to decrease the glycolate dehydrogenase activity.

Typically, in the recombinant microorganism according to the invention, the decrease of the oxidation activity from glycolate to glyoxylate catalysed by an enzyme consisting in a glycolate dehydrogenase is obtained by decreasing the expression of the gene coding for this enzyme and/or by inactivating the gene coding for this enzyme. More particularly, in the recombinant microorganism subject matter of the present invention, the expression of E. coli glcD, glcE and glcF genes or homologues thereof is decreased with respect to the non-modified microorganism. In a particular implementation, the E. coli glcD, glcE and glcF genes or homologues thereof are deleted in the recombinant microorganism subject matter of the present invention in order to enable glycolate to be accumulated [21].

The recombinant microorganism according to the invention exhibits an aerobic respiratory activity increased in comparison with the same, non-modified microorganism, by decreasing the repression of the genes involved in regulating the aerobic respiratory metabolism. This repression does not involve an enzyme but a transcriptional regulator.

Thus, the recombinant microorganism according to the invention exhibits a repression of the genes involved in the regulation of the aerobic respiratory metabolism induced by a transcriptional regulator capable of repressing the genes involved in the regulation of the aerobic respiratory metabolism, decreased in comparison with the same, non-modified microorganism.

Advantageously, this transcriptional regulator is coded by the E. coli arcA gene or a homologue of such a gene. Based on the previously provided "homologue" definition, a homologue of the E. coli arcA gene encodes a protein capable of repressing the genes involved in the aerobic respiratory metabolism [22].

By way of particular example of E. coli arcA gene, the gene from the strain K12 MG1655 the coding sequence of which is included, on the complementary strand, between nucleotides 4639590 and 4640306 in the sequence NC_000913.3 accessible from the NCBI site can be mentioned. The protein sequence of 238 amino acids, coded by this gene is referenced, on the NCBI site, sequence NP_418818.1 and corresponds to the sequence SEQ ID NO: 16 in the appended sequence listing.

All the previously contemplated alternatives to decrease an enzymatic activity are usable, mutatis mutandis, to decrease the transcriptional regulator activity repressing the genes involved in the aerobic respiratory metabolism.

Typically, in the recombinant microorganism according to the invention, the decrease in the repression of the genes involved in the regulation of the aerobic respiratory metabolism induced by a transcriptional regulator is obtained by decreasing the expression of the gene coding for this regulator and/or by inactivating the gene coding for this regulator.

More particularly, in the recombinant microorganism subject matter of the present invention, the expression of the *E. coli* arcA gene or a homologue thereof is decreased with respect to the non-modified microorganism. In a particular implementation, the *E. coli* arcA gene or homologue thereof is deleted in the subject matter recombinant microorganism of the present invention.

The recombinant microorganism according to the invention exhibits a glycolate internalisation, decreased in comparison with the same, non-modified microorganism. This internalisation involves proteins importing glycolate [23, 24, 25].

Thus, the recombinant microorganism according to the invention exhibits a glycolate internalisation induced by at least one protein importing the glycolate, decreased in comparison with the same, non-modified microorganism.

Advantageously, proteins are coded by the *E. coli* glcA, lldP or yjcG genes or homologues of such genes. Based on the previously provided "homologue" definition, homologues of the *E. coli* glcA, lldP or yjcG genes encode proteins capable of internalising glycolate.

By way of particular example of *E. coli* glcA gene, the gene from the strain K12 MG1655 the coding sequence of which is included between nucleotides 1157869 and 1159302 in the sequence NC_000913.3 accessible from the NCBI site can be mentioned. The protein sequence of 477 amino acids, coded by this gene is referenced, on the NCBI site, sequence NP_415619.1 and corresponds to the sequence SEQ ID NO: 17 in the appended sequence listing.

By way of particular example of *E. coli* lldP gene, the gene from the strain K12 MG1655 the coding sequence of which is included between nucleotides 3777399 and 3779054 in the sequence NC_000913.3 accessible from the NCBI site can be mentioned. The protein sequence of 551 amino acids, coded by this gene is referenced, on the NCBI site, sequence NP_418060.1 and corresponds to the sequence SEQ ID NO: 18 in the appended sequence listing.

By way of particular example of *E. coli* yjcG gene, the gene from the strain K12 MG1655 the coding sequence of which is included, on the complementary strand, between nucleotides 4283253 and 4284902 in the sequence NC_000913.3 accessible from the NCBI site can be mentioned. The protein sequence of 549 amino acids, coded by this gene is referenced, on the NCBI site, sequence NP_418491.1 and corresponds to the sequence SEQ ID NO: 19 in the appended sequence listing.

All the previously contemplated alternatives to decrease an enzymatic activity are usable, mutatis mutandis, to decrease the activity of proteins importing glycolate.

Typically, in the recombinant microorganism of the invention, the decrease in the glycolate internalization induced by one or more protein(s) importing the glycolate is obtained by decreasing the expression of the gene(s) coding this or these protein(s) and/or by inactivating the gene(s) coding this or these protein(s).

More particularly, in the recombinant microorganism subject matter of the present invention, the expression of the *E. coli* glcA, lldP or yjcG genes or homologues thereof is decreased with respect to the non-modified microorganism. Alternatively, in the recombinant microorganism subject matter of the present invention, the *E. coli* glcA, lldP or yjcG genes or homologues thereof are deleted with respect to the non-modified microorganism.

The recombinant microorganism according to the invention exhibits an irreversible formation activity of methylglyoxal from dihydroxyacetone phosphate (DHAP), decreased in comparison with the same, non-modified microorganism. In other words, the intracellular activity of the enzyme which irreversibly forms methylglyoxal, a cytotoxic compound, from DHAP in the recombinant microorganism is decreased in comparison with the same, non-modified microorganism.

The enzyme ($E_{viii}$) which irreversibly forms methylglyoxal from DHAP is in the form of a methylglyoxal synthase (EC 4.2.3.3) [26].

Thus, the recombinant microorganism according to the invention exhibits an irreversible formation activity of methylglyoxal from DHAP catalysed by an enzyme consisting in a methylglyoxal synthase which irreversibly forms methylglyoxal from DHAP, decreased in comparison with the same, non-modified microorganism.

Advantageously, the enzyme ($E_{viii}$) is coded by the *E. coli* mgsA gene or by a homologue of such a gene. Based on the previously provided "homologue" definition, a homologue of the *E. coli* mgsA gene encodes a protein capable of irreversibly forming, methylglyoxal from DHAP. By way of particular example of *E. coli* mgsA gene, the gene from the strain K12 MG1655 the coding sequence of which is included, on the complementary strand, between nucleotides 1026557 and 1027015 in the sequence NC_000913.3 accessible from the NCBI site can be mentioned. The protein sequence of 152 amino acids, coded by this gene is referenced, on the NCBI site, sequence NP_415483.2 and corresponds to the sequence SEQ ID NO: 20 in the appended sequence listing.

All the previously contemplated alternatives to decrease an enzymatic activity are usable to decrease the activity of the enzyme ($E_{viii}$) which irreversibly forms methylglyoxal from DHAP.

Typically, in the recombinant microorganism according to the invention, the decrease in the irreversible formation activity of methylglyoxal from DHAP catalysed by an enzyme consisting in a methylglyoxal synthase is obtained by decreasing the expression of the gene coding for this enzyme and/or by inactivating the gene coding for this enzyme.

More particularly, in the recombinant microorganism subject matter of the present invention, the expression of the *E. coli* mgsA gene or a homologue thereof is decreased with respect to the non-modified microorganism. In a particular implementation, the *E. coli* mgsA gene or homologue thereof is deleted in the recombinant microorganism subject matter of the present invention.

The recombinant microorganism according to the invention has a conversion activity from fructose-6-phosphate into fructose-1,6-biphosphate, decreased in comparison with the same, non-modified microorganism. In other words, the intracellular activity of the enzyme which converts fructose-6-phosphate into fructose-1,6-biphosphate, in the recombinant microorganism is decreased in comparison with the same, non-modified microorganism.

The enzyme ($E_{ix}$) which converts fructose-6-phosphate into fructose-1,6-biphosphate is in the form of a phosphofructokinase (EC 2.7.1.11).

Thus, the recombinant microorganism according to the invention exhibits a conversion activity from fructose-6-phosphate into fructose-1,6-biphosphate catalysed by an enzyme consisting in a phosphofructokinase which converts fructose-6-phosphate into fructose-1,6-biphosphate, decreased in comparison with the same, non-modified microorganism.

Advantageously, the enzyme ($E_{ix}$) is coded by the *E. coli* pfKA gene or a homologue of such a gene. Based on the previously provided "homologue" definition, a homologue of the *E. coli* pfKA gene encodes a protein capable of converting fructose-6-phosphate into fructose-1,6-biphosphate. By way of particular example of *E. coli* pfKA gene, the gene from the strain K12 MG1655 the coding sequence of which is included, on the complementary strand, between nucleotides 4107552 and 4108514 in the sequence NC_000913.3 accessible from the NCBI site can be mentioned. The protein sequence of 320 amino acids, coded by this gene is referenced, on the NCBI site, sequence NP_418351.1 and corresponds to the sequence SEQ ID NO: 21 in the appended sequence listing.

All the previously contemplated alternatives to decrease an enzymatic activity are usable to decrease the activity of the enzyme ($E_{ix}$) which converts fructose-6-phosphate into fructose-1,6-biphosphate.

Typically, in the recombinant microorganism according to the invention, the decrease in the conversion activity from fructose-6-phosphate into fructose-1,6-biphosphate catalysed by an enzyme consisting in a phosphofructokinase is obtained by decreasing the expression of the gene coding for this enzyme and/or by inactivating the gene coding for this enzyme.

More particularly, in the recombinant microorganism subject matter of the present invention, the expression of the *E. coli* pfKA gene or a homologue thereof is decreased with respect to the non-modified microorganism. In a particular implementation, the *E. coli* pfKA gene or homologue thereof is deleted in the recombinant microorganism subject matter of the present invention, in order to avoid a futile cycle with fructose-1,6-biphosphate [27].

The recombinant microorganism according to the invention exhibits a production activity of D-ribose-1-phosphate from dihydroxyacetone phosphate and glycolaldehyde, decreased in comparison with the same, non-modified microorganism. In other words, the intracellular activity of the enzyme which produces D-ribose-1-phosphate from dihydroxyacetone phosphate and glycolaldehyde, in the recombinant microorganism is decreased in comparison with the same, non-modified microorganism.

The enzyme (Ex) which produces D-ribose-1-phosphate from dihydroxyacetone phosphate and glycolaldehyde is in the form of a L-fuculose-phosphate aldolase (EC 4.1.2.17) [28].

Thus, the recombinant microorganism according to the invention exhibits a production activity of D-ribose-1-phosphate from dihydroxyacetone phosphate and glycolaldehyde catalysed by an enzyme consisting in a L-fuculose-phosphate aldolase which produces D-ribose-1-phosphate from dihydroxyacetone phosphate and glycolaldehyde, decreased in comparison with the same, non-modified microorganism.

Advantageously, the enzyme (Ex) is coded by the *E. coli* fucA gene or a homologue of such a gene. Based on the previously provided "homologue" definition, a homologue of the *E. coli* fucA gene encodes a protein capable of producing D-ribose-1-phosphate from dihydroxyacetone phosphate and glycolaldehyde. By way of particular example of the *E. coli* fucA gene, the gene from the strain K12 MG1655 the coding sequence of which is included, on the complementary strand, between nucleotides 2933041 and 2933688 in the sequence NC_000913.3 accessible from the NCBI site can be mentioned. The protein sequence of 215 amino acids, coded by this gene is referenced, on the NCBI site, sequence NP_417280.1 and corresponds to the sequence SEQ ID NO: 22 in the appended sequence listing.

All the previously contemplated alternatives to decrease an enzymatic activity are usable to decrease the activity of the enzyme (Ex) which catalyses the reversible interconversion from D-ribose-1-phosphate into dihydroxyacetone phosphate and glycolaldehyde.

Typically, in the recombinant microorganism according to the invention, the decrease in the production activity of D-ribose-1-phosphate from dihydroxyacetone phosphate and glycolaldehyde catalysed by an enzyme consisting in a L-fuculose-phosphate aldolase is obtained by decreasing the expression of the gene coding for this enzyme and/or by inactivating the gene coding for this enzyme.

More particularly, in the recombinant microorganism subject matter of the present invention, the expression of the *E. coli* fucA gene or a homologue thereof is decreased with respect to the non-modified microorganism. In a particular implementation, the *E. coli* fucA gene or homologue thereof is deleted in the recombinant microorganism subject matter of the present invention.

The recombinant microorganism according to the invention exhibits a production activity of 6-phospho-D-glucono-1,5-lactone from D-glucose-6-phosphate decreased or increased in comparison with the same, non-modified microorganism.

In a first embodiment, the recombinant microorganism according to the invention exhibits a production activity of 6-phospho-D-glucono-1,5-lactone from D-glucose-6-phosphate decreased in comparison with the same, non-modified microorganism. In other words, the intracellular activity of the enzyme ($E_{xi}$) which produces the 6-phospho-D-glucono-1,5-lactone from D-glucose-6-phosphate, in the recombinant microorganism is decreased in comparison with the same, non-modified microorganism.

The enzyme ($E_{xi}$) which produces 6-phospho-D-glucono-1,5-lactone from D-glucose-6-phosphate is in the form of a NADP$^+$-dependent glucose-6-phosphate dehydrogenase (EC 1.1.1.49) [29].

Thus, the recombinant microorganism according to the invention exhibits a production activity of 6-phospho-D-glucono-1,5-lactone from D-glucose-6-phosphate catalysed by an enzyme consisting in cofactor-dependent glucose-6-phosphate dehydrogenase which produces 6-phospho-D-glucono-1,5-lactone from D-glucose-6-phosphate, decreased in comparison with the same, non-modified microorganism.

Advantageously, the enzyme ($E_{xi}$) is coded by the *E. coli* zwf gene or a homologue thereof. Based on the previously provided "homologue" definition, a homologue of the *E. coli* zwf gene encodes a protein capable of producing 6-phospho-D-glucono-1,5-lactone from D-glucose-6-phosphate in the presence of a cofactor as, for example, NADP$^+$. By way of particular example of the *E. coli* zwf gene, the gene from the strain K12 MG1655 the coding sequence of which is included, on the complementary strand, between nucleotides 1934839 and 1936314 in the sequence NC_000913.3 accessible from the NCBI site can be mentioned. The protein sequence of 491 amino acids, coded by this gene is referenced, on the NCBI site, sequence NP_416366 corresponding to the sequence SEQ ID NO: 23 in the appended sequence listing.

All the previously contemplated alternatives to decrease an enzymatic activity are usable to decrease the activity of the enzyme ($E_{xi}$) which produces 6-phospho-D-glucono-1, 5-lactone from D-glucose-6-phosphate.

Typically, in the recombinant microorganism according to the invention, the decrease in the production activity of 6-phospho-D-glucono-1,5-lactone from D-glucose-6-phosphate catalysed by an enzyme consisting in a cofactor-dependent glucose-6-phosphate dehydrogenase is obtained by decreasing the expression of the gene coding for this enzyme and/or by inactivating the gene coding for this enzyme.

More particularly, in the recombinant microorganism subject matter of the present invention, the expression of the *E. coli* zwf gene or a homologue thereof is decreased with respect to the non-modified microorganism. In a particular implementation, the *E. coli* zwf gene or homologue thereof is deleted in the recombinant microorganism subject matter of the present invention.

In a second embodiment, the recombinant microorganism according to the invention exhibits a production activity of 6-phospho-D-glucono-1,5-lactone from D-glucose-6-phosphate increased in comparison with the same, non-modified microorganism. In other words, the intracellular activity of the enzyme ($E_{xi}$) which produces 6-phospho-D-glucono-1, 5-lactone from D-glucose-6-phosphate, in the recombinant microorganism is increased in comparison with the same, non-modified microorganism.

Thus, the recombinant microorganism according to the invention exhibits a production activity of 6-phospho-D-glucono-1,5-lactone from D-glucose-6-phosphate catalysed by an enzyme consisting in cofactor-dependent glucose-6-phosphate dehydrogenase which produces 6-phospho-D-glucono-1,5-lactone from D-glucose-6-phosphate, increased in comparison with the same, non-modified microorganism.

All the previously contemplated alternatives to increase an enzymatic activity are usable to increase the activity of the enzyme ($E_{xi}$) which produces 6-phospho-D-glucono-1, 5-lactone from D-glucose-6-phosphate.

Typically, in the recombinant microorganism according to the invention, the increase in the production activity of 6-phospho-D-glucono-1,5-lactone from D-glucose-6-phosphate catalysed by an enzyme consisting in a cofactor-dependent glucose-6-phosphate dehydrogenase is obtained by increasing the number of copies of the gene coding for this enzyme and/or by increasing the expression of the gene coding for this enzyme. In particular, the recombinant micro-organism subject matter of the present invention exhibits an overexpression of a gene coding for a cofactor-dependent glucose-6-phosphate dehydrogenase which produces 6-phospho-D-glucono-1,5-lactone from D-glucose-6-phosphate.

More particularly, the recombinant microorganism subject matter of the present invention exhibits an overexpression of the *E. coli* zwf gene or a homologue thereof.

In this second embodiment, the recombinant microorganism subject matter of the invention exhibits the following characteristics:

xi) an oxidation activity from D-glucose-6-phosphate into 6-phospho D-glucono-1,5-lactone, increased in comparison with the same, non-modified microorganism;

xii) a formation activity of 2-dehydroxy-3-deoxy-D-gluconate-6-phosphate from D-gluconate-6-phosphate, decreased in comparison with the same, non-modified microorganism; and xiii) a formation activity of glyceraldehyde-3-phosphate and pyruvate from 2 dehydroxy-3-deoxy-D-gluconate-6-phosphate, decreased in comparison with the same, non-modified microorganism.

In this second embodiment, the recombinant microorganism according to the invention exhibits a formation activity of 2-dehydroxy-3-deoxy-D-gluconate-6-phosphate from D-gluconate-6-phosphate decreased in comparison with the same, non-modified microorganism. In other words, the intracellular activity of the enzyme which forms 2-dehydroxy-3-deoxy-D-gluconate-6-phosphate from D-gluconate-6-phosphate, in the recombinant microorganism is decreased in comparison with the same, non-modified microorganism.

The enzyme ($E_{xii}$) which produces 2-dehydroxy-3-deoxy-D-gluconate-6-phosphate from D-gluconate-6-phosphate is in the form of a phosphogluconate dehydratase (EC 4.2.1.12) [30].

Thus, the recombinant micro-organism according to the invention exhibits a formation activity of 2-dehydroxy-3-deoxy-D-gluconate-6-phosphate from D-gluconate-6-phosphate catalysed by an enzyme consisting in a phosphogluconate dehydratase which produces 2-dehydroxy-3-deoxy-D-gluconate-6-phosphate from D-gluconate-6-phosphate, decreased in comparison with the same, non-modified microorganism.

Advantageously, the enzyme ($E_{xii}$) is coded by the *E. coli* edd gene or a homologue thereof. Based on the previously provided "homologue" definition, a homologue of the *E. coli* edd gene encodes a protein capable of producing 2-dehydroxy-3-deoxy-D-gluconate-6-phosphate from D-gluconate-6-phosphate. By way of particular example of the *E. coli* edd gene, the gene from the strain K12 MG1655 the coding sequence of which is included, on the complementary strand, between nucleotides 1932794 and 1934604 in the sequence NC_000913.3 accessible from the NCBI site can be mentioned. The protein sequence of 603 amino acids, coded by this gene is referenced, on the NCBI site, sequence CAA45221 and corresponds to the sequence SEQ ID NO: 24 in the appended sequence listing.

Typically, in the recombinant microorganism according to the invention, the decrease in the oxidation activity from glyceraldehyde-3-phosphate into 1,3-bisphosphoglycerate catalysed by an enzyme consisting in a glyceraldehyde-3-phosphate dehydrogenase is obtained by decreasing the expression of the gene coding for this enzyme and/or by inactivating the gene coding for this enzyme.

More particularly, in the recombinant microorganism subject matter of the present invention, the expression of the *E. coli* edd gene or of a homologue thereof is decreased in comparison with the non-modified microorganism. In a particular embodiment, the *E. coli* edd gene or the homologue thereof is deleted in the recombinant microorganism subject matter of the present invention.

In this second embodiment, the recombinant microorganism according to the invention exhibits a production activity of D-glyceraldehyde-3-phosphate and pyruvate from 2-dehydroxy-3-deoxy-D-gluconate-6-phosphate decreased in comparison with the same, non-modified microorganism. In other words, the intracellular activity of the enzyme which produces D-glyceraldehyde-3-phosphate and pyruvate from 2-dehydroxy-3-deoxy-D-gluconate-6-phosphate, in the recombinant microorganism is decreased in comparison with the same, non-modified microorganism.

The enzyme ($E_{xiii}$) which produces D-glyceraldehyde-3-phosphate and pyruvate from 2-dehydroxy-3-deoxy-D-gluconate-6-phosphate is in the form of a 2-dehydroxy-3-deoxy-phosphogluconate aldolase [31].

Thus, the recombinant microorganism according to the invention exhibits a production activity of D-glyceraldehyde-3-phosphate and pyruvate from 2-dehydroxy-3-deoxy-D-gluconate-6-phosphate catalysed by an enzyme consisting of a 2-dehydroxy-3-deoxy-phosphogluconate aldolase which produces D-glyceraldehyde-3-phosphate and pyruvate from 2-dehydroxy-3-deoxy-D-gluconate-6-phosphate, decreased in comparison with the same, non-modified microorganism.

Advantageously, the enzyme ($E_{xiii}$) is coded by the *E. coli* eda gene or a homologue thereof. Based on the previously provided "homologue" definition, a homologue of the *E. coli* edd gene encodes a protein capable of producing D-glyceraldehyde-3-phosphate and pyruvate from 2-dehydroxy-3-deoxy-D-gluconate-6-phosphate. By way of particular example of *E. coli* eda gene, the gene from the strain K12 MG1655 the coding sequence of which is included, on the complementary strand, between nucleotides 1932115 and 1932756 in the sequence NC_000913.3 accessible from the NCBI site can be mentioned. The protein sequence of 213 amino acids, coded by this gene is referenced, on the NCBI site, sequence NP_416364.1 and corresponds to the sequence SEQ ID NO: 25 in the appended sequence listing.

Typically, in the recombinant microorganism according to the invention, the decrease in the production activity of D-glyceraldehyde-3-phosphate and pyruvate from 2-dehydroxy-3-deoxy-D-gluconate-6-phosphate catalysed by an enzyme consisting of a 2-dehydroxy-3-deoxy-phosphogluconate aldolase is obtained by decreasing the expression of the gene coding for this enzyme and/or by inactivating the gene coding for this enzyme.

More particularly, in the recombinant microorganism subject matter of the present invention, the expression of the *E. coli* eda gene or of a homologue thereof is decreased in comparison with the non-modified microorganism. In a particular embodiment, the *E. coli* eda gene or the homologue thereof is deleted in the recombinant microorganism subject matter of the present invention.

The glycolic acid synthetic cyclic pathway from main lignocellulosic monosaccharides, with an optimum carbon preservation, in accordance with the present invention is represented in FIG. 2.

The present invention also relates to the use of a recombinant microorganism as previously defined for producing glycolic acid from a culture medium comprising, as a carbon source, at least one pentose and/or at least one hexose.

Thus, the present invention relates to a process for producing glycolic acid comprising the steps of:
 a) culturing a recombinant microorganism as defined previously in a culture medium comprising, as a carbon source, at least one pentose and/or at least one hexose; and
 b) recovering glycolic acid from the microorganism and/or in the culture medium.

The production process subject matter of the present invention implements steps and devices conventionally used in the biofermentation field.

Thus, in step (a) of the process according to the present invention, the microorganism can be cultured in a culture medium according to the usual techniques used to culture this microorganism type. The culture medium can be a commercial medium or an extemporaneously prepared medium.

Advantageously, the culture medium implemented in the process of the invention is in the form of a sterile liquid containing a carbon source, a nitrogen source, a phosphate source, trace elements and optionally a sulphur source.

Within the scope of the present invention, the carbon source comprises at least one pentose and/or at least one hexose. By way of example, this carbon source can comprise at least two different pentoses and at least one hexose, in particular at least xylose, arabinose and glucose and, in particular, D-xylose, L-arabinose and D-glucose. These pentoses and hexose are typically from a renewable carbon material such as plant biomass and, in particular lignocellulosic biomass.

The plant biomass is chosen from the group consisting of agricultural productions such as so-called "energy" dedicated productions such as miscanthus, switchgrass (*Panicum virgatum*) and very short rotation coppices as, for example, poplar or willow; agricultural production residues such as cereal straws, maize canes and sugar cane rods; forest productions; forest production residues such as wood processing residues.

One of the main elements of the plant biomass is lignocellulose, which corresponds to a main component of the plant cellular wall. Lignocellulose is comprised of 75% carbohydrates and its hydrolysis releases fermentescible sugars, mainly D-glucose, D-xylose and L-arabinose [32].

In a first implementation of step (a) of the process according to the invention, the cultured recombinant microorganism is a recombinant microorganism as previously defined and in which the expression of the *E. coli* gapA gene or a homologue thereof is decreased but not inactivated with respect to the non-modified microorganism. In this first implementation, the carbon source implemented can only comprise one element chosen from D-glucose, D-xylose, L-arabinose and a mixture thereof. By "mixture", it is intended a mixture of D-glucose and D-xylose, a mixture of D-glucose and L-arabinose, a mixture of D-xylose and L-arabinose and a mixture of D-glucose, D-xylose and L-arabinose.

In a second implementation of step (a) of the process according to the invention, the cultured recombinant microorganism is a recombinant microorganism as previously defined and in which the expression of the *E. coli* gapA gene or a homologue thereof is inactivated with respect to the non-modified microorganism. In this second implementation, the carbon source implemented comprises, in addition to D-xylose and/or L-arabinose and/or D-glucose, one or more C2, C3 or C4 compounds chosen from malate, pyruvate, succinate, acetate and a mixture thereof. In this second implementation, the process for producing glycolic acid is made in two phases, with a first biomass production phase, followed by a production phase which is triggered when the C2, C3 or C4 compounds come to be depleted promoting bioconversion of hexoses and pentoses into glycolic acid.

In the first and second implementations of the process according to the invention, the carbon source implemented can further comprise at least one other carbon element such as galactose, xylose, fructose, lactose, sucrose, maltose, molasses, starch and a starch hydrolysate.

Examples of adapted nitrogen sources include ammonia, the ammonium salts such as ammonium chloride, ammonium sulphate, ammonium acetate and ammonium phosphate, other nitrogen-containing compounds; a peptone as tryptone; a meat extract, a yeast extract, a maize liquor; a casein hydrolysate; a soya flour and a soya flour hydrolysate.

Those skilled in the art know different examples of sulphur sources, phosphate sources and trace elements usable during step (a) of the process according to the invention. They will be able to choose, without inventive effort, the best adapted sources and trace elements as a function of the cultured recombinant microorganism and the culture conditions.

The temperature during culturing of step (a) is typically between 15 and 45° C., and the pH during this culture is typically maintained at a value between 3.0 and 9.0. The pH can be adjusted by using, for example, an inorganic or organic acid, an alkaline solution, urea or a calcium carbonate.

It is to be noted that, depending on the cultured microorganism, those skilled in the art will be able to adapt the culture medium and culture conditions to the particular requirements thereof, optionally by means of routine tests. Hence, the recombinant microorganism is, during step (a), in conditions under which there is a glycolic acid production from the carbon source as previously defined. Typically, this culturing is made under aerobic conditions i.e. in the presence of oxygen.

Advantageously, the recombinant microorganisms are cultured as a suspension. A cell "suspension" is generally intended as including all the types of suspended or dispersed cellular cultures. The term "as a suspension" are also used to distinguish the cells which are not cultured in a liquid medium, such as the cells cultured by adhering to a Petri dish. On the other hand, the term "suspension" comprises both freely dispersed cells and agglomerated cells, regardless of whether the agglomeration can occur spontaneously or not.

Alternatively, the recombinant microorganisms can be cultured being attached to a solid phase such as microbeads, beads, capillaries, hollow fibres, these different elements being typically of a material compatible with the microorganism as, for example, dextran, gelatin, glass and cellulose.

Moreover, the culturing processes which can be used during step (a) of the process according to the present invention comprise, without being limited thereto, a discontinuous culture, a continuous culture or a "fed-batch" culture.

A "continuous (cellular) culture" is a cellular culture characterised both by a continuous supply of a nutrient liquid feed and a continuous liquid flow. Alternatively, a continuous culture can be a "perfusion culture", in which case the liquid flow contains a culture medium which is substantially devoid of cells, or a cellular concentration substantially lower than that in the bioreactor. In a perfusion culture, the cells can be retained, for example, by filtration, centrifugation or settling.

A "fed-batch" culture is a discontinuous cell culture to which a substrate, in concentrated, solid or liquid form, is periodically or continuously added during analysis. As in a discontinuous culture, a "fed-batch" culture is initiated by inoculated cells to the medium, but, unlike a discontinuous culture, there is a subsequent nutrient inflow, as through a concentrated nutrient feed. Unlike a continuous culture, there is no systematic liquid removal from the culture or cells in a "fed-batch" culture.

Step (a) of the process according to the invention can be implemented in any container adapted to a cellular culture. By way of particular examples, an Erlenmeyer flask, a bioreactor or a biofermenter with different volumes can be mentioned. Additional information on these different containers can be found in [5].

In the process according to the invention, steps (a) and (b) can occur one after the other or, otherwise, simultaneously. Advantageously, during step (b) of the process according to the invention, glycolic acid is recovered in the culture medium.

Further characteristics and advantages of the present invention will further appear to those skilled in the art upon reading examples given below by way of illustrating and no-limiting purposes, in reference to the appended figures.

DETAILED DISCLOSURE OF PARTICULAR EMBODIMENTS

Figure 1:
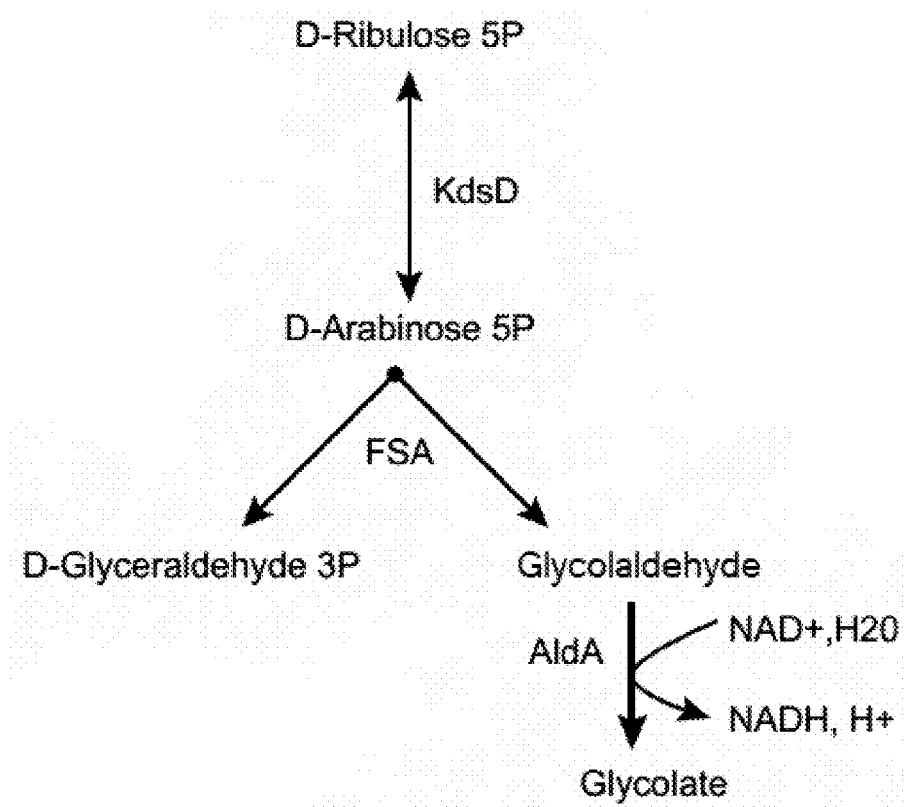
FIG. 1 already mentioned shows the three key reactions for glycolic acid production, isolated from the E. coli central carbon metabolism.
Figure 2:
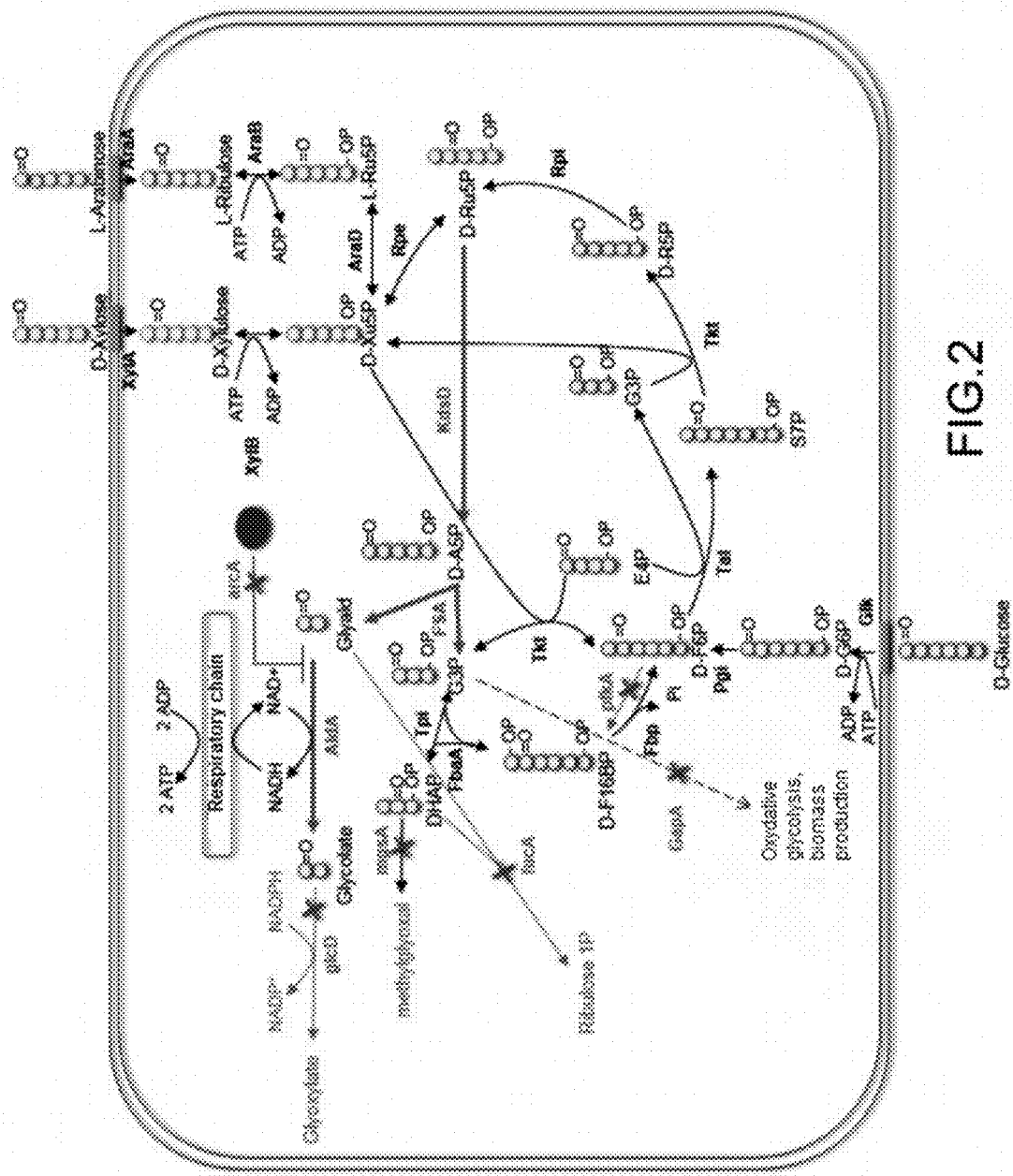
FIG. 2 already mentioned shows the non-natural pathway for glycolic acid production from D-glucose, D-xylose and L-arabinose.

I. Proof of In Vitro Feasibility.
I.1. Material and Methods.
A. Construction of Plasmids.

To construct a system in vitro, the inventors have cloned the ORFs ("Open Reading Frames") of the xylose isomerase (XylA), xylulokinase (XylB), arabinose isomerase (AraA), ribulose kinase (AraB), L-ribulose-5-phosphate 4-epimerase (AraD), ribulose-5-phosphate-3-epimerase (RPE), D-arabinose-5-phosphate isomerase (KdsD), fructose-6-phosphate aldolase (FSA corresponding to FSAA such as previously defined) and aldehyde dehydrogenase (AdA) of E. coli K12 MG1655 with a polyhistidine tag for a facilitated purification. The oligonucleotides used for amplifying ORFS of the E. coli enzymes are listed in Table 3 below, the sequences SEQ ID NO: making reference to the appended sequence listing. The E. coli genomic DNA which served as on template is that of the strain K12 MG1655.

The plasmids for the expression of the C-terminal polyhistidine tagged proteins XylA, XylB, AraA, AraB, AraD, AraB, Rpe, KdsD, FSA, AdA have been constructed by HiFi Assembly® (NEB) with pET28a as a receiving vector. pET28a has been linearised beforehand with the restriction enzymes HindIII and BamHI (NEB) (Table 4). The *E. coli* strain NEB5®, derived from DH5 alpha, has been used for cloning and storing the different plasmids.

RNA polymerase T7, and are thus compatible with the expression system T7 of the vector pET28a. The plasmids pET28a checked beforehand by sequencing have been transformed in the BL21(DE3) according to the NEB protocol. The strains obtained are stored in 50% glycerol at −80° C. (Table 5).

TABLE 3

| Gene | Primer | Primer sequence |
|---|---|---|
| xylA | Sense | ctggtgccgcgcggcagccatATGCAAGCCTATTTTGAC (SEQ ID NO: 26) |
|  | Antisense | gtcgacggagctcgaattcgTTATTTGTCGAACAGATAATGG (SEQ ID NO: 27) |
| xylB | Sense | ctggtgccgcgcggcagccatATGTATATCGGGATAGATCTTG (SEQ ID NO: 28) |
|  | Antisense | gtcgacggagctcgaattcgTTACGCCATTAATGGCAG (SEQ ID NO: 29) |
| araA | Sense | ctggtgccgcgcggcagccatATGACGATTTTTGATAATTATGAAG (SEQ ID NO: 30) |
|  | Antisense | gtcgacggagctcgaattcgTTAGCGACGAAACCCGTAATAC (SEQ ID NO: 31) |
| araB | Sense | ctggtgccgcgcggcagccatATGGCGATTGCAATTGG (SEQ ID NO: 32) |
|  | Antisense | gtcgacggagctcgaattcgTTATAGAGTCGCAACGGCC (SEQ ID NO: 33) |
| araD | Sense | ctggtgccgcgcggcagccatATGTTAGAAGATCTCAAACG (SEQ ID NO: 34) |
|  | Antisense | gtcgacggagctcgaattcgTTACTGCCCGTAATATGC (SEQ ID NO: 35) |
| rpe | Sense | ctggtgccgcgcggcagccatATGAAACAGTATTTGATTGC (SEQ ID NO: 36) |
|  | Antisense | gtcgacggagctcgaattcgTTATTCATGACTTACCTTTGC (SEQ ID NO: 37) |
| kdsD | Sense | gccgcgcggcagccatatATGTCGCACGTAGAGTTAC (SEQ ID NO: 38) |
|  | Antisense | gtcgacggagctcgaattcgTTACACTACGCCTGCACG (SEQ ID NO: 39) |
| fsa | Sense | gccgcgcggcagccatatATGGAACTGTATCTGGATACTTC (SEQ ID NO: 40) |
|  | Antisense | gtcgacggagctcgaattcgTTAAATCGACGTTCTGCC (SEQ ID NO: 41) |
| aldA | Sense | ctggtgccgcgcggcagccatATGTCAGTACCCGTTCAAC (SEQ ID NO: 42) |
|  | Antisense | gtcgacggagctcgaattcgTTAAGACTGTAAATAAACCACC (SEQ ID NO: 43) |

TABLE 4 plasmids used for the proof of in vitro concept

| Name | Description | Reference |
|---|---|---|
| pET28 | Kan $^R$, ColE1 ori | Novagen ® |
| pVT-FSA | fsa-bearing pET28 | This study |
| pVT-KDSD | kdsD-bearing pET28 | This study |
| pVT-ALDA | aldA-bearing pET28 | This study |
| pVT-RPE | rpe-bearing pET28 | This study |
| pVT-XYLA | xylA-bearing pET28 | This study |
| pVT-XYLB | xylB-bearing pET28 | This study |
| pVT-ARAA | araA-bearing pET28 | This study |
| pVT-ARAB | araB-bearing pET28 | This study |
| pVT-ARAD | araC-bearing pET28 | This study |

B. Construction of the Strains.

*E. coli*-competent cells BL21 (DE3) have been used for the expression of tagged proteins since these cells express

TABLE 5

*Escherichia coli* strains used for the proof of in vitro concept

| Strain | Genotype | Reference |
|---|---|---|
| MG1655 | F-λ-ilvG-rfb-50 rph-1 | ATCC 47076 |
| BL21 (DE3) | fhuA2 [lon] ompT gal (λ DE3) [dcm] ΔhsdS | Invitrogen ® |
| prodFSA | pVT-FSA-containing BL21 | This study |
| prodKDSD | pVT-KDSD-containing BL21 | This study |
| prodALDA | pVT-ALDA-containing BL21 | This study |
| prodRPE | pVT-RPE-containing BL21 | This study |
| prodXYLA | pVT-XYLA-containing BL21 | This study |
| prodXYLB | pVT-XYLB-containing BL21 | This study |
| prodARA | pVT-ARAA-containing BL21 | This study |
| prodARAB | pVT-ARAB-containing BL21 | This study |
| prodARAC | pVT-ARAC-containing BL21 | This study |

C. Expression and Purification of Polyhistidine-Tagged Proteins.

All the proteins expressed are soluble and have been produced from the expression vector pET28a transformed in an *E. coli* strain BL21 (DE3). A pre-culture in a LB (for "Luria-Bertani") medium added with the antibiotic kanamycin is made overnight at 37° C. The pre-culture is used to seed a fresh culture of 200 mL of LB-Kanamycin at an optical density at 600 nm ($OD_{600}$) of 0.1 (37° C., 200 rpm). When the $OD_{600}$ is between 0.6 and 0.8, the expression of the protein of interest is induced by adding finally 1 mM IPTG. The proteins are expressed overnight at 16° C. The cells are collected as 50 ml fractions and centrifuged at 4 800 rpm for 15 min at 4° C. The cell pellets are preserved at −20° C.

The purification of proteins is made from the cell pellets obtained during the production step. All the steps are made while cold to avoid degradation of proteins by proteases. The cell pellets are re-suspended in 1.5 mL washing buffer (50 mM HEPES, pH 7.5; 0.3 M NaCl) and then sonicated on ice. A centrifugation step at 13 000 rpm, for 15 min at 4° C. enables the cell debris to be separated from the cytoplasmic liquid. The clarified lysates are deposited onto 600 µl cobalt resin (Clontech) previously balanced with the washing buffer. After 20 min at room temperature in contact with the resin, the tubes are centrifuged (700 rcf, 3 min, 4° C.). The supernatant is removed, the resin is contacted with 3 mL washing buffer for 10 min in order to remove non-specific interactions. After centrifugation (700 rcf, 3 min, 4° C.) and removing the supernatant, 3 mL of a solution of 15 mM imidazole are contacted with the resin for 5 min. The supernatant is separated from the resin by centrifugation, replaced by 500 µl of 200 mM imidazole. Imidazole causes elution of polyhistidine-tag bearing proteins. To promote protein stability at their optimum pH, the buffer has been modified.

The method used to measure the concentration of proteins in solution is based on the Bradford method. The Protein assay reagent sold by BioRad is diluted to %, the reaction mixture comprises 160 reagent and 40 diluted eluate (to $\frac{1}{10}^{th}$ and to $\frac{1}{20}^{th}$). A standard range is made with BSA from 12.5 to 100 µg/ml.

D. Enzymatic Tests.

All the enzymes have been tested in 100 mM Tris, pH 7.5, 10 mM $MgCl_2$, at 37° C. The co-factors and activators have been added if necessary.

The enzymes *Saccaromyces cerevisiae* hexokinase (Hxk), *Escherichia coli* transketolase (Tkt), *Escherichia coli* pyruvate kinase (PK) and *Escherichia coli* lactate dehydrogenase (LDH), triose-phosphate isomerase (Tpi) and glycerol-3-phosphate dehydrogenase (G3PDH) have been ordered to Sigma. The *Escherichia coli* phosphoglucose isomerase (Pgi) is from Megazyme.

All the enzymatic substrates have been bought to Sigma-Aldrich. The enzymatic tests are coupled to a redox reaction with as a co-factor, NADH which absorbs ultraviolet with a 340 nm peack with a coefficient of molar extinction of 6 220 $M^{-1} \cdot cm^{-1}$. The Bio Tek Epoch 2 spectrophotometer has been used for UV reaction monitoring.

Measurement of the aldehyde dehydrogenase (AldA) activity: this activity has been measured in the presence of 5 mM glycoaldehyde, 3 mM $NAD^+$ and 3 mM ATP. For one molecule of glycoaldehyde oxidised into glycolate, one $NAD^+$ molecule is reduced into NADH.

Measurement of the fructose-6P aldolase (FSA) activity: the enzyme FSA cleaves D-arabinose-5-phosphate into glycolaldehyde and glyceraldehyde-3-phosphate (GAP). The glycolaldehyde rate of appearance has been measured in the presence of AldA with 2 mM $NAD^+$. To monitor GAP appearance, TPI and G3PDH have been added, in the presence of 0.4 mM NADH.

Measurement of the D-arabinose-5-phosphate isomerase (KdsD) activity: D-arabinose-5-phosphate isomerase catalyses the interconversion of D-ribulose-5-phosphate into D-arabinose-5-phosphate. The KdsD activity on D-ribulose-5-phosphate has been determined by adding FSA, aldA in excess in the presence of 3 mM $NAD^+$.

Figure 5A:
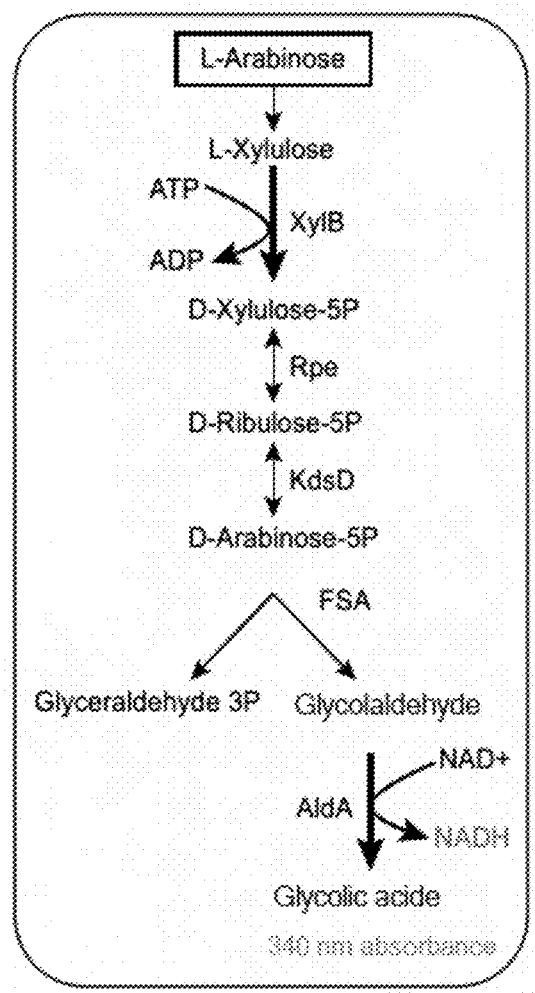
FIG. 5 shows the system comprising 6 purified enzymes (XylA, XylB, RPE, KdsD, FSA, AldA) which are capable of converting D-xylose into glycolic acid (FIG. 5A). The glycolic acid production with this system in the presence of D-xylose has been compared with that with a system not having XylA; the enzymatic reaction is based on the NADH assay at 340 nm (FIG. 5B).

In vitro conversion of D-xylose into glycolic acid: the conversion of D-xylose into glycolic acid requires XylA, XylB, Rpe, KdsD, FSA and aldA (FIG. 5A). The conversion of D-xylose into glycolic acid is demonstrated in a reaction mixture containing 100 mM Tris HCl pH 7.5, 10 mM $MgCl_2$, 0.5 mM $MnCl_2$, 3 mM ATP, 2 mM $NAD^+$, 1-10 µg of each enzyme and 5 mM D-xylose.

Figure 4A:
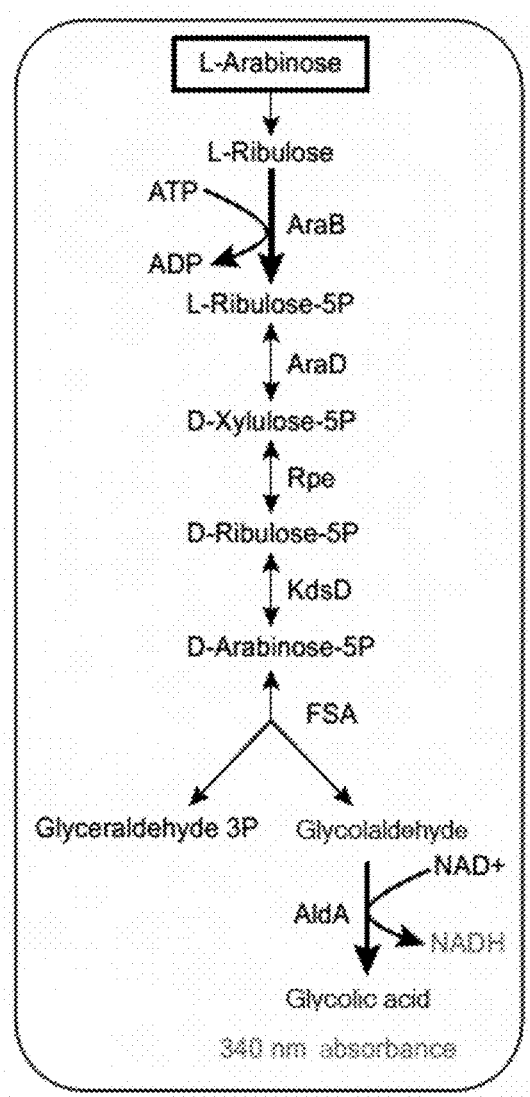
FIG. 4 shows the system comprising 7 purified enzymes (AraA, AraB, AraD, RPE, KdsD, FSA, AldA) which catalyse the conversion of L-arabinose into glycolic acid (FIG. 4A). The glycolic acid production with this system in the presence of L-arabinose has been compared with that of a system not having AraA; the enzymatic reaction is based on the NADH assay at 340 nm (FIG. 4B).

In vitro conversion of L-arabinose into glycolic acid: the conversion of L-arabinose into glycolic acid requires AraA, AraB, AraD, Rpe, KdsD, FSA and aldA (FIG. 4A). The conversion of L-arabinose into glycolic acid is demonstrated in 100 mM Tris HCl, pH7.5, 10 mM $MgCl_2$, 0.5 mM $MnCl_2$, 3 mM ATP, 2 mM $NAD^+$, 1-10 µg of each enzyme and 5 mM L-arabinose.

Figure 6A:
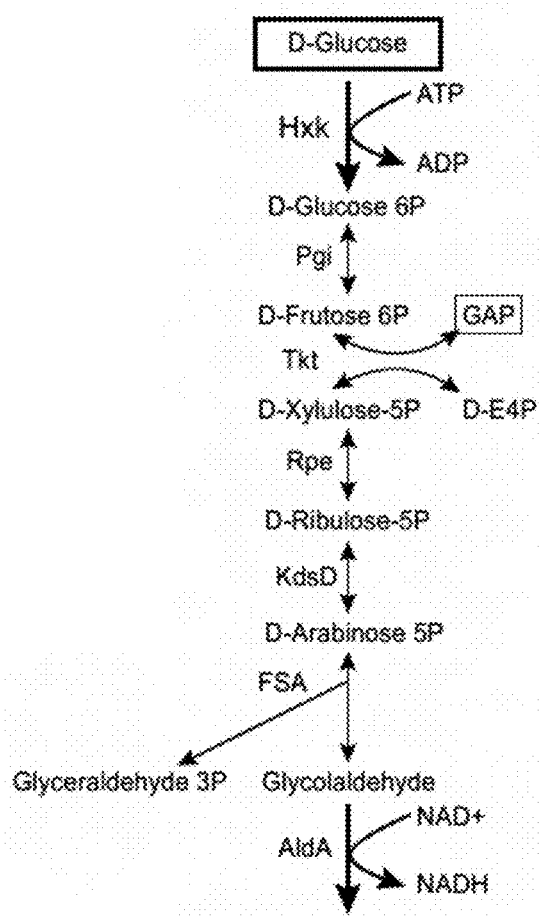
FIG. 6 shows the system comprising 7 purified enzymes (Hxk, Pgi, Tkt, RPE, KdsD, FSA, AldA) which are capable of converting D-glucose into glycolic acid (FIG. 6A). The glycolic acid production with this system in the presence of D-glucose has been compared with that with a system not having Hxk; the enzymatic assay is based on the NADH assay at 340 nm (FIG. 6B).

In vitro conversion of D-glucose into glycolic acid: The conversion of D-glucose into glycolic acid requires the enzymes Hxk, Pgi, Tkt, Rpe, KdsD, FSA and aldA (FIG. 6A). The proof of concept is made in 100 mM Tris HCl, pH 7.5, 10 mM $MgCl_2$, 0.5 mM $MnCl_2$, 1 mM TPP ("Thiamine Pyrophosphate"), 3 mM ATP, 2 mM NAD, 5 mM Glyceraldehyde-3P, 1-10 µg of each enzyme and 5 mM D-glucose.

I.2. Results.

A. In vitro conversion of D-ribulose-5P into glycolic acid.

Figure 3:
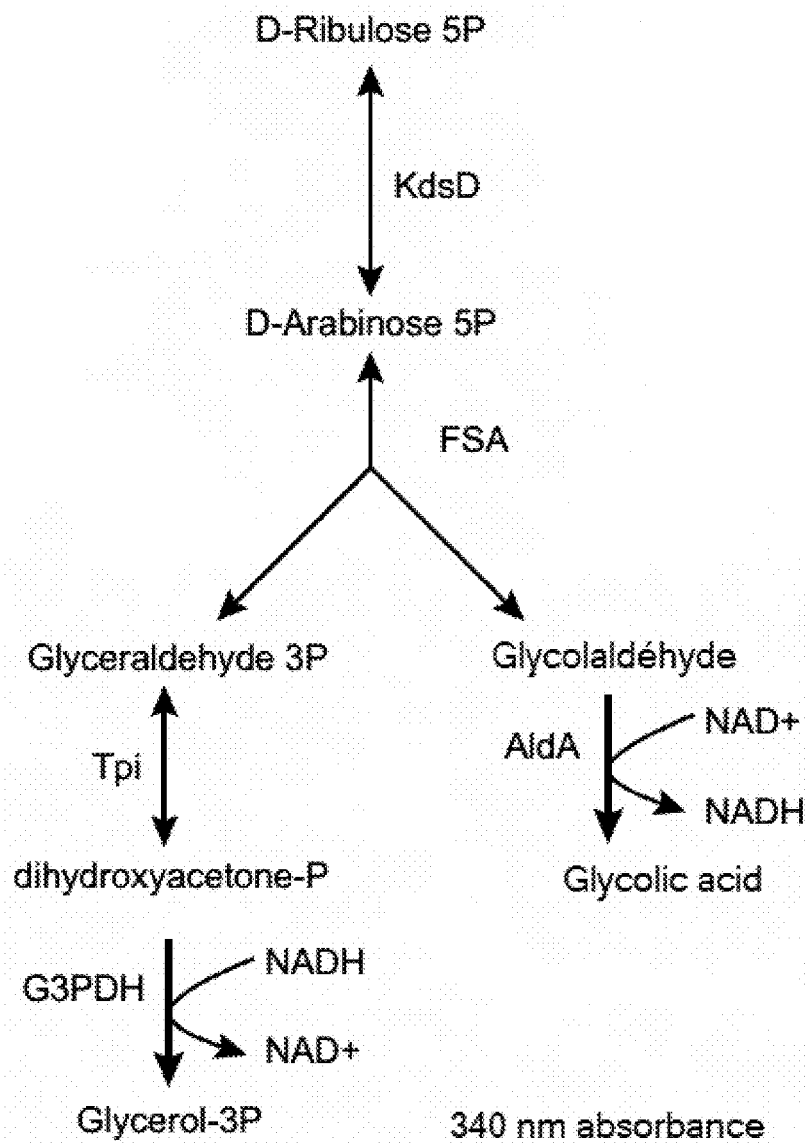
FIG. 3 is a schematic representation of the enzymatic test for checking arabinose-5P isomerase (KdsD), fructose-6P aldolase (FSA) and aldehyde dehydrogenase (aldA) activity. KdsD, FSA and aldA have been purified, triose phosphate isomerase (Tpi) and glycerol-3P dehydrogenase (G3PDH) have been ordered to Sigma.

Ribulose-5P is a metabolite common to the catabolism of arabinose, xylose and glucose in *Escherichia coli*. The non-natural conversion pathway of D-ribulose-5P into glycolic acid being the object of the present invention consists of the enzymes KdsD (D-arabinose 5P isomerase), FSA (Fructose-6P aldolase) and AldA (glycolaldehyde dehydrogenase). The in vitro proof of concept consisted in reconstructing this pathway with purified enzymes in an adapted buffer. First, aldA has been characterised on glycolaldehyde, and then the FSA activity on D-arabinose-5P has been checked by coupling with aldA in order to check glycolaldehyde formation and by coupling with triose phosphate isomerase and glycerol-3P dehydrogenase to highlight glyceraldehyde-3P synthesis (FIG. 3). The FSA activity measurements obtained by these 2 methods are identical. Finally, the KdsD activity on D-ribulose-5P has been measured by coupling with the excess enzymes FSA and aldA. This last enzymatic test enabled KdsD functionality to be checked and the entire glycolic acid synthesis pathway to be reconstituted. NADH is produced in an equimolar amount with glycolic acid. In order to check that NADH is really a glycolic acid production witness, the glycolic acid production has been measured by HPLC.

The catalytic constants of these 3 enzymes are shown in Table 6. Polyhistidine-tagged proteins KdsD, FSA and aldA are active. The reaction mixture containing KdsD, FSA and AdA in the presence of 5 mM of D-ribulose-5P has been analysed by HPLC, 1.5 mM of glycolic acid has been quantified. The glycolic acid production measured corresponds to the initial $NAD^+$ amount in the reaction mixture, indicating that the reaction has been completed.

TABLE 6 catalytic constants of polyhistidine-tagged arabinose-5P
isomerase (KdsD), fructose-6P aldolase
(FSA), aldehyde dehydrogenase (AldA)

| Enzyme | Substrate | Km (mM) | Vmax (U mg$^{-1}$) | Vmax/Km (.10$^{-6}$) (min$^{-1}$ mg$^{-1}$) |
|---|---|---|---|---|
| KdsD-His | D-ribulose-5P | 1.34 ± 0.12 | 1.14 ± 0.17 | 850 |
| FSA-His | D-arabinose-5P | 0.652 ± 0.15 | 0.26 ± 0.09 | 398 |
| aldA-His | glycolaldehyde | 0.21 ± 0.05 | 1.16 ± 0.31 | 5 552 |

B. Conversion of L-Arabinose or D-Xylose or D-Glucose into Glycolic Acid.

The enzymes catalyzing the conversion of L-arabinose, D-xylose and D-glucose into glycolic acid have been purified (AraA, AraB, AraD, XyA, XyB, Rpe, KdsD, Fsa, AldA) or ordered (Tkt, Glk, Pgi) in order to proof the concept of the glycolic acid production from these 3 substrates in vitro.

i. Conversion of L-Arabinose into Glycolic Acid.

Figure 4B:
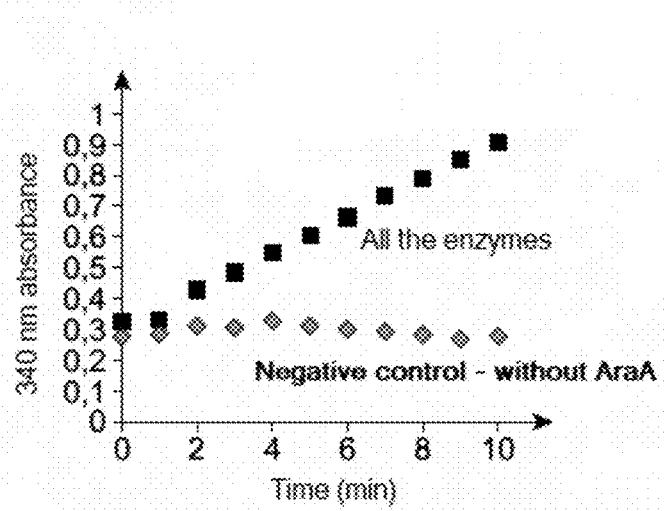

The conversion of L-arabinose into glycolic acid and glyceraldehyde 3P is catalysed by AraA, araB, araD, Rpe, KdsD, FSA and aldA (FIG. 4A). The NADH synthesis observed during the enzymatic test in the presence of L-arabinose is the indirect witness of glycolic acid production (Table 7, FIG. 4B).

The conversion of L-arabinose into glycolic acid is demonstrated and this metabolic pathway is thus thermodynamically possible.

TABLE 7 enzymatic activity measured for the conversion of L-arabinose
into glycolic acid at 340 nm, 37° C.. An enzymatic
activity unit (U) is defined as the conversion
of one micromole of substrate per minute.
The negative control is devoid of arabinose
isomerase activity catalysed by AraA.

| Substrate (5 mM) | Enzymes | Activity (U) |
|---|---|---|
| L-arabinose | AraA, AraB, AraD, Rpe, KdsD, FSA, AldA | 11.59 |
| | AraB, AraD, Rpe, KdsD, FSA, AldA | 0.00 | ii. Conversion of D-Xylose into Glycolic Acid.

Figure 5B:
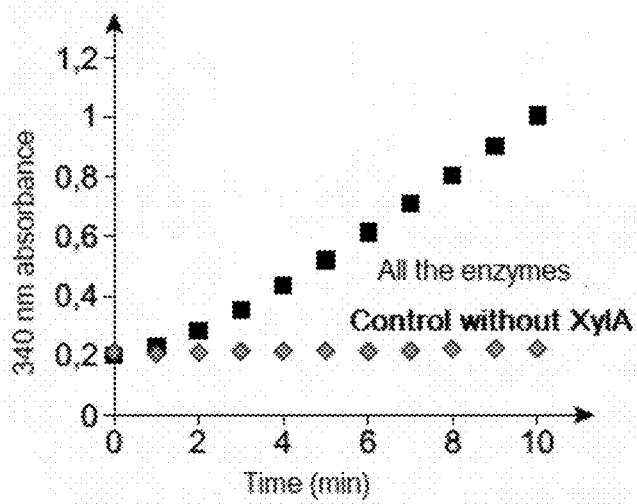

The conversion of D-xylose into glycolic acid and glyceraldehyde 3P is catalysed by XylA, XylB, Rpe, KdsD, FSA and AldA (FIG. 5A). When these enzymes are contacted with D-xylose, D-xylose is converted into glycolic acid in vitro as evidenced by NADH production (FIG. 5B, Table 8).

TABLE 8 enzymatic activity measured for the conversion of D-xylose into
glycolic acid at 340 nm, 37° C.. An enzymatic
activity unit (U) is defined as the conversion of
a micromole of substrate per minute. The negative
control is devoid of xylulose isomerase
activity catalysed by XylA.

| Substrate (5 mM) | Enzyme(s) | Activity (U) |
|---|---|---|
| D-xylose | XylA, XylB, Rpe, KdsD, FSA, AldA | 15.07 |
| | XylB, Rpe, KdsD, FSA, AldA | 0.00 |

The conversion pathway of D-xylose into glycolate is functional and thermodynamically possible.

iii. Conversion of D-Glucose into Glycolic Acid.

Figure 6B:
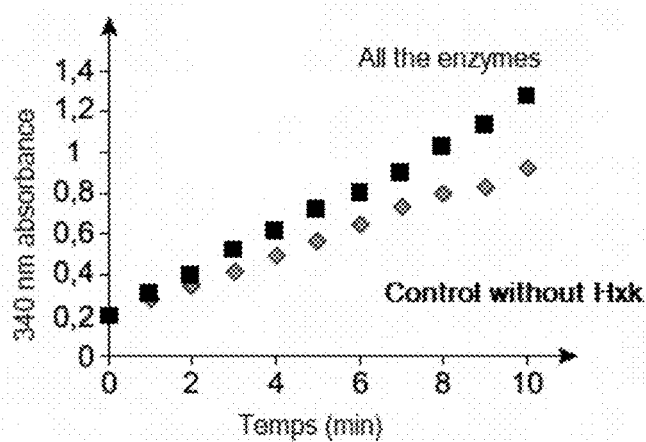

The conversion of D-glucose into glycolic acid has been demonstrated by contacting D-glucose and DL-glyceraldehyde-3P (GAP) with Hxk, Pgi, Tkt, Rpe, KdsD, FSA and AdA (FIG. 6A). The negative control shows a significant activity (FIG. 6B, Table 9). GAP is a relatively instable molecule, it is thereby dephosphorylated spontaneously into glyceraldehyde. Baldoma et al. (1987) have demonstrated that Escherichia coli AldA was active on glycolaldehyde, lactaldehyde, methylglyoxal and L-glyceraldehyde [13]. NADH synthesis in the negative control is therefore not correlated with synthesis of glycolate but of glycerate from glyceraldehyde oxidation. This secondary activity is not relevant in vivo, especially as L-glyceraldehyde is not formed in Escherichia coli.

TABLE 9 enzymatic activity measured for the conversion of D-glucose into
glycolic acid at 340 nm, 37° C.. An enzymatic
activity unit is defined as the conversion of
1 micromole of substrate per minute. The negative control
is devoid of hexokinase (Hxk) activity.

| Substrates (5 mM) | Enzymes | Activity (U) | Corrected activity (U) |
|---|---|---|---|
| D-glucose, GAP | Hxk, Pgi, Tkt, Rpe, KdsD, Fsa, AldA | 23.5 | 6.2 |
| | Pgi, Tkt, Rpe, KdsD, Fsa, AldA | 17.3 | |

From these results, the conversion pathway of D-glucose into glycolic acid is functional in vitro and is thus thermodynamically favourable.

The carbohydrates L-arabinose, D-xylose and D-glucose are naturally assimilated and converted into D-ribulose-5P in Escherichia coli, the non-natural conversion of D-ribulose-5P into glycolic acid allowed by the overexpression of KdsD, FSA and aldA has been demonstrated. The implementation of the non-natural pathway KdsD-FSA-aldA is thermodynamically favourable, the complete assimilation and conversion pathways of the reconstructed pentoses and hexose enabled glycolic acid to be synthetised in vitro.

However, the in vitro demonstration is by definition isolated from the E. coli natural metabolism, these results do not take into account reactions involving intermediates, transmembrane transport efficiency of the substrates and glycolic acid excretion, co-factor availability, . . . . A complementary in vivo proof of concept has been made to enhance these preliminary results.

II. In Vivo Proof of Feasibility.

II.1. Material and Methods.

A. Construction of Plasmids.

i. Choice of the Vectors

The series of vectors pZ (Expressys) has the advantage of being modulable: it is easy to change the replication origin, resistance marker and vector promoter by restriction/ligation.

Vectors pZA23, pZA33, pZE23 and pZS23 have the promoter PA1/ac0-1 which is a promoter derived from the lactose operon promoter comprising the operator o. PA1lac0-1 is under the control of the repressor lacI: in its active form, the repressor lacI is linked to the operator o and inhibits the transcription whereas, when complexed with IPTG, it changes conformation and is no longer capable to be bound to the site o, whereby the transcription becomes possible. The promoter PA1lac0-1 is said to be IPTG-inducible. Even if E. coli naturally has a lacI gene copy in its genome upstream of the operon lac, most of the IPTG-inducible bacterial expression vectors bear the lac gene in order to ensure full inhibition of the transcription of genes which are under its dependence. The vectors pZ have the feature to have a lightened structure of the lacI gene which provides them with a small size (2 358 to 3 764 bp).

Modifications have been provided to the vector pZA33, the promoter PA1/ac0-1 has been replaced by the constitutive promoter proD and by the inducible promoter Ptac, generating the vectors pZA36 and pZA38 respectively. The promoter PA1/ac0-1 of pZS23 has been modified by the promoter proD generating the vectors pZS27.

ii. Cloning Method: HiFi Assembly

The HiFi Assembly® (NEB) method has been retained to construct the vectors used hereinafter. This method enables several fragments to be assembled. It has been validated for fragments with different sizes with variable overlapping regions (15-80 bp). In a single step, the fragments can be assembled, it is a method commonly used for its simplicity and flexibility.

The commercial mixture provided by New England Biolabs contains different enzymes: (a) an exonuclease which creates 3' single strand ends, which facilitates assembly of the fragments which share a sequence complementarity; (b) a polymerase which fills the empty spaces after the fragments have been assembled; and (c) a ligase which links fragments together.

The genes of the glycolic acid production synthetic pathway according to the invention kdsD, fsa and aldA have been amplified by PCR from the genome DNA extracted from E. coli K12 MG1655 and inserted by HiFi Assembly® into the vectors pZ, linearised beforehand by PCR with primers hybridising on either side of the MCS. All the plasmids have been checked by sequencing before use.

iii. Expression Vectors for the Overexpression of kdsD, Fsa, aldA

The vectors used for the overexpression of kdsD,fsa and aldA are shown in Table 10 hereinafter.

TABLE 10

| Name | Description | Source |
|---|---|---|
| pZA23 | Kan $^R$, ori p15A, PA1lac0-1 | Expressys |
| pZA33 | Chm$^R$, ori p15A, PA1lac0-1 | Expressys |
| pZS23 | Kan $^R$, ori pSC101, PA1lac0-1 | Expressys |
| pZA36 | Chm $^R$, ori p15A, Ptac | This study |
| pZA37 | Chm $^R$, ori p15A, proC | This study |
| pZS28 | Kan $^R$, ori pSC101, proD | This study |
| pEXT20 | AmpR, ori ColE1, Ptac | [33] |
| pET28a | Kan 11, ori ColE1, Ptac | Novagen |
| pKF3 | pZA36 kdsD fsa | This study |
| pA4 | pZS23 aldA | This study |
| pKF5 | pZA37 kdsD fsa | This study |
| pA8 | pZS28 aldA | This study |

B. Construction of the Strains.

i. Deletions of the Genes

The deletions have been made by transduction, using the phage P1vir. The preparation of the lysates P1vir and the transduction procedures have been made as described previously with little modifications [34].

Thus, the strains KEIO bearing a single deletion and a kanamycin antibiotic-resistance cassette (donor strain) have been infected with P1vir and high-titer lysates λ have been obtained [35]. The donor strains (KEIO) have been cultured overnight in LB at 37° C. The day after, 5 ml of LB containing 0.2% glucose and 5 mM CaCl$_2$) have been inoculated with 200 of the donor strain and cultured for 30 min at 37° C. Then, 100 of P1vir lysate (~5×10$^8$ phages/ml) have been added to each donor culture and incubated again at 37° C. for 2 to 3 hours until the culture was clear and the cells were completely lysed. The lysates have been filtered by using 25 mm sterile syringe filters with a 0.2 m support membrane (Pall) and preserved at 4° C.

The strain to be deleted (receiving strain) has been infected with P1vir containing a donor gene deletion cassette having a kanamycin resistance. For this, the receiving strain has been cultured in 5 ml LB medium at 37° C. The cells have been centrifuged at 1 500 g for 10 min and re-suspended in 1.5 ml of 10 mM MgSO$_4$ and 5 mM CaCl$_2$. Lysate from the donor strain (0.1 ml) is added to the cellular suspension which is incubated for 30 min. Then, 0.1 ml of 1M sodium citrate is added to the cell and P1vir mixture. Then, 1 mL LB is added to the homogenised suspension before an incubation of 1h at 37° C., 200 rpm.

The cellular suspensions are spread on a solid LB medium with the appropriate antibiotic then the colonies are screened by PCR to highlight successful transduction events.

To remove the antibiotic cassette, the cells have been transformed with a plasmid pCP20 bearing the FLP recombinase. Each step has been checked by PCR. When the deleted strain is sensitive to kanamycin after removing the cassette, it can again be used as a receiving strain in order to add a new deletion from a new phage lysate.

ii. Preparation of Competent Bacteria and Transformation

The competent non-commercial strains are prepared according to the protocol of Chung et al, 1989, which is slightly modified [36]. A pre-culture is made in LB overnight to inoculate the day after a fresh LB culture at a OD$_{600}$ of 0.1. When the OD$_{600}$ reaches 0.3-0.5 (the bacteria can be made competent up to a OD$_{600}$ of 1), an amount of cellular culture equivalent to a OD$_{600}$ unit is sampled and centrifuged (8 000 rpm, 2 min). The supernatant is removed whereas the pellet is up taken in 300 TSS buffer (2.5%$_{(wt/vol)}$ PEG 3350, 1 M MgCl$_2$, 5%$_{(vol/vol)}$ DMSO). The mixture is incubated for 10 min on ice. The plasmid can then be added to the competent cells. After 30 further minutes of ice incubation, a heat shock is made at 42° C. for 90 seconds. The cells transformed are put on ice for 10 min. 400 LB are added and the culture is incubated at 200 rpm for 1 h, at an adapted temperature (the temperature can not exceed 30° C. in the case of a transformation with a plasmid the replication origin of which is thermosensitive). The bacterial culture is centrifuged at 8 000 rpm for 2.5 min. 600 of supernatant are removed, the remaining volume is inoculated on a solid LB dish with the appropriate antibiotic.

iii. Strains for Glycolic Acid Production

The E. coli strains used in this study are listed in Table 11 hereinafter.

TABLE 11

| Strain | Genotype | Reference |
|---|---|---|
| MG1655 | F-λ-ilvG- rfb-50 rph-1 | ATCC 407076 |
| NEB5 | fhuA2 Δ(argF-lacZ)U169 phoA glnV44 f80 Δ(lacZ)M15 gyrA96 recA1 relA1 endA1 thi-1 hsdR17 | NEB |
| BL21 (DE3) | huA2 [Ion] ompT gal (λ DE3) [dcm] ΔhsdS) | NEB |
| Screen00 | MG1655 ΔtktA ΔtktB ΔglcD | This study |
| Screen09 | Screen00 containing pZA36 kdsD fsa (pKF3) and pZS23 aldA (pA4) | This study |
| Screen23 | Screen00 containing pZA37 kdsD fsa (pKF5) and pZA28 aldA (pA8) | This study |
| WC3G gapA- | W3CG F-, LAM-, gapA 10::Tn10, IN(rrnD-rrnE), rph-1 | [37] |
| BW25113 | F-, Δ(araD-araB)567, ΔlacZ4787(::rrnB-3), λ-, yrph-1, Δ(rhaD-rhaB)568, hsdR514 | [26] |

TABLE 11-continued

| Strain | Genotype | Reference |
| --- | --- | --- |
| JW2771 | BW25113 ΔfucA | [26] |
| JW4364 | BW25113 ΔarcA | [26] |
| JW5129 | BW25113 ΔmgsA | [26] |
| JW2946 | BW25113 ΔglcD | [26] |
| JW2771 | BW25113 ΔfucA | [26] |
| JW3887 | BW25113 ΔpfkA | [26] |
| GA00 | WC3G gapA- ΔglcD ΔarcA ΔmgsA ΔfucA ΔpfkA proD galP | This study |
| GA09 | GA00 containing pZA36 kdsD fsa (pKF3) and pZS23 aldA (pA4) | This study |
| GA23 | GA00 containing pZA37 kdsD fsa (pKF5) and pZA28 aldA (pA8) | This study |

C. Media and Culture Conditions.

i. Composition of the Media

The cells are cultured on the LB medium for the molecular biology (cloning, deletions, transformation) steps. This rich medium is comprised of 10 g/L trypton, 5 g/L yeast extracts and 5 g/L NaCl. 15 g/L agar are added for obtaining a solid medium. The LB, with or without agar, is sterilised by autoclaving for 20 min at 110° C. before use.

The cultures for glycolic acid production are made in a mineral medium M9 (Table 12) containing a carbon source (glucose, xylose or arabinose) at a 10 g/L or 20 g/L concentration and LB traces in order to reduce the latency phase (2 g/L trypton, 1 g/L yeast extracts and 1 g/L NaCl).

TABLE 12 composition of the medium M9

| Compound | Final concentration (g/L) |
| --- | --- |
| $Na_2HPO_4 * 12 H_2O$ | 18 |
| $KH_2PO_4$ | 3 |
| NaCl | 0.5 |
| $NH_4Cl$ | 2 |
| $MgSO_4 * 7 H_2O$ | 0.5 |
| $CaCl_2 * 2 H_2O$ | 0.015 |
| $FeCl_3$ | 0.010 |
| Thiamine HCl | $6.10^{-3}$ |
| NaEDTA | $0.49.10^{-3}$ |
| $CoCl_2 * 6 H_2O$ | $1.8.10^{-3}$ |
| $ZnCl_2SO_4 * 7 H_2O$ | $1.8.10^{-3}$ |
| $Na_2MoO_4 * 2 H_2O$ | $0.4 .10^{-3}$ |
| $H_3BO_3$ | $0.1.10^{-3}$ |
| $MnSO_4 * H_2O$ | $1.2.10^{-3}$ |
| 1.2 mg/L $CuCl_2 * 2 H_2O$ | $1.2.10^{-3}$ |

For the strain MG1655 ΔtktA ΔtktB ΔglcD, the medium M9 with LB traces is complemented with 500 M L-phenylalanine, 250 µM L-tyrosine, 200 µM L-tryptophane, 6 µM p-aminobenzoate, 6 µM p-hydroxydenzoate and 280 µM shikimate. For the strains the glyceraldehyde-3-phosphate dehydrogenase activity of which has been removed, the medium has been completed with 0.4 g/L malic acid adjusted at pH 7 with KOH beforehand. The medium is buffered by adding 20 g/L 3-(N-morpholino)propanesuphonic acid (MOPS) at pH 7 and then filtered through 0.2 µm membranes to obtain a sterile medium. If need be, the appropriate antibiotics have been added to the medium (100 g/mL ampicillin, 50 µg/mL kanamycin, 25 µg/mL chloramphenicol). For the strains containing an IPTG inducible vector, a 0.1 mM IPTG final concentration is used. All the products have been ordered to Sigma. The cultures are placed in a stirrer (Infors) at 200 rpm, 37° C. for the experiment time. The culture growth is monitored by measuring the 600 nm optical density ($OD_{600}$) with a spectrophotometer (Biochrom Libra S11).

ii. Fermentation Process in 250 mL Baffle Erlenmeyer Flasks

Strains Containing Constituted Promoters

Protocol 1

The strains are uptaken from of a glycerol stock preserved at −80° C. in 10 mL LB, at 37° C. overnight. The pre-cultures are centrifuged the day after at 4 000 rpm for 5 min and re-suspended in 20 mL of M9 medium with 1% xylose or arabinose in 100 mL Erlenmeyer flasks. An adaptation phase with a 24h duration enables the strains to adapt to pentose use. The cells are then centrifuged (4 000 rpm, 5 min) and then uptaken under the final culture conditions: at an initial $OD_{600}$ of 0.5 in 50 mL medium with a composition identical to that used during the adaptation phase (M9 with 1% xylose or arabinose). 250 mL baffle culture flasks are used for an optimum oxygenation. The cultures are stirred at 200 rpm, at 37° C.

Protocol 2

The strain GA23 is uptaken from of a glycerol stock preserved at −80° C. in 10 mL LB containing the following antibiotics: tetracyclin (10 µg/mL), kanamycin (50 µg/ml) and chloramphenicol (25 g/ml). The pre-culture is incubated at 37° C., 200 rpm overnight. The process is decoupled into two phases: a growth phase dedicated to biomass production and a production phase dedicated to the production of glycolic acid. The growth phase is achieved in 50 mL of medium M9 to pH 7 containing 1.5 g/L xylose, 5 g/L succinate, 73 mg/L L L-methionine, 73 mg/L L-tryptophan and 1 g/L casaminoacids inoculated with pre-culture at an $OD_{600}$ of 0.2 in a 250 ml erlenmeyer. After 24h of culture at 37° C., 200 rpm, the cells are centrifuged, washed and recovered in 50 mL M9 at pH 7 containing 10 g/L lignocellulosic sugar (glucose, xylose or arabinose), 73 mg/L L-methionine, 73 mg/L L-tryptophan and 1 g/L casaminoacids in a 250 ml erlenmeyer. The medium used for production is devoid of succinate and does not allow growth, the source of carbon (glucose, xylose or arabinose) is used for the production of glycolic acid. The production phase lasts 48h at 37° C., 200 rpm, samples are taken regularly to measure pH, optical density and track sugar consumption and GA production by HPLC.

Strains Containing Inducible Promoters

The LB pre-cultures of the strains containing a vector with an inducible promoter are cultured at an initial $OD_{600}$ of 0.1 in 30 mL of M9 with 1% glucose. When the $OD_{600}$ reaches 0.6, 0.1 mM IPTG is added to induce gene expression under the control of the IPTG inducible promoter (plac or ptac). 24h after, the cells are centrifuged, a sterile water washing enables glucose traces to be removed, and they are re-suspended in 20 mL of the medium chosen from the study (M9 with 1% xylose or arabinose, 0.1 mM IPTG) for the adaptation phase. The rest of the culturing protocol is identical to that for the strains with constitutive promoters.

iii. Fermentation Process in a 2 L BIOSTAT® B Startorius Stedim Biotech Bioreactor Cultures of the previously described strain GA23 have been made in a 2 L bioreactor. The pre-cultures have been made in LB added with kanamycin, chloramphenicol and tetracyclin, cultured at 37° C., 200 rpm. A first 3 mL pre-culture has been made overnight, the same has been used for inoculating a second 15 mL pre-culture cultured for 24h. The same has been used for inoculating a third and last pre-culture in a 150 mL Erlenmeyer flask cultured for 8h. In the exponential phase, this last pre-culture has been used to inoculate the fermenter culture at a OD of 0.3. The M9 culture medium (Table 12) contains 10 g/L xylose or glucose, as well as LB (10%) and 0.4 g/L malic acid. The cultures have been made at 37° C., with stirring (300-1500 rpm) and venting maintaining dissolved oxygen above 20% of the air flow rate. The pH has been maintained at 7 with a KOH base solution. The culture has been conducted in a batch mode for 40h.

D. Measurements of the Concentrations of Extracellular Metabolites.

Sugar consumption and glycolic acid production are monitored by regularly sampling samples under sterile conditions which are centrifuged at 13 000 rpm for 5 min in a laboratory centrifuge (Eppendorf 5415D), filtered through a 0.2 μm filter and stored at −20° C. The measurement of extracellular metabolites is made by high performance liquid chromatography (HPLC) with an Ultimate 3000 chromatograph (Dionex, Sunnyvale, USA). The HPLC system is equipped with a cation exchange column (Aminex, HPX87H-300×7.8 mm, 9 μm, BioRad), an automatic injector (WPS-3000RS, Dionex), an IR detector (RID 10A, Shimadzu) and a UV detector (SPD-20A, Shimadzu). The mobile phase is a 1.25 mM sulfuric acid solution at a 0.5 mL/min flow rate. The samples are maintained at 4° C. and the injection of 20 is made in the column at 35° C.

II.2. Results Obtained with a Baffle Erlenmeyer Flask.

The inventors have demonstrated that the overexpression in *E. coli* of the 3 non-natural pathway enzymes according to the invention, i.e. arabinose-5-phosphate isomerase (KdsD), fructose-6-phosphate aldolase (FSA) and aldehyde dehydrogenase (AldA) is necessary and sufficient for synthesising glycolic acid from lignocellulosic monosaccharides.

A. With Pentoses as a Carbon Source.

Figure 7:
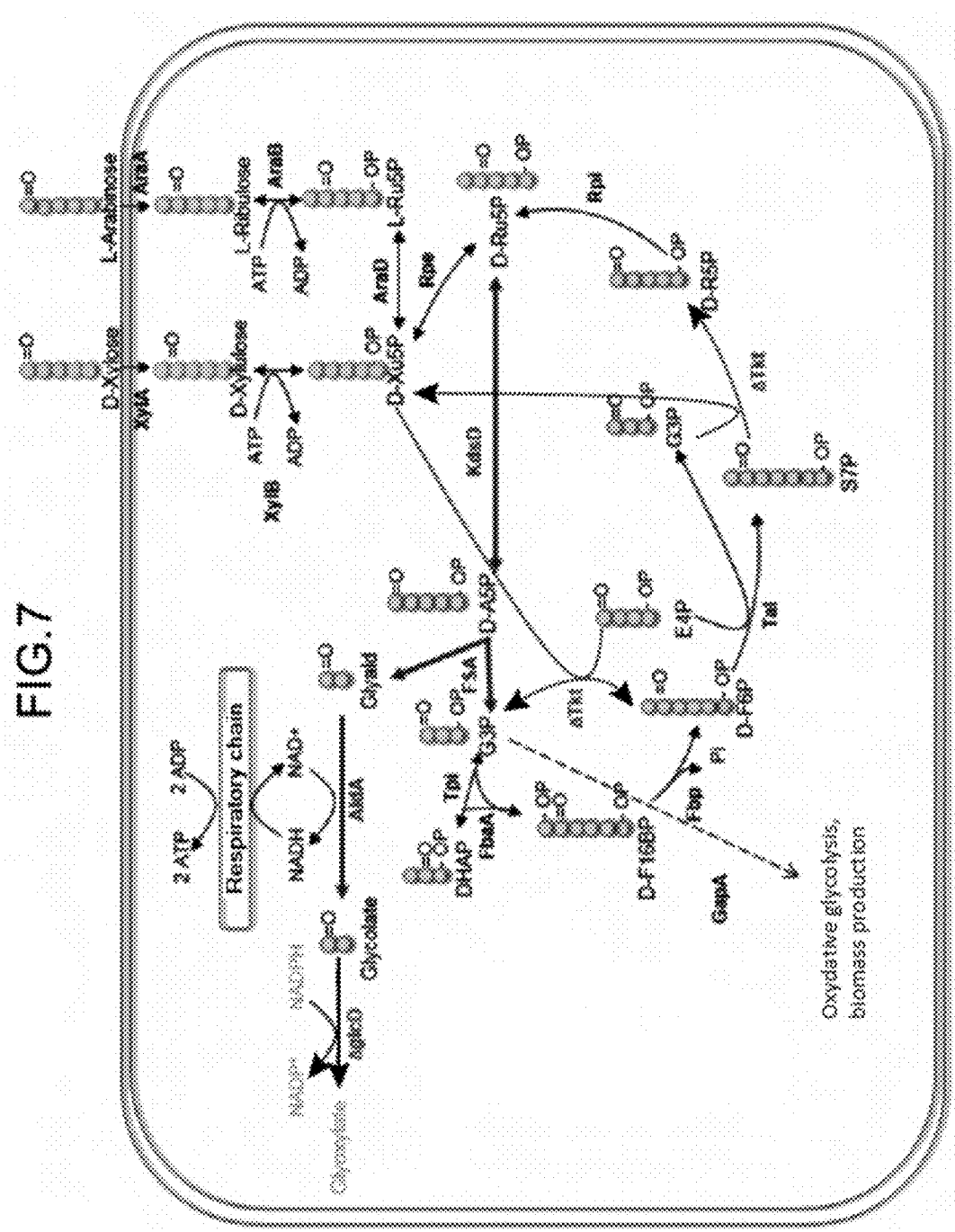
FIG. 7 shows the highlighting of the in vivo functionality of the non-natural pathway according to the invention in E. coli MG1655 ΔtktA ΔtktB ΔglcD, with in bold: the nonnatural pathway according to the invention, in dotted lines, the deletions. Xu5P: xylulose-5-phosphate, Ru5P: ribulose-5-phosphate, R5P: ribose-5-phosphate, S7P: sedoheptulose-7-phosphate, F6P: fructose-6-phosphate, F16BP: Fructose-1,6-bisphosphate, G6P: glucose-6-phosphate, DHAP: dihydroxyacetone phosphate, Glyald: glycolaldehyde, E4P: erythrose-4-phosphate, G3P: glyceraldehyde-3-phosphate.

To that end, a strain of *E. coli* K12 MG1655 deleted from genes tktA, tktB coding for transketolase has been constructed to highlight the functionality of the pathway according to the invention. Transketolase are major enzymes of the pentose phosphate pathway. In their absence, the growth on pentose is impossible, the intermediates pentose phosphate (D-ribose-5-phosphate and D-Xylulose-5-phosphate) are accumulated and can not be converted into glyceraldehyde-3phosphate for growth [38]. This strain needs the non-natural pathway according to the invention to grow from pentoses. Indeed, only the coupled activity of KdsD and FSA can generate glyceraldehyde-3-phosphate involved in glycolysis for the production of precursors necessary for growth [39]. Thus, a functional screen per growth test is contemplatable in which growth would be an indicator of the in vivo synthetic pathway efficiency (FIG. 7).

The 3 genes have been cloned as an operon and expressed in a strain of *E. coli* MG1655 ΔtktA ΔtktB ΔglcD. To that end, a two-vector expression system has been used, the latter has been accepted by the strain without generating detrimental modifications for the expression of the synthetic pathway according to the invention. The expression system of the synthetic pathway according to the invention thus includes a vector having a medium copy number bearing kdsD-fsa co-expressed with a vector with a low copy number bearing aldA.

Two expression systems have been studied, the first one with vectors with IPTG inducible promoters (pZA36 kdsD fsa and pZS23 aldA, expression system n° 9) and the other one with vectors with constitutive promoters (pZA37 kdsD fsa and pZS28 aldA, expression system n° 23).

Figure 8:
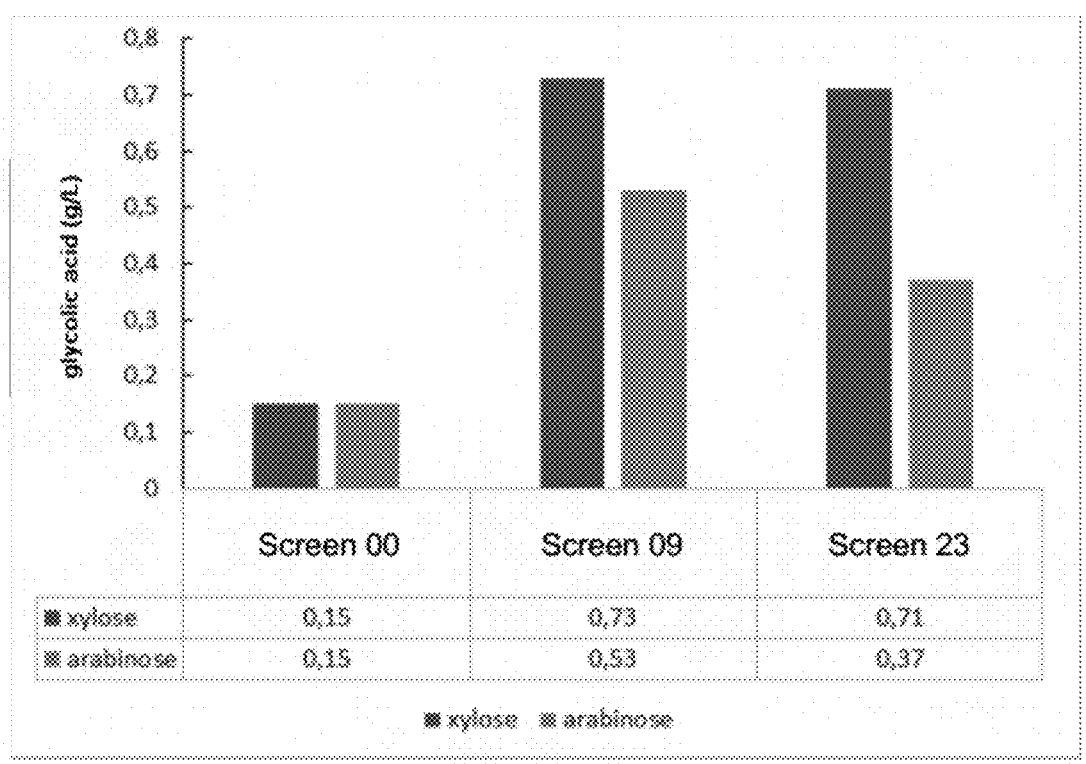
FIG. 8 shows the glycolic acid production of the E. coli strain MG1655 ΔtktA ΔtktB ΔglcD expressing the kdsD-fsa-aldA dependent non-natural pathway according to the invention from D-xylose or L-arabinose, at 37° C., 100h.

The cultures of the strains MG1655 ΔtktA ΔtktB ΔglcD expressing the systems 9 (Screen09) and 23 (Screen23) have been made at 37° C. and have shown a significant growth indicating that the overexpression of the kdsD and fsa genes is functional. HPLC analyses of the exometabolome of the bacterial cultures on L-arabinose and D-xylose have confirmed the presence of glycolic acid with both expression systems. This result demonstrates the feasibility of glycolic acid synthesis from pentoses by the in vivo synthetic pathway (FIG. 8). Table 13 hereinafter shows the glycolic acid yield from xylose and arabinose of the strains Screen09 and Screen23.

TABLE 13

| Strain | Glycolic acid/xylose (mol/mol) | Glycolic acid/arabinose (mol/mol) |
|---|---|---|
| Screen00 | 0.14 ± 0.03 | 0.14 ± 0.03 |
| Screen09 | 0.43 ± 0.02 | 0.32 ± 0.01 |
| Screen23 | 0.42 ± 0.02 | 0.20 ± 0.03 |

| Strain | Glycolic acid/xylose (g/g) | Glycolic acid/arabinose (g/g) |
|---|---|---|
| Screen00 | 0.07 ± 0.03 | 0.07 ± 0.03 |
| Screen09 | 0.22 ± 0.02 | 0.16 ± 0.01 |
| Screen23 | 0.21 ± 0.02 | 0.10 ± 0.03 |

B. With Pentoses and Hexoses as a Carbon Source.

The expression systems 9 and 23 have been transformed in the strain of *E. coli* WC3G ΔgapA ΔglcD ΔarcA ΔmgsA ΔfucA Δpkf proD-galP (GA00) designed for the glycolic acid production from hexoses and pentoses with an optimum carbon preservation, generating strains GA09 and GA23, respectively.

The bacterial cultures have been made in an Erlenmeyer flask at 37° C. on D-glucose, L-arabinose and D-xylose for 46h. The overexpression of the kdsD,fsa and aldA genes is necessary for glycolic acid production.

With Protocol 1 Such as Previously Defined

Figure 9:
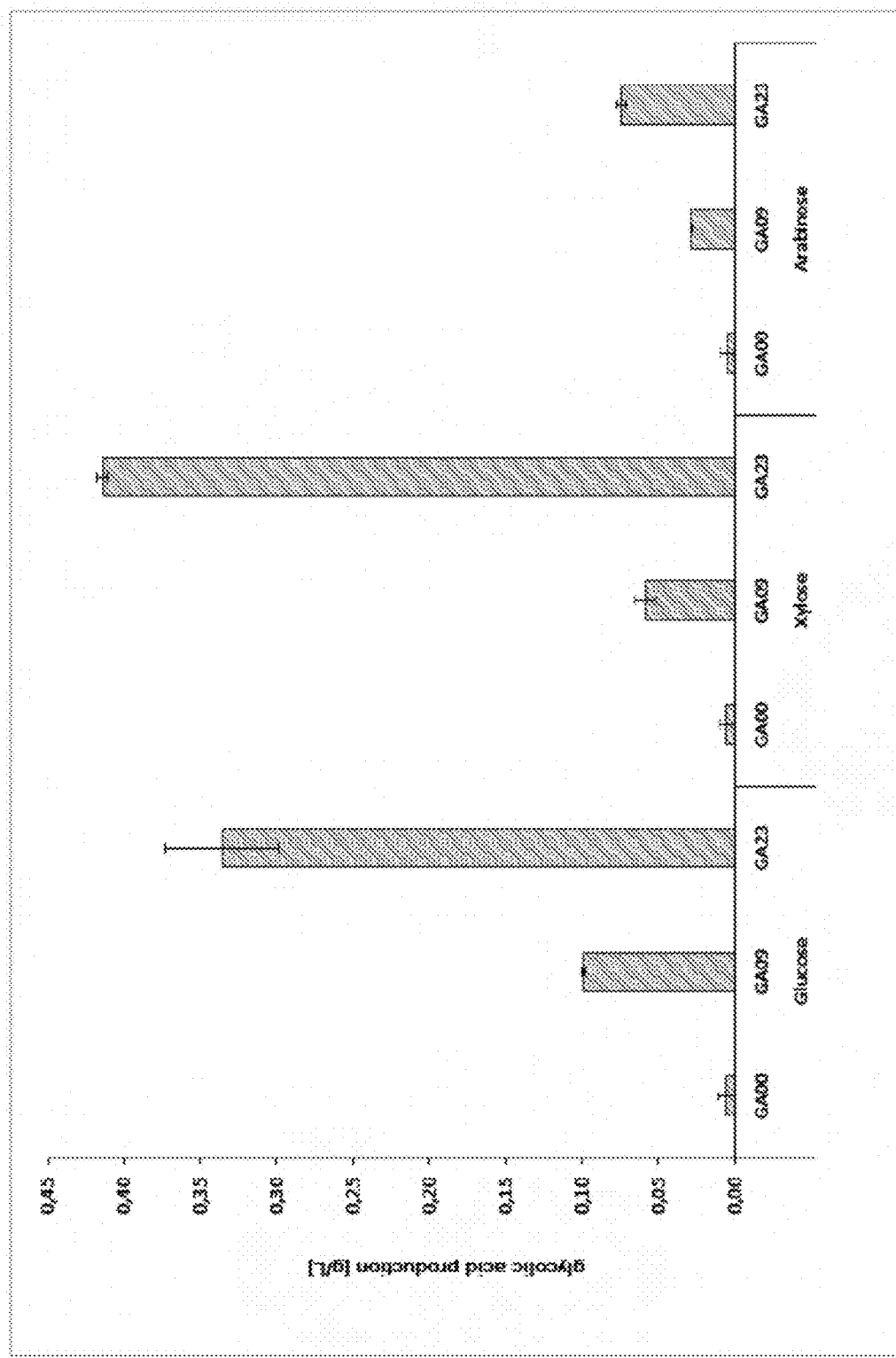
FIG. 9 shows the glycolic acid production of the strain of E. coli WC3G ΔgapA ΔglcD ΔarcA ΔmgsA ΔfucA Δpkf proD-galP expressing the kdsD-fsa-aldA dependent non-natural pathway according to the invention from glucose, xylose and arabinose, at 37° C., 50h.

The strain GA00 with the constitutive expression system n° 23 that is GA23 has shown a glycolic acid production from D-glucose (0.29 g/L), D-xylose (0.41 g/L) and L-arabinose (0.07 g/L). The glycolic acid production with the inducible expression system n° 9 that is GA09 is less significant on D-glucose (0.1 g/L), D-xylose (0.05 g/L) and L-arabinose (0.03 g/L) (FIG. 9). The expression system including constitutive promoters is favourable. The yield of the strain GA23 in glycolic acid is 0.09 g/g (0.21 mol/mol) from glucose, 0.18 g/g (0.36 mol/mol) from xylose and 0.16 g/g (0.32 mol/mol) from arabinose.

With protocol 2 such as previously defined

The yield of the strain GA23 in glycolic acid is 0.096 g/g (0.19 mol/mol) from glucose, 0.3 g/g (0.60 mol/mol) from xylose and 0.34 g/g (0.68 mol/mol) from arabinose.

REFERENCES

[1] Gädda et al, 2014, «The industrial potential of bio-based glycolic acid and polyglycolic acid», *Appita Journal*, vol. 67, pages 1-2.

[2] Kunze et al, 2006, «A central role for the peroxisomal membrane in glyoxylate cycle function», *Biochimica et Biophysica Acta—Molecular Cell Research*, vol. 1763, pages 1441-1452.

[3] International application WO 2007/141316 filed on behalf of Metabolic Explorer, published on 13 Dec. 2007.

[4] Deng, et al, 2018, «Balancing the carbon flux distributions between the TCA cycle and glyoxylate shunt to produce glycolate at high yield and titer in *Escherichia coli*», *Metabolic Engineering*, vol. 46, pages 28-34.

[5] International application WO 2017/09236 filed on behalf of Massachusetts Institute of Technology, published on 6 Apr. 2017.

[6] Pereira et al, 2016, «Efficient utilization of pentoses for bioproduction of the renewable two-carbon compounds ethylene glycol and glycolate», *Metabolic Engineering*, vol. 34, pages 80-87.

[7] International application WO 2016/079440 field on behalf of INRA, INSA and CNRS, published on 26 may 2016.

[8] Alkim et al, 2016, «The synthetic xylulose-1 phosphate pathway increases production of glycolic acid from xylose-rich sugar mixtures», *Biotechnology for Biofuels*, 9. doi: 10.1186/s13068-016-0610-2.

[9] Dugar and Stephanopoulos, 2011, «Relative potential of biosynthetic pathways for biofuels and bio-based products», *Nat Biotechnol*, vol. 29, pages 1074-1078.

[10] Bogorad et al, 2013, «Synthetic non-oxidative glycolysis enables complete carbon conservation», *Nature*, vol. 502, pages 693-697.

[11] Meredith and Woodard, 2006, «Characterization of *Escherichia coli* D-arabinose 5-phosphate isomerase encoded by kpsF: implications for group 2 capsule biosynthesis», *Biochemical Journal*. doi: 10.1042/BJ20051828.

[12] Garrabou et al, 2009, «Asymmetric self- and cross-aldol reactions of glycolaldehyde catalysed by d-fructose-6-phosphate aldolase», *Angewandte Chemie—International Edition*, vol. 48, pages 5521-5525.

[13] Baldomh and Aguilar, 1987, «Involvement of lactaldehyde dehydrogenase in several metabolic pathways of *Escherichia coli* K12», *The Journal of biological chemistry*, vol. 262, pages 13991-13996.

[14] Schurmann and Sprenger, 2001, «Fructose-6-phosphate aldolase is a novel class I aldolase from *Escherichia coli* and is related to a novel group of bacterial transaldolases». *Journal of Biological Chemistry*, vol. 276, pages 11055-11061.

[15] Szekrenyi et al, 2014, «Engineering the donor selectivity of D-fructose-6-phosphate aldolase for biocatalytic asymmetric cross-aldol additions of glycolaldehyde», *Chemistry—A European Journal*, vol. 20, pages 12572-12583.

[16] Ward et al, 1999, «Expression of prokaryotic membrane transport proteins in *Escherichia coli*», *Biochemical Society Transactions*, vol. 27, pages 893-899.

[17] Lu et al, 2012, «Combinatorial modulation of galP and glk gene expression for improved alternative glucose utilization», *Applied Microbiology and Biotechnology*, vol. 93, pages 2455-2462.

[18] Hernandez-Montalvo et al, 2003, «Expression of galP and glk in a *Escherichia coli* PTS mutant restores glucose transport and increases glycolytic flux to fermentation products», *Biotechnology and Bioengineering*, vol. 83, pages 687-694.

[19] Snoep et al, 1994, «Reconstitution of glucose uptake and phosphorylation in a glucose-negative mutant of *Escherichia coli* by using *Zymomonas mobilis* genes encoding the glucose facilitator protein and glucokinase», *J. Bacteriol.*, vol. 176, pages 2133-2135.

[20] Garcia et al, 2001, «Characterization of sugar mixtures utilization by an *Escherichia coli* mutant devoid of the phosphotransferase system», *Applied Microbiology and Biotechnology*, vol. 57, pages 186-191.

[21] Lord, 1972, «Glycolate oxidoreductase in *Escherichia coli*», *BBA—Bioenergetics*, vol. 267, pages 227-237.

[22] Alexeeva et al, 2003, «Requirement of ArcA for redox regulation in *Escherichia coli* under microaerobic but not anaerobic or aerobic conditions», *J Bacteriol.*, vol. 185, pages 204-209.

[23] Pellicer et al, 1999, «A mutational study of the ArcA-P binding sequences in the aldA promoter of *Escherichia coli*», *Molecular and General Genetics*, vol. 261, pages 170-176.

[24] Liu and De Wulf, 2004, «Probing the ArcA-P Modulon of *Escherichia coli* by Whole Genome Transcriptional Analysis and Sequence Recognition Profiling», *Journal of Biological Chemistry*, vol. 279, pages 12588-12597.

[25] Cho et al, 2006, «Transcriptional regulation of the fad regulon genes of *Escherichia coli* by ArcA», *Microbiology*, vol. 152, pages 2207-2219.

[26] Saadat and Harrison, 1998, «Identification of catalytic bases in the active site of *Escherichia coli* methylglyoxal synthase: Cloning, expression, and functional characterization of conserved aspartic acid residues», *Biochemistry*, vol. 37, pages 10074-10086.

[27] Atkinson and Walton, 1965, «Kinetics of regulatory enzymes *Escherichia coli* phosphofructokinase», *The Journal of Biological Chemistry*, vol. 240, pages 757-764.

[28] Ghalambor and Heath, 1962, «The metabolism of L-Fucose», *The Journal of Biological Chemistry*, vol. 237, pages 2427-2433.

Banerjee and Fraenkel, 1972, «Glucose-6-phosphate dehydrogenase from *Escherichia coli* and from "high level" mutant», J. bacteriol., vol. 110, pages 155-160.

[30] Gardner and Fridovich, 1991, «Superoxide sensitivity of the *Escherichia coli* aconitase», *Journal of Biological Chemistry*, vol. 266, pages 19328-19333.

[31] Fong et al, 2000, «Directed evolution of D-2-keto-3-deoxy-6-phosphogluconate aldolase to new variants for the efficient synthesis of D- and L-sugars», *Chemistry and Biology*, vol. 7, pages 873-883.

[32] Jørgensen et al, 2007, «Enzymatic conversion of lignocellulose into fermentable sugars: Challenges and opportunities», *Biofuels, Bioproducts and Biorefining*, vol. 1, pages 119-134.

[33] Dykxhoorn et al, 1996, «A set of compatible tac promoter expression vectors», *Gene*, vol. 177, pages 133-136.

[34] Bremer et al, 1984, «λ placMu: A transposable derivative of bacteriophage lambda for creating lacZ protein fusions in a single step», *Journal of Bacteriology*, vol. 158, pages 1084-1093.

[35] Baba et al, 2006, «Construction of *Escherichia coli* K-12 in-frame, single-gene knockout mutants: The Keio collection», *Molecular Systems Biology*, 2. doi: 10.1038/msb4100050.

[36] Chung et al, 1989, «One-step preparation of competent *Escherichia coli*: transformation and storage of bacterial cells in the same solution», *Proceedings of the National Academy of Sciences*, vol. 86, pages 2172-2175.

[37] Ganter et Pliickthun, 1990, «Glycine to alanine substitutions in helices of glyceraldehyde-3-phosphate dehydrogenase: effects on stability», *Biochemistry*, vol. 29, pages 9395-2402.

[38] Teleman et al, 1999, «Identification and quantitation of phosphorus metabolites in yeast neutral pH extracts by nuclear magnetic resonance spectroscopy», *Analytical Biochemistry*, vol. 272, pages 71-79.

[39] Zhao and Winkler, 1994, «An *Escherichia coli* K-12 tktA tktB mutant deficient in transketolase activity requires pyridoxine (vitamin B6) as well as the aromatic amino acids and vitamins for growth», *J. Bacteriol.*, vol. 176, pages 6134-6138

The invention claimed is:

1. A recombinant microorganism which exhibits i) a conversion activity from D-ribulose-5-phosphate into D-arabinose-5-phosphate catalysed by an enzyme consisting of a D-arabinose-5-phosphate isomerase which converts D-ribulose-5-phosphate into D-arabinose-5-phosphate, increased in comparison with the same, non-modified microorganism and obtained by increasing the number of copies of the gene coding for said D-arabinose-5-phosphate isomerase, by increasing the expression of the gene coding for said D-arabinose-5-phosphate isomerase and/or by modifying the sequence of the gene coding said D-arabinose-5-phosphate isomerase so as to obtain a form which is more active or more resistant to inhibition in said recombinant microorganism;

ii) an aldolic cleavage activity from D-arabinose-5-phosphate into D-glyceraldehyde-3-phosphate and glycolaldehyde catalysed by an enzyme consisting of a fructose-6-phosphate aldolase which catalyses the cleavage of D-arabinose-5-phosphate into D-glyceraldehyde-3-phosphate and glycolaldehyde, increased in comparison with the same, non-modified microorganism and obtained by increasing the number of copies of the gene coding for said fructose-6-phosphate aldolase, by increasing the expression of the gene coding for said fructose-6-phosphate aldolase and/or by modifying the sequence of the gene coding said fructose-6-phosphate aldolase so as to obtain a form which is more active or more resistant to inhibition in said recombinant microorganism;

iii) an oxidation activity from glycolaldehyde into glycolate catalysed by an enzyme consisting of a glycolaldehyde dehydrogenase which oxidises glycolaldehyde into glycolate, increased in comparison with the same, non-modified microorganism and obtained by increasing the number of copies of the gene coding for said glycolaldehyde dehydrogenase, by increasing the expression of the gene coding for said glycolaldehyde dehydrogenase and/or by modifying the sequence of the gene coding said glycolaldehyde dehydrogenase so as to obtain a form which is more active or more resistant to inhibition in said recombinant microorganism; and iv) an oxidation activity from glyceraldehyde-3-phosphate into 1,3-bisphosphoglycerate catalysed by an enzyme consisting of a glyceraldehyde-3-phosphate dehydrogenase which oxidises glyceraldehyde-3-phosphate into 1,3-bisphosphoglycerate, decreased in comparison with the same, non-modified microorganism and obtained by decreasing the expression of the gene coding said glyceraldehyde-3-phosphate dehydrogenase, by modifying the sequence of the gene coding for said glyceraldehyde-3-phosphate dehydrogenase so as to achieve a reduced expression of the gene and/or the expression of an enzyme the activity of which is reduced, by using elements which destabilise the mRNA obtained after transcription of the gene coding said glyceraldehyde-3-phosphate dehydrogenase and/or by inactivating the gene coding said glyceraldehyde-3-phosphate dehydrogenase in said recombinant microorganism, said recombinant microorganism producing glycolic acid from pentoses and hexoses.

2. The recombinant microorganism according to claim 1, wherein said microorganism exhibits an overexpression of the *E. coli* kdsD gene or a homologue thereof.

3. The recombinant microorganism according to claim 1 wherein said microorganism exhibits an overexpression of the *E. coli* fsa gene or a homologue thereof.

4. The recombinant microorganism according to claim 1, wherein said microorganism exhibits an overexpression of the *E. coli* aldA gene or a homologue thereof.

5. The recombinant microorganism according to claim 1, wherein said microorganism comprises:
α) a first plasmid in which the sequence of the *E. coli* kdsD gene or a homologue thereof and the sequence of the *E. coli* fsa gene or a homologue thereof lie, said sequences being cloned as an operon and under the control of a first inducible or constitutive promoter and
β) a second plasmid in which the sequence of the *E. coli* aldA gene or a homologue thereof under the control of a second inducible or constitutive promoter lies,
said first and second promoters being identical or different.

6. The recombinant microorganism according to claim 1, wherein the expression of the *E. coli* gapA gene or a homologue thereof is decreased but not inactivated with respect to the non-modified microorganism.

7. The recombinant microorganism according to claim 1, wherein the expression of the *E. coli* gapA gene or a homologue thereof is inactivated with respect to the non-modified microorganism.

8. The recombinant microorganism according to claim 1 wherein the phosphotransferase system (PTS), which depends on phosphoenolpyruvate (PEP) and which is coded by the ptsHIcrr operon, is inactivated,
whereas a glucose transport activity coded by *E. coli* galP or *Zymomonas mobilis* glf or a homologue thereof is increased in comparison with the same, non-modified microorganism and obtained by increasing the number of copies of the gene *E. coli* galP or *Zymomonas mobilis* glf or a homologue thereof, by increasing the expression of the gene *E. coli* galP or *Zymomonas mobilis* glf or a homologue thereof and/or by modifying the sequence of the gene *E. coli* galP or *Zymomonas mobilis* glf or a homologue thereof so as to obtain a form which is more active or more resistant to inhibition in said recombinant microorganism and a transformation activity from glucose into glucose-6-phosphase catalysed by an enzyme consisting of a glucokinase which transforms glucose into glucose-6-phosphase is increased in comparison with the same, non-modified microorganism and obtained by increasing the number of copies of the gene coding for said glucokinase, by increasing the expression of the gene coding for said glucokinase and/or by modifying the sequence of the gene coding said glucokinase so as to obtain a form which is more active or more resistant to inhibition in said recombinant microorganism.

9. The recombinant microorganism according to claim 1, wherein said microorganism exhibits at least one of the following characteristics:

v) an oxidation activity from glycolate into glyoxylate catalysed by an enzyme consisting of a glycolate dehydrogenase which oxidizes glycolate into glyoxylate, decreased in comparison with the same, non-modified microorganism and obtained by decreasing the expression of the gene coding said glycolate dehydrogenase, by modifying the sequence of the gene coding for said glycolate dehydrogenase so as to achieve a reduced expression of the gene and/or the expression of an enzyme the activity of which is reduced, by using elements which destabilise the mRNA obtained after transcription of the gene coding said glycolate dehydrogenase and/or by inactivating the gene coding said glycolate dehydrogenase in said recombinant microorganism;

vi) a repression of the genes involved in regulating the aerobic respiratory metabolism induced by a transcriptional regulator capable of repressing the genes involved in the regulation of the aerobic respiratory metabolism, decreased in comparison with the same, non-modified microorganism and obtained by decreasing the expression of the gene coding said transcriptional regulator, by modifying the sequence of the gene coding for transcriptional regulator so as to achieve a reduced expression of the gene and/or the expression of a transcriptional regulator the activity of which is reduced, by using elements which destabilise the mRNA obtained after transcription of the gene coding said transcriptional regulator and/or by inactivating the gene coding said transcriptional regulator in said recombinant microorganism;

vii) a glycolate internalisation induced by at least one protein importing the glycolate, decreased in comparison with the same, non-modified microorganism and obtained by decreasing the expression of the gene coding said at least one protein importing the glycolate, by modifying the sequence of the gene coding for said at least one protein importing the glycolate so as to achieve a reduced expression of the gene and/or the expression of a protein the activity of which is reduced, by using elements which destabilise the mRNA obtained after transcription of the gene coding said at least one protein importing the glycolate and/or by inactivating the gene coding said at least one protein importing the glycolate in said recombinant microorganism;

viii) an irreversible formation activity of methylglyoxal from dihydroxyacetone phosphate (DHAP) catalysed by an enzyme consisting of a methylglyoxal synthase which irreversibly forms methylglyoxal from DHAP, decreased in comparison with the same, non-modified microorganism and obtained by decreasing the expression of the gene coding said methylglyoxal synthase, by modifying the sequence of the gene coding for said methylglyoxal synthase so as to achieve a reduced expression of the gene and/or the expression of an enzyme the activity of which is reduced, by using elements which destabilise the mRNA obtained after transcription of the gene coding said methylglyoxal synthase and/or by inactivating the gene coding said methylglyoxal synthase in said recombinant microorganism;

ix) a conversion activity from fructose-6-phosphate into fructose-1,6-biphosphate catalysed by an enzyme consisting of a phosphofructokinase which converts fructose-6-phosphate into fructose-1,6-biphosphate, decreased in comparison with the same, non-modified microorganism and obtained by decreasing the expression of the gene coding said phosphofructokinase, by modifying the sequence of the gene coding for said phosphofructokinase so as to achieve a reduced expression of the gene and/or the expression of an enzyme the activity of which is reduced, by using elements which destabilise the mRNA obtained after transcription of the gene coding said phosphofructokinase and/or by inactivating the gene coding said phosphofructokinase in said recombinant microorganism;

x) a production activity of D-ribose-1-phosphate from dihydroxyacetone phosphate and glycolaldehyde catalysed by an enzyme consisting of a L-fuculose-phosphate aldolase which produces D-ribose-1-phosphate from dihydroxyacetone phosphate and glycolaldehyde, decreased in comparison with the same, non-modified microorganism and obtained by decreasing the expression of the gene coding said L-fuculose-phosphate aldolase, by modifying the sequence of the gene coding for said L-fuculose-phosphate aldolase so as to achieve a reduced expression of the gene and/or the expression of an enzyme the activity of which is reduced, by using elements which destabilise the mRNA obtained after transcription of the gene coding said L-fuculose-phosphate aldolase and/or by inactivating the gene coding said L-fuculose-phosphate aldolase in said recombinant microorganism; and xi) an oxidation activity from D-glucose-6-phosphate into 6-phospho D-glucono-1,5-lactone catalysed by an enzyme consisting of a cofactor-dependent glucose-6-phosphate dehydrogenase which produces 6-phospho-D-glucono-1,5-lactone from D-glucose-6-phosphate, modified in comparison with the same, non-modified microorganism.

10. The recombinant microorganism according to claim 9, wherein said production activity of 6-phospho-D-glucono-1,5-lactone from D-glucose-6-phosphate catalysed by an enzyme consisting of a cofactor-dependent glucose-6-phosphate dehydrogenase which produces 6-phospho-D-glucono-1,5-lactone from D-glucose-6-phosphate is decreased in comparison with the same, non-modified microorganism and obtained by decreasing the expression of the gene coding said cofactor-dependent glucose-6-phosphate dehydrogenase, by modifying the sequence of the gene coding for said cofactor-dependent glucose-6-phosphate dehydrogenase so as to achieve a reduced expression of the gene and/or the expression of an enzyme the activity of which is reduced, by using elements which destabilise the mRNA obtained after transcription of the gene coding said cofactor-dependent glucose-6-phosphate dehydrogenase and/or by inactivating the gene coding said cofactor-dependent glucose-6-phosphate dehydrogenase in said recombinant microorganism.

11. The recombinant microorganism according to claim 9, wherein said recombinant microorganism exhibits the following characteristics:

xi) an oxidation activity from D-glucose-6-phosphate into 6-phospho D-glucono-1,5-lactone catalysed by an enzyme consisting of a cofactor-dependent glucose-6-phosphate dehydrogenase which produces 6-phospho-D-glucono-1,5-lactone from D-glucose-6-phosphate, increased in comparison with the same, non-modified microorganism and obtained by increasing the number of copies of the gene coding for said cofactor-dependent glucose-6-phosphate dehydrogenase, by increasing the expression of the gene coding for said cofactor-dependent glucose-6-phosphate dehydrogenase and/or by modifying the sequence of the gene coding said cofactor-dependent glucose-6-phosphate dehydrogenase so as to obtain a form which is more active or more resistant to inhibition in said recombinant microorganism;

xii) a formation activity of 2-dehydroxy-3-deoxy-D-gluconate-6-phosphate from D-gluconate-6-phosphate catalysed by an enzyme consisting of a phosphogluconate dehydratase which produces 2-dehydroxy-3-deoxy-D-gluconate-6-phosphate from D-gluconate-6-phosphate, decreased in comparison with the same, non-modified microorganism and obtained by decreasing the expression of the gene coding said phosphogluconate dehydratase and/or by inactivating the gene coding said phosphogluconate dehydratase in said recombinant microorganism; and xiii) a formation activity of glyceraldehyde-3-phosphate and pyruvate from 2 dehydroxy-3-deoxy-D-gluconate-6-phosphate catalysed by an enzyme consisting of a 2-dehydroxy-3-deoxy-phosphogluconate aldolase which produces D-glyceraldehyde-3-phosphate and pyruvate from 2-dehydroxy-3-deoxy-D-gluconate-6-phosphate, decreased in comparison with the same, non-modified microorganism and obtained by decreasing the expression of the gene coding said 2-dehydroxy-3-deoxy-phosphogluconate aldolase and/or by inactivating the gene coding said 2-dehydroxy-3-deoxy-phosphogluconate aldolase in said recombinant microorganism.

12. A process for producing glycolic acid comprising the steps of:
   a) culturing a recombinant microorganism as defined in claim 1 in a culture medium comprising, as a carbon source, at least one pentose and/or at least one hexose; and
   b) recovering glycolic acid from the microorganism and/or in the culture medium.

13. The process according to claim 12, wherein said cultured recombinant microorganism is a recombinant microorganism in which the expression of the *E. coli* gapA gene or a homologue thereof is decreased but not inactivated with respect to the non-modified microorganism, and in that the implemented carbon source only comprises one element chosen from D-glucose, D-xylose, L-arabinose and a mixture thereof.

14. The process according to claim 12, wherein said cultured recombinant microorganism is a recombinant microorganism in which the expression of the *E. coli* gapA gene or a homologue thereof is inactivated with respect to the non-modified microorganism, and in that the carbon source comprises, in addition to D-xylose and/or L-arabinose and/or D-glucose, one or more C2, C3 and C4 compounds chosen from malate, pyruvate, succinate, acetate and a mixture thereof.

* * * * *

UNITED STATES PATENT AND TRADEMARK OFFICE
CERTIFICATE OF CORRECTION

Page 1 of 1

PATENT NO. : 11,851,696 B2
APPLICATION NO. : 17/259124
DATED : December 26, 2023
INVENTOR(S) : Cléa Lachaux et al.

It is certified that error appears in the above-identified patent and that said Letters Patent is hereby corrected as shown below:

On the Title Page

Item (73) Assignee, Please change "Institut National Des Sciences Appliquées De Toulouse, Toulouse (FR); Centre National De La Recherche Scientifique, Paris (FR); Institut National Recherche Pour L'Agriculture, L'Alimentation Et L'Environement, Paris (FR)" to -- Institut National Des Sciences Appliquées De Toulouse, Toulouse (FR); Centre National De La Recherche Scientifique, Paris (FR); Institut National Recherche Pour L'Agriculture, L'Alimentation Et L'Environnement, Paris (FR) --.

Signed and Sealed this
Eighth Day of October, 2024

Katherine Kelly Vidal
*Director of the United States Patent and Trademark Office*